US012667659B2

(12) United States Patent
Schrul et al.

(10) Patent No.: US 12,667,659 B2
(45) Date of Patent: Jun. 30, 2026

(54) NEEDLE INSERTION MECHANISM FOR AN INJECTION DEVICE WITH AN IMPROVED IMPACT RESISTANCE

(71) Applicant: Ypsomed AG, Burgdorf (CH)

(72) Inventors: Christian Schrul, Burgdorf (CH);
Stefan Burren, Schwarzenburg (CH);
Mario Bernhard, Burgdorf (CH);
Andres Mellenberger, Koppigen (CH);
Markus Tschirren, Burgdorf (CH);
Michael Dobler, Balsthal (CH); Marc Fiechter, Konolfingen (CH); Susanne Schenker, Aarwangen (CH)

(73) Assignee: Ypsomed AG, Burgdorf (CH)

( * ) Notice: Subject to any disclaimer, the term of this patent is extended or adjusted under 35 U.S.C. 154(b) by 981 days.

(21) Appl. No.: 17/878,403

(22) Filed: Aug. 1, 2022

(65) Prior Publication Data

US 2022/0362458 A1      Nov. 17, 2022

Related U.S. Application Data

(63) Continuation of application No. PCT/EP2021/051933, filed on Jan. 28, 2021.

(30) Foreign Application Priority Data

Feb. 4, 2020    (EP) ..................................... 20155307

(51) Int. Cl.
*A61M 5/142*        (2006.01)
*A61M 5/158*        (2006.01)
*A61M 5/50*        (2006.01)
(52) U.S. Cl.
CPC .......... *A61M 5/14248* (2013.01); *A61M 5/50* (2013.01); *A61M 2005/14252* (2013.01);
(Continued)

(58) Field of Classification Search
CPC ........... A61M 2005/14252; A61M 2005/1585; A61M 2005/14284
See application file for complete search history.

(56) References Cited

U.S. PATENT DOCUMENTS

2008/0249473 A1    10/2008  Rutti et al.
2013/0060233 A1     3/2013  Oconnor et al.
(Continued)

FOREIGN PATENT DOCUMENTS

EP          3501576 A1      6/2019
EP          3539592 A1      9/2019
(Continued)

OTHER PUBLICATIONS

Extended European Search Report issued in European Patent Application No. 20155307.0, mailed on May 4, 2020, 8 pages.
(Continued)

*Primary Examiner* — Courtney B Fredrickson
*Assistant Examiner* — Kayla M. Turkowski
(74) *Attorney, Agent, or Firm* — Dorsey & Whitney LLP

(57)              ABSTRACT

Needle insertion mechanisms include a housing and a needle holder, the needle holder being linearly guided by the housing to be moved along the needle-axis. A slider linearly guided by the housing and transversally moveable with respect to the needle-axis from a first to a second slider position. The needle holder is operatively coupled to the slider when the slider is in the first position, thereby retaining the needle holder in a retracted position against the bias of a spring acting on the needle holder. In the second position the slider is decoupled from the needle holder and the holder is moved into an inserted position by the spring. A blocking member arranged between the slider and the housing blocking movement of the slider into the second position, is moved by an active drive thereby unblocking the
(Continued)

movement of the slider and subsequently moving the slider to the second position.

15 Claims, 36 Drawing Sheets

(52) U.S. Cl.
     CPC .............. *A61M 2005/1585* (2013.01); *A61M 2005/1586* (2013.01)

(56) References Cited

U.S. PATENT DOCUMENTS

| | | | | |
|---|---|---|---|---|
| 2016/0213840 A1* | 7/2016 | Schabbach | ............ | A61M 5/158 |
| 2019/0160225 A1 | 5/2019 | Verlaak et al. | | |
| 2020/0086051 A1* | 3/2020 | Grygus | ............... | A61M 5/2033 |

FOREIGN PATENT DOCUMENTS

| | | | |
|---|---|---|---|
| EP | 3603700 | A1 | 2/2020 |
| EP | 3862037 | A1 | 8/2021 |
| GB | 2552340 | A | 1/2018 |
| WO | 2006108809 | A1 | 10/2006 |
| WO | 2010029054 | A1 | 3/2010 |
| WO | 2011012465 | A1 | 2/2011 |
| WO | 2014154490 | A2 | 10/2014 |
| WO | 2016053954 | A1 | 4/2016 |
| WO | 2018024625 | A1 | 2/2018 |
| WO | 2021156130 | A1 | 8/2021 |

OTHER PUBLICATIONS

International Search Report and Written Opinion issued in International Application No. PCT/EP2021/051933, mailed on Apr. 14, 2021, 12 pages.

* cited by examiner

NEEDLE INSERTION MECHANISM FOR AN INJECTION DEVICE WITH AN IMPROVED IMPACT RESISTANCE

CROSS-REFERENCE TO RELATED APPLICATIONS

This application is a continuation of International Application No. PCT/EP2021/051933 filed on Jan. 28, 2021, which in turn claims priority to European Patent Application No. 20155307.0 filed on Feb. 4, 2020, each of which are incorporated by reference herein, in their entirety and for all purposes.

TECHNICAL FIELD

The present disclosure relates to a needle or cannula insertion mechanism for an injection or infusion device, the injection device may be a motor driven patch injection device or bolus injector. The needle insertion device may provide impact resistance to prevent unintentional needle insertion or misfiring during an impact, for example during a drop test.

BACKGROUND

Injection and infusion devices are used for the subcutaneous delivery of liquid medicaments to a patient. Such injection devices are often pen-shaped, having a long axis and are called injection pens. The injection pens include a housing, which can hold a dose setting and dose delivery mechanism. The medication is generally present in a cartridge or in a prefilled syringe. A cartridge is normally attached to the housing of the injection pen using a cartridge holder. The user sets a dose of medication which is subsequently delivered from the cartridge. Such injection pens are used to deliver separate injections and not intended for continuous delivery of a medicament. The needle is attached to the injection pen each time before use and the needle penetrates a septum that is attached to the cartridge.

Infusion devices deliver the medication from the cartridge using a drive mechanism and a control mechanism that controls the advancement of a piston rod that abuts a moveable plunger present in the cartridge containing the medication. The medication is delivered to the patient via a fluid path and an external infusion set including a hollow needle or cannula for subcutaneous delivery. With such infusion devices both continuous and temporary medicament delivery profiles can be programmed.

A patch device is an example of an infusion device that is attachable to the skin of the patient. Such patch devices do not need an external infusion set for delivery as the hollow needle or cannula is directly contained in the patch device and may be inserted into the patient therefrom.

The injection and infusion devices require an insertion mechanism for insertion of a needle in the subcutaneous tissue before the medicament is injected or infused using a delivery mechanism. For a safe operation of those devices it must be ensured that the delivery mechanism is activated after the needle insertion has been completed to prevent undesired needle sticks when the device is removed from the injection site. It is beneficial for such injection or infusion devices that the insertion mechanism is activated once needed, for example when the user presses a button on the device or activates the needle insertion via a wireless connection using an external device such as a smart phone, or automatically after sensors indicate correct attachment of the device and needle insertion. Therefore such devices may have safety mechanisms which prevent needle insertion before dose delivery.

To increase the usability for the end-users, such devices may have an automatic release and starting mechanism, thus once started an automatic cascade of steps is triggered or released for needle insertion, medicament delivery, needle retraction and locking of the device once the medicament has been delivered. For disposable devices, this cascade of events cannot be reversed to prevent re-use. For a safe operation it is thus of importance that the cascade of steps is only triggered once desired and therefore it is not desired to have unintentional release of the insertion mechanism when the device has not been applied yet, for example, not been attached to or pushed upon the skin of the patient. Also an automatic release during storage is not desired as expensive medication may be wasted without being injected into the patient. A reason for such unintentional release of the insertion mechanism may be mechanical impact on the housing of such a device by an external part, or alternatively a drop of the device on the floor or an impact during transport of the device. A release of the insertion mechanism will expose the needle and increase the risk of undesired needle sticks which leads to discomfort and may even result in loss of the device containing an expensive medicament as the needle may be bent and/or the delivery mechanism may be activated such that the medicament is expelled into the environment.

In WO 2014154490 A1 an injection pen is provided with an activator that is snap fitted onto the housing and the snap fit connection is selected to prevent misfiring during a drop test. The pen shaped injector cannot be attached to the skin and is spring driven which makes the control of the sequences for needle insertion and medicament delivery difficult as the spring forces are released once a coupling or latching mechanism is released.

In EP 3603700 A1, a needle insertion mechanism is provided that is released by moving a slider using a motor driven rack and pinion to release a spring based needle holder. There are no special precautions taken to improve the fixation of the slider when in the starting position.

In WO 2011012465 A1 a patch injection device is provided with a manually operated slider including retaining means to prevent the slider from moving towards a needle activated position. The retaining means are not optimized for impact resistance to prevent misfiring during a drop test, and moreover, the manual control of the slider reduces the control (and separation of) the needle insertion step and the medicament delivery step.

It is an object of the present disclosure to overcome the above mentioned drawbacks and provide a needle insertion mechanism with an improved reliability, robustness and resistance against unintentional needle insertion.

These objectives are met by providing a needle insertion mechanism having an active drive for driving a slider that may be moved to discrete positions, starting from a first slider position mechanically blocking the position of a needle holder in a needle retracted position, to a second slider position for releasing the needle holder for movement into the needle insertion position. A blocking member may prevent the movement out of the first slider position towards a second slider position. Several variants for the blocking member based on form-fit or friction fit engagements between the slider and the housing are also described in the present disclosure.

SUMMARY

In a first aspect, a needle insertion mechanism is disclosed for an injection device or an infusion device including a housing and a needle holder for holding an insertion needle or cannula. The insertion needle may be defined as a hollow needle for insertion into the skin or insertion into a reservoir. The needle holder may be linearly guided by the housing to be moved along the longitudinal axis of the needle. The linear guide may be a splined or key-keyway guide. The longitudinal axis of the needle may be arranged parallel to a tubular housing part or perpendicular to a surface of the housing that is intended for attachment to the skin of a patient. The needle insertion mechanism may further include a slider which may be linearly guided by the housing and transversally moveable with respect to the longitudinal axis of the needle from a first slider position to a second slider position. Again the linear guide for the slider may be a splined or a key-keyway engagement including linear keys. The slider may be moved within the housing and may not be accessible to the patient, alternatively the slider may partially extend outside of the housing. In the first slider position, the slider may be operatively coupled to the needle holder thereby retaining the needle holder in a needle retracted position against the bias of a spring force acting on the needle holder. The operative coupling may be a simple abutment between two surfaces but may also be a motion-link coupling, a splined engagement or a threaded engagement. The bias of the spring force intends to move the needle holder along the needle axis, and by acting upon the holder, the needle itself is also indirectly biased to be moved along the needle axis. The needle retracted position may be within the housing, and for instance the needle and/or a tip of the needle is located within the housing. In the second slider position the slider is decoupled or released from the needle holder and the needle holder is moved into the needle insertion position for instance by the spring force acting upon the needle holder. The decoupling may be a simple release of the abutment surfaces on the slider and the needle holder due to the movement of the slider. When moving from the needle retracted to the needle insertion position, the needle holder is guided by the housing. The needle insertion position may be a position where the needle or a tip of the needle extends outside of the housing and is inserted into the skin of a patient. Alternatively, the needle insertion position may designate a position where the needle is outside a first part of the housing and moves into or is inserted into a second part of the housing. The second part of the housing may include a reservoir closed by a membrane and by moving into the needle insertion position the needle may penetrate the membrane of the reservoir containing a medicament. The needle insertion mechanism may have a releasable coupling arrangement arranged between the slider and the housing which may be coupled when the slider is in the first slider position thereby retaining the slider in the first position against an actuation threshold, which may be surpassed to decouple the slider for movement into the second position, and the slider may be driven by an active drive, which may provide precise control of the speed and position of the slider. An alternative for the coupling arrangement may be an attachment means between the slider and the housing. And the actuation threshold may be also identified as an activation force or a barrier that may be overcome before the slider can be moved to release the releasable coupling.

The housing may provide structural support to components of the needle insertion mechanism and the injection device may be located within the housing and may provide or include a barrier to the external environment for dust, moisture and liquids. The housing may be part of a sterile barrier enclosing a needle insertion mechanism or alternatively may form a fluid tight barrier. The result may be a robust device capable of remaining sterile during storage for an extended period of time (e.g., an extended shelf life). The housing may be an internal housing or an external housing. The internal housing may be a frame for holding internal components (a mechanism holder) of the insertion mechanism and may include linear guides for guiding a slider and/or bearing surfaces for supporting rotating parts. The needle holder holding the insertion needle may ensure that the needle may be inserted into the skin of a patient or into the septum of a cartridge. The needle holder may transfer force and movement from the insertion mechanism to the insertion needle and may be linearly guided by the internal or external housing using a splined, key-keyway or groove-protrusion engagement.

The operative coupling between the slider and the needle holder when in the first slider position may be a direct coupling such as an abutment, or a friction-fit engagement, or a form-fit engagement, or an adhesive connection, or a magnetic force existing between the slider and the needle holder. Alternatively an indirect coupling may be provided between the slider and the needle holder via a third part that may be engaged with the housing or a housing part. The operative coupling may retain the needle holder in a needle retracted position against the bias of a biasing member configured to automatically move the needle holder from the needle retracted position into the needle insertion position. The biasing member may provide a biasing force on the needle holder and the force may be directly or indirectly guided to the housing such that the needle holder remains in the needle retracted position preventing unintended needle insertion. As the mechanism is configured to automatically initiate a cascade of sequences including needle insertion and/or retraction, controlling the position of the slider and preventing unintentional movement may be provided either by using a releasable coupling arrangement or a blocking member as described hereafter. The biasing member may be selected from a spring, a coil spring, a compression spring, a leg spring, a hydraulic or gas driven piston, a magnetic or electromagnetic force transducer.

In the second slider position or during movement from the first slider position towards the second slider position, the needle holder may be decoupled from the slider such that the biasing force provided by the biasing member moves the needle holder into the needle insertion position while being linearly guided by the housing as the needle holder is free to move when decoupled from the housing, which may provide a fast and efficient insertion of the needle.

The releasable coupling arrangement or blocking member may be a broad definition for an attachment means or an engagement means or a retention or retaining means, all which may serve the purpose of retaining the slider in the first slider position or blocking movement out of the first slider position and thereby preventing unintentional needle insertion prior to the desired needle insertion as the operative coupling between the slider and the needle holder keeps the slider in the first slider position. Unintentional needle insertion may occur, for example, during storage, during transport or during impact forces such as unintentional dropping of the needle insertion mechanism or a device including the needle insertion mechanism in the absence of the releasable coupling arrangement or blocking member. The releasable coupling arrangement may be releasable, as a desired movement of the slider from the first slider position to the second slider position may be allowed and controllably released by the active drive. The releasable coupling arrangement or blocking member may be functionally or structurally arranged between the slider and the housing. The releasable coupling arrangement may be between coupling members that may be a part of the slider and the housing which may directly interact or, alternatively, the coupling arrangement may involve other parts to form an indirect releasable coupling arrangement or blocking member between the slider and the housing.

The releasable coupling arrangement with the actuation threshold will be described in the following. An actuation threshold defines an activation or actuation threshold, which may serve as a barrier in terms of force or energy needing to be overcome before the slider can start the linear movement towards the second slider position. The movement of the slider with respect to the housing may be a low friction movement which may be started once the actuation threshold has been overcome. The actuation threshold may meet certain requirements in that the threshold force may be low enough to prevent excessive energy consumption for the drive mechanism for surpassing the threshold whereas the threshold may be high enough to prevent unintentional movement of the slider due to impact forces. Thus the releasable coupling arrangement may be configured for a specific actuation threshold such that the drive mechanism enables the slider movement whereas an impact during a drop test will generate forces on the slider and the coupling arrangement that are below the actuation threshold. The actuation threshold may be configured by the structures of the coupling members and by the materials and surface characteristics selected. The actuation threshold may depend on the specific speed used, for instance a low threshold may be at low slider speeds whereas a higher threshold may be at higher speeds. This may be achieved, for example, by using viscoelastic materials or polymers acting as shock absorbers. The actuation threshold may be configured to withstand a standardized drop test such that the actuation threshold is high enough to obtain a safe and reliable device without compromising the energy consumption required to overcome the threshold. The coupling arrangement may provide reliability and robustness to the device.

The drive mechanism for driving the slider may include an active drive, for example based on an electric motor, which may directly or indirectly drive the slider via a gearing mechanism or a rack and pinion arrangement. The use of an active drive may provide for good control, for example by the number of revolutions or the activation time of the electric motor, of the position of the slider when moving from the first position to the second position. Additionally, the speed of movement of the slider can be controlled by, for example, selecting the rotational speed of the active drive and/or the gearing mechanism. Therewith also the second position may be correctly defined in terms of position and time as the slider may move at intermediate positions or may move linearly from the second position to a third slider position. The electric motor may drive the slider to release or unblock the operative coupling between the slider and the needle holder where a separate biasing member moves the needle holder from the retracted into the inserted position. Separating the drive mechanism of the slider and the needle insertion may improve the reliability of the device. Movement of the slider using a spring disclosed in the WO 2011012465 A1 for moving the slider and simultaneously inserting the needle via a motion link has the disadvantage that the slider may jam or block due to the sudden impact of a decompressing spring on the slider and the slider may be difficult to stop at intermediate stop positions.

Optionally, the slider may be driven by a hydraulic or pneumatic drive system.

The active drive may be selected from an electric drive that is battery powered, or a magnetic drive, or a piezoelectric drive, or a shape memory alloy driven drive, or an electro-active polymer driven drive. The electric drive may include an electric motor.

These examples for active drives may provide for a controlled movement of the slider compared to spring-driven devices without control of the release force for the spring, for example, once the spring force is released the spring energy may be rapidly released and the fast movement of the slider may lead to a jammed slider due to buckling of the slider within a guide. Alternatives based on manually driven sliders have the disadvantage that each user will push or pull the slider at different speeds and with different forces. By using active drives of the present disclosure, the control of the slider movement is improved thereby improving the reliability of the device.

The releasable coupling arrangement in the needle insertion mechanism may include a first coupling member on the slider and/or a second coupling member on the housing or on a housing part, and the first coupling member and the second coupling member may be in a form fit or a friction fit engagement when the slider is in the first slider position. Alternatively, a weak spot or a predetermined breaking point may be used between the first and second coupling members. The releasable coupling arrangement may act as a shock absorber between the slider and the housing.

The coupling members may be selected from a protrusion, a recess, a post, an elastic member, a pressure sensitive material, a magnet, a hook, a releasable snap fit connector, hook and loop tape, or an electromagnetic switch. The coupling members may be constructed from a plastic material or from a metal and may be integrally formed with the internal or external housing (for example using injection molding) or may be a separate part coupled to the housing, for example a stamped metal part. Using integrated members or separate members may have the benefit of leaving many design options open for establishing the releasable coupling arrangement.

The coupling members may move with respect to each other to decouple the releasable coupling arrangement when the slider moves towards the second slider position to overcome the actuation threshold. The relative movement between the first and second coupling member may be a linear and/or rotary movement. A linear movement may be oriented parallel or perpendicular to needle axis. A form fit engagement may be established between two protrusions, between a protrusion engaging a recess, and/or between two engaging teeth such as saw teeth engaging each other. A friction fit engagement may be established between two abutting surfaces that are textured or roughened, for example, they may include sandpaper, structured paper or the two surfaces may be constructed from different materials having different frictional coefficients. A form fit engagement may be less dependent on dimensional tolerances of the parts, that for instance may change during the course of storage, e.g., over shelf life, and therewith a form fit engagement may be used and/or established. Optionally, one or both of the coupling members may be constructed from a metal as metals that are less susceptible to physical aging compared to polymeric materials. Combinations of a form fit and a friction fit engagement may be options that the skilled person selects as well. The two coupling members may form a releasable one-way ratchet when the slider is in the first position.

The releasable coupling arrangement may provide for the actuation threshold. The actuation threshold prevents the movement of the slider from the first slider position into the second slider position for instance during a drop test for the needle insertion mechanism from a height of 1 m onto a drop surface selected from a concrete floor or wood having a density above 600 kg/m3.

The needle insertion mechanism may be subjected to impact forces during transport and use, and forces generated during a drop may shift the slider and release the coupling arrangement between the slider and the needle holder resulting in unintentional needle insertion movement and needle exposure to the patient. The safety and reliability may thus be improved by the actuation threshold and the releasable coupling arrangement may be configured to withstand such impact forces. The design criteria for the coupling members forming the releasable coupling arrangement are, in the present disclosure, related to and defined by standardized drop tests and such tests can be repeated if performed according to the specific ASTM, DIN IEC or ISO standard. Additionally such tests may require that the device including the needle insertion mechanism be dropped from a standardized height on a standardized surface with different orientations for the device. Such a drop test may be repeated, for instance three times, using the same device and each time a different orientation is selected. The different orientations are selected to define a worst case scenario for the needle insertion mechanism, for instance, along the axis of the releasable coupling arrangement or along the axis of the slider movement. The drop tests may be performed using a plurality of devices including the needle insertion mechanism and each device may be repeatedly tested at different orientations including the worst case orientation. A drop test in the present disclosure is thus not related to a single device and a single drop test but includes a plurality of devices. The outcome of the test in terms of pass or fail correlates to the ensemble of devices tested and is statistically evaluated. For example at least 10 devices are tested each at three different orientations, or at least 50 devices are tested, or 200 devices are tested and the failure rate is below 10%, or below 5% or below 1%. The drop test may be repeated in that a single device from the cohort is repeatedly dropped at different orientations.

In the following a drop test according to IEC 60601-1: 2005 Chapter 15.3.4.1 is described in more detail:

The testing device will be dropped three times with three different orientations from a height of at least one meter onto a drop surface of wood of having a density above 600 kg/m3 (high density wood). A selection between one of most common hardwoods like oak, beech, birch, ash and maple appears to be acceptable for the drop test. The plate of wood for the drop surface has a thickness of at least 50 mm and is positioned on a concrete floor. Alternatively, the drop test is directly performed on a concrete floor. An alternative drop test is described in EN ISO 11608-1:2015 where the test object is also dropped from a height of one meter each time using three different orientations for the device. Equivalent tests after ASTM (for example ASTM D5276) may be used accordingly without giving significant different test results.

According to an embodiment, the first coupling member or the second coupling member may be shaped as a protrusion which may be plastically deformed when the slider is moved from the first slider position to the second slider position to release the form fit engagement. The first and the second coupling members may be shaped as a protrusion extending from a surface of the slider or the housing part. The two protrusions may interlock and movement of the slider plastically deforms one or both of the protrusions to release the form-fit engagement. One of the first and second coupling members may be shaped as a recess in the surface of the slider or housing engaging a protrusion on the other one of the first and second coupling members. Moving the slider may plastically deform the protrusion to release the form fit. Alternatively, one of the protrusions may be moved along the protrusion axis to release the form fit. The protrusions may have ramped surfaces to control the actuation threshold, for example, first the coupling members slide over each other during slider movement followed by plastic deformation of at least one of the protrusions. The use of protrusions extending from surfaces or recesses in surfaces may facilitate integration into injection molded parts.

The first coupling member and/or the second coupling member may be located at a resilient member, such as a flexible arm, and the resilient member may be elastically deformed to release the form fit engagement between the first coupling member and the second coupling member. The elastic deformation may thereby establish or at least contribute to the actuation threshold when the slider is moved from the first slider position to the second slider position. When the slider moves towards the second slider position, the first and/or second coupling member may be deflected from each other and the force required for the deflection may define or contribute to the actuation threshold for slider movement. The surfaces of the coupling members sliding over each other may be textured such that a friction force may be added to the actuation force defined by flexing the resilient member.

The form fit and/or friction fit engagement may be integrated with the guiding means for linearly guiding the slider with respect to the housing. The slider may be guided by a key-keyway (splined) engagement and the first and second coupling members can be part of the key-keyway engagement.

Optionally, the needle insertion mechanism may include a releasable second form fit engagement which may be established between a third coupling member on the slider and a fourth coupling member on the housing when the slider is moved from the first slider position to the second slider position after the form fit engagement between the first coupling member and the second coupling member has been released and where the third coupling member and/or the fourth coupling member is located at the resilient member, for instance, at the same resilient member carrying the first coupling member or the resilient member carrying the second coupling member. The first and third coupling member may be at one flexible arm being part of the slider engaging and array of second and fourth coupling members present on the housing. The flexible arm may perform a pendulum movement perpendicular to the slider movement and subsequent coupling arrangements may be broken and re-established. The elastic member may have a plurality of coupling members and by shifting the slider, one of the coupling members of the slider may repeatedly engage one of the coupling members on the housing. The repeated coupling and decoupling may slow down the slider movement upon drop-test impact. For example the coupling member on the slider may be a "T" shaped having two oppositely oriented coupling members at the top of the "T" connected to the leg of the "T" forming a flexible arm. The coupling members on the "T" may repeatedly engage to form releasable form fit engagements with a rack of coupling members on the housing and the flexible leg of the "T" performs the pendulum movement. This arrangement may provide additionally safety and may be used to define intermediate slider positions for integrating additional functionalities into the slider system. For example a slider position dedicated to the release of the delivery mechanism or to a blocking of the position of the inserted needle in the inserted position or to mechanically releasing a starting button.

In an embodiment of the needle insertion mechanism, the form fit engagement between the first coupling member and the second coupling member may include a motion-link system, the first coupling member on the slider being shaped as a protrusion engaging the second coupling member shaped as a slotted link or groove on the housing, or the first coupling member on the slider being shaped as a slotted link or groove engaging the second coupling member shaped as a protrusion on the housing. The motion-link system may be an example of a blocking member described hereafter.

The motion-link system, as an example of the form fit engagement, may provide a reliable option for locking the slider in the first slider position and may not be susceptible to aging of (plastic) materials during storage over time, such as aging over the shelf life of the product. For instance, the motion-link may block the slider movement completely (e.g., high threshold). The slotted link may be provided on other parts than the housing and slider, for example, on an outer housing part or a sub-frame within the housing such as, for example, a mechanism holder. The slotted link may include at least two linear sections connected to, and oriented at an angle to each other and both sections may be configured to engage the protrusion. One linear section may be oriented parallel to the orientation direction of the slider, thereby allowing the movement of the protrusion through the link and allowing movement of the slider towards the second slider position. The other linear section may be oriented perpendicular or oblique to the one linear section. When the releasable coupling arrangement is coupled, the protrusion cannot move from one section of the slotted link to the other section and therewith preventing slider movement. The motion-link arrangement may provide a reliable alternative form fit arrangement for the releasable coupling arrangement.

The form fit engagement based on the motion-link may be released by moving the slider parallel to the longitudinal axis of the needle prior to transversely moving the slider from the first slider position to the second slider position. Releasing the form fit coupling using the motion-link may require that either the protrusion is moved out of the first section of the slotted link into the other section allowing slider movement or, vice versa, the slotted link is moved with respect to the protrusion. Thus either the part holding the protrusion is moved to release the protrusion or the part holding the slotted link is moved. After moving one of the two parts the slider may be free to move from the first slider position to the second slider position.

In another embodiment of the needle insertion mechanism, the first coupling member is on the slider and the second coupling member is on the needle holder, which in this case acts as, or forms the housing part. For this embodiment, the bias of the spring force may keep the first and second coupling members in the form fit engagement.

This is an example of an indirect releasable coupling arrangement between the slider and housing, as the needle holder may be linearly guided by (or coupled to) the housing. The first and second coupling members may be kept in an engaged configuration, for example in abutment by the spring that also enables the movement of the needle holder towards the inserted position. The first and second coupling members respectively on the slider and the needle holder may have sloped surfaces that slide over each other during movement of the slider from the first to the second position. Optionally, the surfaces of coupling members that are in abutment may be structured to increase the friction fit or may be lubricated to decrease the friction fit therewith providing a wide range of options (angles of sloped surfaces, structured or lubricated surfaces) to fine tune the actuation threshold to the specific needs, which may vary with the weight and shape of the device and the specific slider orientation within the device.

The slider may be driven by the active drive from the first to the second slider position using a rack and pinion arrangement, for instance, including a cam shaft rotatably engaged with the housing and having the pinion, and the rack or gear rack may be part of the slider such that rotation of the cam shaft by the active drive (e.g., electric motor) rotates the pinion to drive the slider against the actuation threshold.

The pinion may include a gear wheel with gear teeth engaging teeth of the gear wheel. The rack and pinion arrangement may include a plurality of gear wheels or worm wheels to gear down or gear up the rotation of the active drive (e.g., electric motor) and by selection of different gearing ratios different actuation forces for the active drive can be selected. The rack or gear rack may have its teeth positioned on a single linear axis, but alternatively, the rack may include two linear sections or one curved section. The configuration of the rack may allow for movement of the slider by the gear teeth of the pinion during rotation of the cam shaft that is off-set from the linear movement from the first to the second slider position. The off-set movement may be used to release, for example, the motion-link engagement described above, or to retract a protrusion from a form fit engagement. Optionally, the rack may include two linear axes that are perpendicular or oblique to each other. Rotation of the cam shaft with its gear wheel may thus first shift the slider perpendicular to the direction for movement from the first to the second slider position.

Optionally, the rack and pinion arrangement may be configured to move the slider parallel to the longitudinal axis of the needle prior to transversally moving the slider from the first slider position to the second slider position. This may be of interest for the embodiment where the releasable coupling arrangement is established using a motion-link configuration between the slider and the housing. The gear wheel of the pinion may first engage a section of the rack oriented parallel to the longitudinal axis of the needle and may subsequently drive a section of the pinion oriented perpendicular to the longitudinal axis of the needle. The rack and pinion arrangement may thus serve a dual purpose in first moving the slider to release a motion-link thereby allowing the subsequent movement of the slider from the first to the second slider position using a second section of the rack.

In yet another embodiment, the first coupling member and/or the second coupling members may be located at the resilient member, for instance at a flexible arm which is in abutment with the cam shaft. The abutment may prevent elastic deformation of the resilient member and rotation of the cam shaft may release the abutment for the resilient member thereby enabling the release of the form fit engagement between the first coupling member and the second coupling member. Thus the flexing of the flexible arm may be required to release the coupling arrangement once the cam shaft has been rotated, or rotated over a first angle.

The cam shaft may include an abutment surface, for example provided on a protrusion extending perpendicular to the cam shaft axis, and this abutment surface may contact a counter abutment surface present on the flexible arm. The flexible arm may be present on the slider or the housing. This abutment may prevent movement of the flexible arm and thereby release of the releasable coupling arrangement between the first and the second coupling member. When the cam shaft is rotated over a first angle, the abutment between the abutment surface of the cam shaft and the counter abutment surface on the flexible arm may be released and the arm can flex thus enabling the first and second coupling members to move relative to each other and release their form fit or friction fit engagement. The gear wheel on the cam-shaft or the rack present on the slider may be adapted to allow for a rotational play before the rack and pinion arrangement starts moving the slider. For example the gear wheel and or the rack may have a missing tooth thereby delaying the translation of the rotational movement of the cam shaft in a linear movement of the slider. The delay or rotational play may be used to first release the abutment between the cam shaft and the flexible arm.

Optionally and additionally to the releasable coupling arrangement between the slider and the housing providing the actuation threshold, the active drive may include a self-locking feature forming a second actuation threshold to be surpassed to activate the active drive before moving the slider and surpassing the actuation threshold. The self-locking feature may provide a second actuation threshold to be overcome by the active drive before the slider starts moving. This may provide an additional safety mechanism for example for severe impact or gravitational forces acting on the insertion mechanism or on a delivery device including the needle insertion mechanism.

In the embodiment including a second actuation threshold, the self-locking feature may be selected from a magnetic break, a gearing such as a worm gear, or a screw gear, or a friction fit engagement to the housing.

An example for the self-locking feature is a magnetic break integrated into an electric motor. An example of the gearing is the overall gearing ratio selected for movement of the slider. The rotation of the pinion may be transferred to movement of the rack with a gearing ratio, additionally the rotation of the active drive may be transferred to a rotation of the pinion which again may be subjected to a gearing ratio. The overall gearing ratio is the sum of both gearing ratios and this overall gearing ratio may provide an actuation threshold. An example of the friction fit engagement may be the cam shaft that slides or rotates in a housing or a housing part. The friction fit engagement may be a direct engagement between the cam shaft and the housing or via an elastomeric element such as an O-ring. The O-ring may serve a dual purpose by preventing either water, or contamination via the cam shaft into the device or a part of the device, or it may serve the purpose of providing a frictional resistance to be overcome before the cam-shaft starts rotating.

In all embodiments described above, the first and/or second coupling members may include sloped surfaces that mutually engage each other when the slider is in the first position and which slide over each other when the slider moves from the first to the second position. The angle of the mutually engaging surfaces may define the force required to release the coupling members from their form fit or friction fit engagement. Thus by playing with the sloped surfaces the actuation threshold may be tuned to the specific needs.

In yet another embodiment, the slider may be transversely moveable with respect to the longitudinal axis of the needle from the second slider position to a third slider position, and a fifth coupling member on the slider and a sixth coupling member on the housing may be configured to engage in a non-releasable third form fit engagement when the slider is moved from the second slider position to the third slider position. The slider may be moved linearly towards the third position and once the injection has been performed the slider is locked in a non-releasable third form fit. This may automatically prevent re-use of a device intended for single-use only. Alternatively, the device parts may be prevented from rattling or being detached from the housing after use. The fifth and sixth coupling members may be configured as hooks or saw teeth that engage each other and which may be attached to flexible arms. For example a hook or protrusion present on a flexible arm attached to the slider may enter a recess present in the housing once moved to the third slider stop position thereby locking the slider to the housing (or a housing part) once the third form-fit engagement has been established.

In a second aspect, the needle insertion mechanism including a blocking member will be described. The blocking member may be a blocking part, a blocker, or a blocking object.

A needle insertion mechanism for an injection device may include a housing and a needle holder holding an insertion needle. The needle holder may be linearly guided by the housing to be moved along the longitudinal axis of the needle. The insertion mechanism further may include a slider linearly guided by the housing and transversely moveable with respect to the longitudinal axis of the needle from a first slider position to a second slider position. In the first slider position, the slider may be operatively coupled to the needle holder thereby retaining the needle holder in a needle retracted position against the bias of a spring force acting on the needle holder and in the second slider position the slider, or by moving out of the first slider position, the slider may be decoupled from the needle holder and the needle holder is moved into the needle inserted position by the spring force. The needle insertion mechanism may have a blocking member which may be arranged between the slider and the housing and which blocks the movement of the slider from the first to the second position. The blocking member may be moveable by the active drive thereby unblocking or releasing the movement of the slider. Subsequently the slider may be moved to the second slider position by the active drive.

The blocking member can be moved from a blocked to an unblocked position. The blocking member blocks the movement of the slider and once moved by the active drive, the blocking member is in an unblocked position such that the slider can move out of the first position towards the second position as this movement is now unblocked. The blocking member may be arranged between the slider and the housing such that the blocking member prevents the movement of the slider when the blocking member is in the blocked position. The blocking member may be moveable by the active drive, for instance by the same active drive configured to move the slider from the first to the second position. The use of an active drive may ensure control of the movement of the blocking member and subsequent control of the movement of the slider. The active drive may therefore enable a separation between unblocking of the blocking member and movement of the slider by the active drive.

The active drive of the needle insertion mechanism may include a rotatable cam shaft that may be in a bearing engagement with the housing, and the cam shaft may be configured to drive a gear rack that is part of, or coupled to the slider.

The rotatable cam shaft may be in a bearing engagement with the housing, for instance with a passage in the housing.

The bearing engagement may act as a barrier, for example a fluid or liquid tight barrier. Alternatively, the bearing may form a sterile barrier. The bearing may include a resilient member providing the barrier, which may additionally act as a shock absorber. As an example, the bearing engagement may include an O-ring between the rotatable cam shaft and a passage in the housing that may be configured to receive the O-ring. Optionally, the O-ring may be lubricated to improve the sealing and reduce friction. The gear rack may be unitarily formed with the slider or the gear rack is coupled to the slider as a separate part. The separate part may be moveable mounted to the slider such that relative translation in one direction is allowed whereas in a direction angulated or perpendicular to that translation direction, force may be transferred from the gear rack to the slider. Alternatively the separate part including the gear rack may be rotatably mounted to the slider.

The gear rack of the needle insertion mechanism may form the blocking member and the gear rack may be pivot-mounted to the slider and rotation of the cam shaft tilts the gear rack from a tilted position to an untilted position.

The pivot mounted gear rack of the needle insertion mechanism may be biased towards the tilted position, such as by an elastic member positioned between the housing and the gear rack. The elastic member may be an elastic part, a spring member, a flexible member or a flexible arm. The pivot mounted gear rack may have a flexible arm that is biased towards the housing or a housing part such as a mechanic holder. The flexible arm may be integrated with the gear rack. Alternatively the pivot mounted gear rack may include a spring such as a torsional spring or a compression spring which biases the gear rack towards the tilted position. The biasing member may also be present on or part of the housing or housing part.

Biasing the pivot mounted gear rack towards the tilted position may bias the blocking member into the blocked position. Additionally, the pivot mounted gear rack that is biased into the tilted position may be beneficial during assembly of the device as the gear rack is in a stable position and does not move due to, for example, gravitational forces acting on the gear rack. The pivot mounted gear rack may include a passage or a cut-out that is not aligned with, or abuts, a complementary protrusion on the housing when the gear rack is in the tilted position thereby blocking movement of the slider out of the first position. When the pivot mounted gear rack is in the untilted position, the passage is aligned with the complementary protrusion, or the abutment between the cut-out and the complementary protrusion is released, thereby allowing relative movement between the passage or cut-out and the protrusion and thus unblocking movement of the slider from the first to the second slider position.

The complementary protrusion of the housing may abut a cutout in the slider or a part of the slider that surrounds the passage. Once moved to the untilted position by the active drive, the complementary protrusion may be released from the abutment with the gear rack and the pivot mounted gear rack forming the blocking member unblocks the relative movement between the protrusion and the gear rack and therewith also the relative movement of the slider with respect to the protrusion and thus allowing movement of the slider with respect to the housing. Alternatively, once moved to the untilted position by the active drive, the complementary protrusion can move relative to, and through, the passage in the gear rack such that the gear rack is enabled to move relative to the protrusion and thereby unblocking the movement of the slider out of the first position. Once the gear rack is in the unblocked or untilted position, the slider can be moved by the active drive.

The gear rack may include gear teeth engaging a gear wheel that is part of or coupled to the cam shaft.

The gear teeth on the cam shaft may form a gearing engagement with the gear rack such that rotation of the cam shaft may be transferred into movement of the gear rack and this movement can be related to unblocking or releasing the slider and/or the subsequent movement of the slider itself. The gear teeth on the gear rack may be a continuous set of teeth arranged on an axis. Optionally, the set of teeth may be divided into several sections and the teeth in each section may be arranged on a different axis.

A first section of the gear teeth of the needle insertion mechanism may be arranged parallel to the needle axis and a second section of the gear teeth may be arranged transverse to the needle axis where one of the first or second sections of the gear teeth enable the movement of the gear rack from the tilted to the untilted position and the other one of the first or second sections of the gear teeth enable movement of the slider from the first slider position to the second slider position.

Rotation of the cam shaft over a first angle may engage the first section of the gear teeth of the gear rack thereby rotating or translating the gear rack with respect to the slider and optionally with respect to the complementary protrusion. Rotation of the cam shaft over the second angle may engage the second section of the gear teeth of the gear rack and may enable load transfer from the gear rack to the slider for moving the slider out of the first position. The first and second sections may be connected to each other forming a continuous set of gear teeth. There may be a hold (no rotation of the cam shaft) between the rotation over the first and second angles or, alternatively, there may be a continuous rotation over the sum of the first and second angles. After rotation over the sum of the first and second angles the needle insertion mechanism may first be activated as described above and further rotation of the cam shaft may activate the needle retraction mechanism.

The pivot mounted gear rack of the needle insertion mechanism may include at least one protrusion engaging a bore in the slider allowing for the pivot movement and at least one second protrusion engaging a guide track in the slider and/or the housing forming a motion-link system.

The guide track for the second protrusion may be only in the slider or optionally in the slider and the housing.

The first protrusion may allow for rotation and force transfer from the pivot mounted gear rack to the slider, the second protrusion may control the rotation and may contribute to the load transfer as well. The guide track for the second protrusion may include two sections angulated to another, both sections may be linear, alternatively one section may be circular allowing for the rotary movement and the second section may be linear. For the guide track in the slider, the end of the linear section of the guide track may, once the second protrusions abuts the end, contribute to the force transfer from the pivot mounted gear rack to the slider. The first protrusion engaging the bore in the slider may have a certain play for allowing the second protrusion to enter the second section. Thus once the first and second protrusions respectively abut the bore and the end of the second section, effective transfer of the load from the gear rack, which is driven by the gear teeth of the gear wheel of the cam shaft, may be established.

For the guide track in the housing, the second section of the guide track allows for free movement of the second protrusion on the slider. The guide track in the slider may include only the first circular section for the second protrusion when there is a guide track in the housing and the slider. Force may be transmitted from the gear rack to the slider via the first and second protrusions as the second protrusion moves through the second section of the guide track in the housing as the second protrusion of the gear rack is free to move in the housing or housing part.

The second protrusion of the needle insertion mechanism may be guided by the motion-link system between the gear rack and the slider which may prevent the gear rack from returning back to the tilted position once the slider has moved out of the first position.

Once moved into the second section of the guide track, the second protrusion may, for example due to an angle between the first and second sections, be prevented or at least hindered from moving back from the second section to the first section. This may increase the reliability of the device or re-use of a once-use only device.

In some implementations of the needle insertion device, a part of the housing may be arranged between the slider and the gear rack.

The pivot mounted gear rack may be arranged between the slider and the housing part, or alternatively, the housing may be arranged between the slider and the pivot mounted gear rack. For the latter case, passages and guide tracks may be required in the housing for the first and second protrusions penetrating from the pivot mounted gear rack through the housing and subsequently engaging the bore and guide track in the slider. The passage and guide track in the housing may have dimensions at least equal to the dimensions of the bore and guide track in the slider. For instance, the dimensions of the passage in the housing and the guide track in the housing may allow for the relative movement of the slider with respect to the housing from the first to the second slider position without hindering movement of the slider and the gear rack. The protrusions extending from the gear rack may be oriented perpendicular to the direction of the gear teeth of the gear rack and for instance may be liner protrusions. The guide track in the slider may therefore be arranged flush with the guide track in the housing when the slider is in the first slider position.

In another embodiment, the blocking member may be part of the rotatable cam shaft.

The blocking member of the needle insertion mechanism may be configured as a protrusion extending from the cam shaft and being part of a second motion-link system between the cam shaft and the slider.

The protrusion may be unitarily formed with the cam shaft and for instance may extend from the gear wheel towards the slider. The protrusion and/or the gear wheel may be constructed from a high strength material such as a fiber reinforced material (a carbon fiber or glass fiber reinforced polymer such as PEEK, polyamide and the like). Alternatively, the protrusion may be constructed from a metal such as titanium or stainless steel. For example, a metal pin may be inserted, attached, adhered or glued into a polymeric gear wheel.

The second-link motion system of the needle insertion mechanism may be formed by a groove in the slider engaging the protrusion extending from the cam shaft. The link motion system may prevent relative movement between the protrusion and the slider and may thereby block movement of the slider.

The groove may include a first section engaging the protrusion retaining the protrusion on the cam shaft and the slider in a form fit engagement. As the cam shaft is in a bearing engagement with the housing, the load from the slider (for example an impact load on the device) may be guided from the slider to the link motion system to the bearing and finally to the housing thereby preventing movement of the slider.

The groove of the needle insertion mechanism may include a second section connected to the first section and the second section may allow for relative movement between the slider and the protrusion and rotation of the cam shaft may move the protrusion from the first section to the second section. Once in the second section, relative movement between the cam shaft and the slider may be permitted, such as lateral movement of the slider from first to the second slider position. The first section of the groove may be linear, whereas the second section may be curved allowing for rotational movement of the cam shaft as the protrusion moves through the groove. Release or unblocking of the slider can be achieved by rotation of the cam shaft in one direction only for moving the protrusion from the first to the second section, or alternatively the cam shaft is first rotated in one direction for release and in the second direction for slider movement. In the latter case the gear wheel of the cam shaft may lack one or more teeth such that the rotation of the cam shaft is used for moving the protrusion for the first to the second section in the groove without load transfer from the gear wheel to the gear teeth on the gear rack, thus decoupling the unblocking of the slider from the subsequent slider movement.

In another embodiment the blocking member may be configured as a protrusion extending from the cam shaft abutting a ratchet member of the active drive.

The ratchet member of the needle insertion mechanism may be shaped as a hollow cylinder having a passage in the side wall and rotation of the gear wheel may align the passage in the side wall and the protrusion of the cam shaft. Before alignment, the protrusion may abut the ratchet member of the active drive and the ratchet member may be directly or indirectly coupled to the cam shaft such that rotation of the cam shaft is prevented. An impact force on the slider may therefore, due to the gearing engagement with the cam shaft, not result in a shift of the slider. In other words, the slider may be prevented from moving out of the first position as this may result in a rotation of the cam shaft which is prevented by the engagement between the protrusion and the ratchet member.

An injection device including the needle insertion mechanism provided herein may result in the blocking member preventing unintentional activation of the needle insertion mechanism when exposed to a drop test according to EN ISO 11608-1:2015 or a drop test from a height of 1 meter onto a drop surface selected from a concrete floor or wood having a density >600 kg/m3.

The needle insertion mechanism or the injection device including the needle insertion mechanism may be subjected to impact forces during transport and use, forces generated during a drop may shift the slider and release the operative coupling between the slider and the needle holder resulting in unintentional needle insertion and needle sticking by the patient. The blocking member arranged between the slider and the housing which blocks the movement of the slider from the first to the second position may therefore improve the safety and reliability of the insertion mechanism or the injection device. This may be tested using the drop test according to the specific ASTM, DIN IEC or ISO standards. Such tests may require that the device including the needle insertion mechanism is dropped from a standardized height on a standardized surface with different orientations for the device. Such a drop test may be repeated, for instance three times, using the same device and each time a different orientation is selected. The different orientations are selected to define a worst case scenario for the needle insertion mechanism, for instance along the axis of the slider movement. A drop test in the present disclosure is thus not related to a single device and a single drop test but includes a plurality of devices. The outcome of the test in terms of pass or fail correlates to the ensemble of devices tested and is statistically evaluated. For example at least 10 devices are tested each at three different orientations, or at least 50 devices are tested, or 200 or more devices are tested and the failure rate is below 5%, or below 1% (repeated) drop testing, for example 5 of a plurality of test devices, for example at least 10 devices, or at least 50 devices, or 200 or more devices, the failure rate may be below 5%, or below 1%, for example. Drop tests according to IEC 60601-1:2005 Chapter 15.3.4.1 or EN ISO 11608-1:2015 are described in more detail above.

The needle insertion mechanisms presented above may be integrated into an injection device. The injection device may be a patch injection device including an external housing having a bottom surface with a skin adhesive layer where the slider moves parallel to the bottom surface when moving from the first to the second slider position and where the needle holder is moveable perpendicular to bottom surface.

BRIEF DESCRIPTION OF THE DRAWINGS

The subject matter of the present disclosure will be explained in more detail in the following text with reference to the embodiments which are illustrated in the attached drawings, in which:

FIGS. 40a-40d: A needle insertion mechanism with a blocking member according to a first embodiment: Pivot mounted gear rack in the untilted position and slider moved towards the second slider position.

DETAILED DESCRIPTION

Definitions

The term "medicament" or "medication" includes any flowable medical formulation suitable for controlled administration through a means such as, for example, a cannula or a hollow needle and includes a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

A needle is defined as a hollow needle or cannula capable for fluid transmission. The needle may be constructed from a metal such as stainless steel, or alternatively from a plastic. The needle has at least one sharp needle tip configured to penetrate the skin of the patient and/or the septum or sealing of a reservoir or cartridge holding the medicament.

The distal end or distal direction is defined by the direction of the needle configured to penetrate the skin of the patient. For an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

DESCRIPTION OF THE FIGURES

Referring to FIGS. 1 to 19 an embodiment of a needle insertion and retraction module 2 including a needle insertion and retraction mechanism 3 is disclosed without a releasable coupling or blocking arrangement between a slider (control element 40) and a housing (first or second housing 11, 12, respectively).

Figure 1:
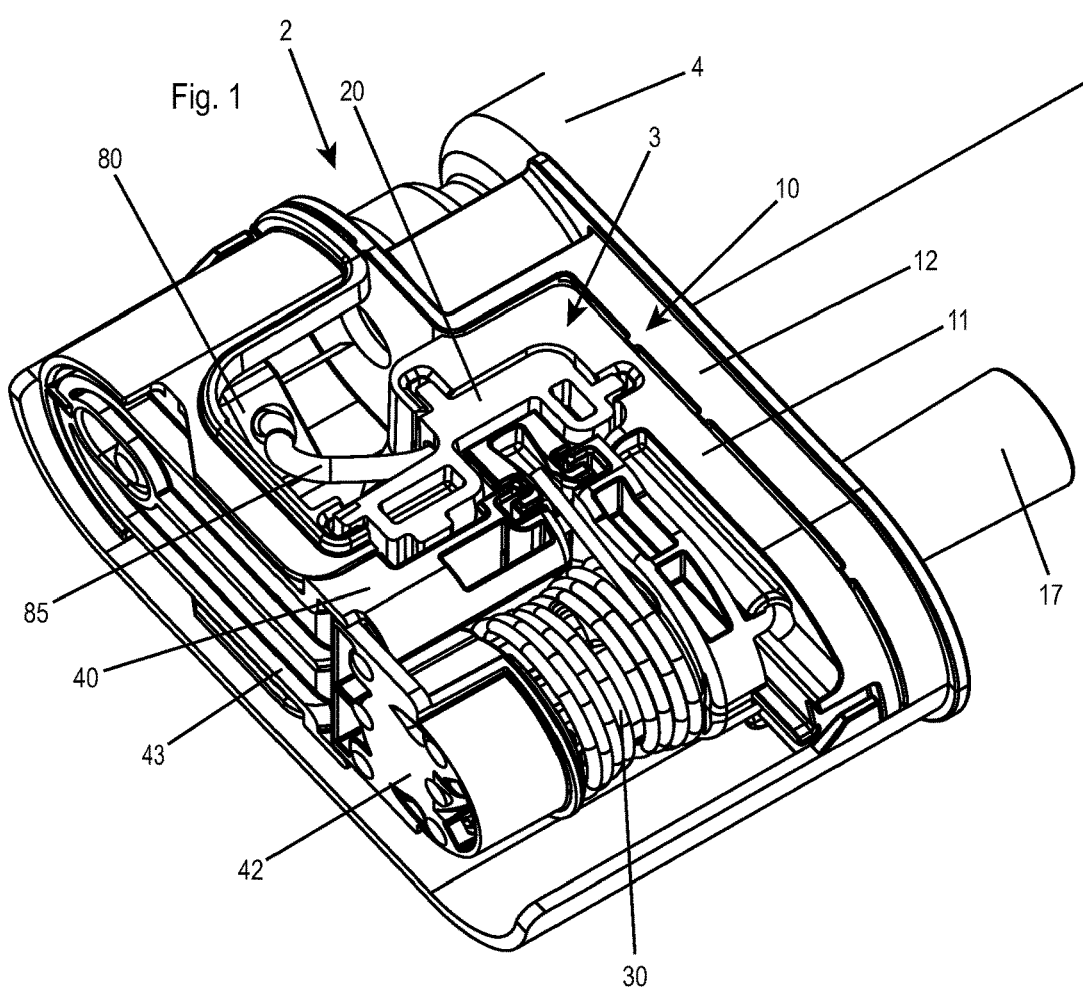
FIG. 1: a perspective view of a needle insertion and retraction module including a needle insertion and retraction mechanism.

As displayed in FIG. 1 the needle insertion and retraction mechanism 3 includes a housing 10 which is a multiple component housing. The housing 10 may include a first housing 11 and a second housing 12 which are connected to each other by positive fit or by firmly bonding or welding. Alternatively the first and the second housings 11, 12 are molded as a single part.

Figure 2:
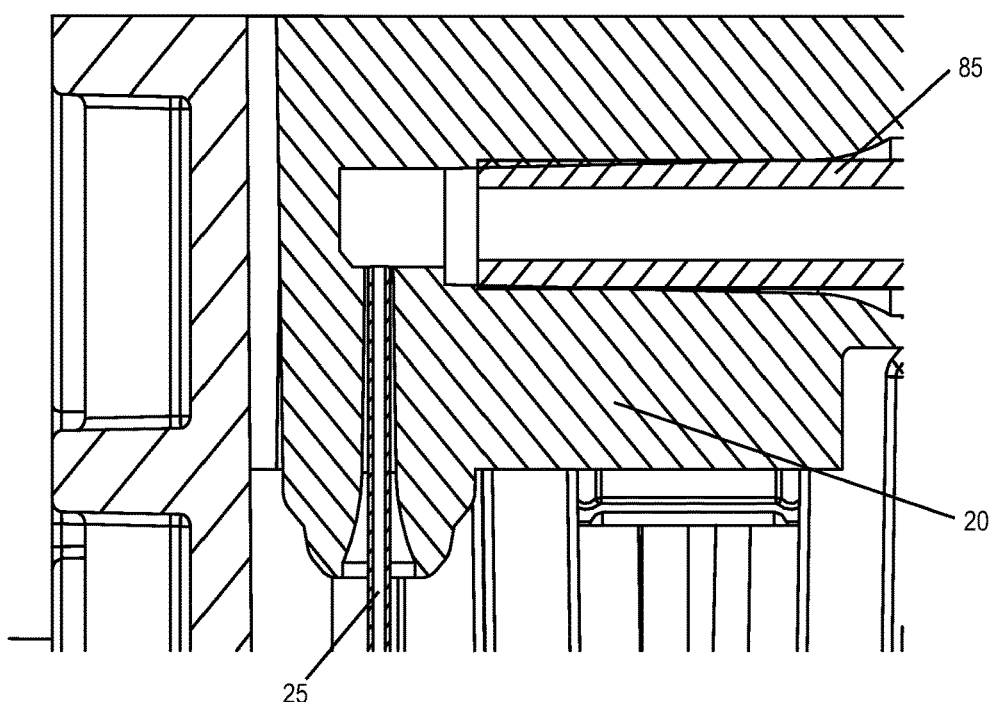
FIG. 2: a cross-sectional view through a needle carrier.

The needle insertion and retraction mechanism 3 includes a needle carrier 20 which holds a needle 25 (FIG. 2) and which is linearly guided by the housing 10, for instance by the first housing 11. The housing 10 or the first housing 11 includes a longitudinal guide (FIG. 1) which engages the needle carrier 20 such that it is movable along the longitudinal axis of the needle 25. The longitudinal guide includes at least a first longitudinal groove and a second longitudinal groove formed by the housing 11. The needle carrier 20 includes at least a first rib and a second rib where the first rib engages the first groove and the second rib engages the second groove. Thereby the needle carrier 20 is linearly guided to be moved along the longitudinal axis of the needle 25. The needle carrier 20 is movable between an initial position (FIG. 1) in which the needle 25 which protrudes from the needle carrier 20 in a needle insertion direction is completely encompassed by the housing, and a needle insertion position (FIGS. 6 and 7) in which the needle protrudes from an outer surface of the housing, and for instance protrudes into or is placed onto the surface which is intended to be contacted or adhered to the skin of a patient. The housing 10 may include an opening or a pierceable wall through which the needle 25 is moved when the needle carrier 20 is moved from its initial position to its needle insertion position. The longitudinal axis of the needle 25 is substantially perpendicular or normal with respect to the surface which is intended to be inserted or adhered to the skin of the patient. The needle 25 is a hollow needle through which a medication or a medicament can be injected into the patient and may thus be referred to as a skin needle, a hollow needle, or an insertion needle. The housing 10, such as the housing 12 is adapted to retain a product container 4. In the example shown, the product container 4 is a carpule, with a pierceable septum 5 (wall) at its forward end. The medicament of the product container 4 can be expelled through a flexible tube 85 which is in fluid communication with the hollow needle 25 and through the needle 25 in a patient. As can be seen in FIG. 2 the needle carrier 20 includes a channel which connects an end of the flexible tube 85 and the hollow needle 25 in a fluid guiding manner. The needle 25 is fixedly retained in a bore of the needle carrier 20. The flexible tube 85 is with one end fixedly retained in a bore of the needle carrier 20.

The other end of the flexible tube 85 is fixedly retained in a bore of a spike carrier 80 which connects a hollow spike 70 in a fluid guiding manner with the flexible tube 85, by means of a channel formed by the spike carrier 80. The spike 70 is fixedly retained in a bore of the spike carrier 80. One end of the flexible tube 85 is fixedly retained in a bore of the spike carrier 80.

The needle insertion and retraction mechanism 3 further includes a first spring member 31 which is adapted to move the needle carrier 20 with respect to the housing 10 in a needle insertion direction along the longitudinal axis of the needle 25. Furthermore, a second spring member 32 is provided which is adapted to retract the needle carrier 20 with respect to the housing 10 in a needle retraction direction, which is opposed to the needle insertion direction. In the embodiment shown, the first spring member 31 and the second spring member 32 are integrally formed by one spring 30. However, in an alternative, spring members 31 and 32 can be separate from one another.

Figures 7, 8:
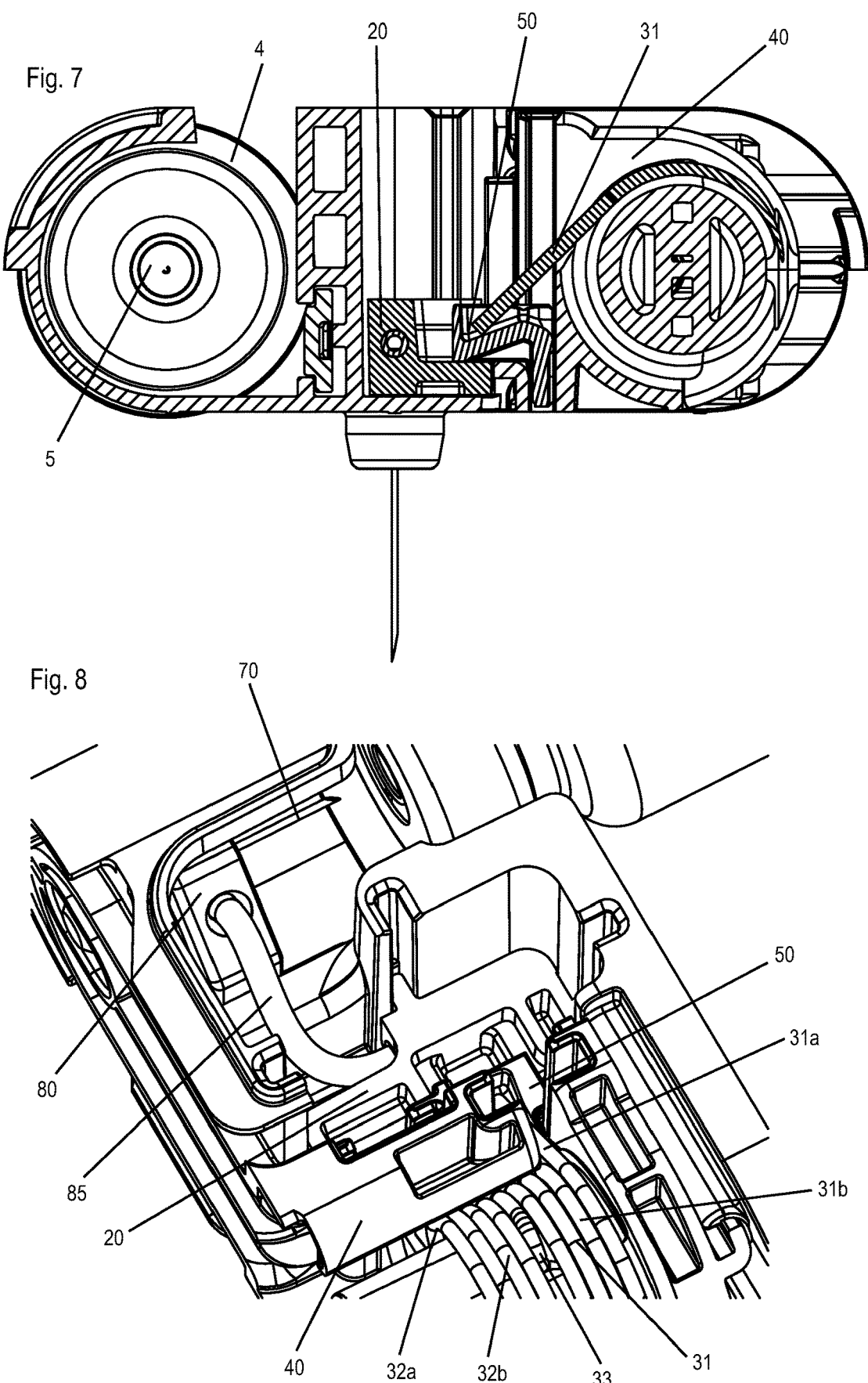
FIG. 7: a further view of the needle carrier in a needle insertion position.
FIG. 8: a spike carrier with a spike in a first position.

The first spring member 31 includes a first helical spring section 31b which operates as a torsion spring (FIG. 8). A first arm 31a protrudes from the circumference of the first helical spring section 31b. The first spring member 31 is supported on a control element 40 such that the first helical spring section 31b can be strained or tensioned by pivoting the arm 31a. Furthermore, the energy stored in the first helical spring section 31b can be released where the first arm 31a is pivoted in a direction which causes the needle carrier 20 to move in the needle insertion direction.

The second spring member 32 (FIG. 13) includes a second helical spring section 32b which operates as a torsion spring. A second arm 32a protrudes from circumference of the second helical spring section 32b. The second spring member 32 is supported on the control element 40 such that the second helical spring section 32b can be strained or tensioned by pivoting the arm 32a. Furthermore, the energy stored in the second helical spring section 32b can be released where the second arm 32a is pivoted.

The first helical spring section 31b and the second helical spring section 32b surround a portion of the control element 40. This portion includes a slit which retains an interconnecting section 33 of the spring 30 which interconnects the first helical spring section 31b and the second helical spring section 32b and which also provides the support section of the first spring member 31 and the second spring member 32 for tensioning the spring sections 31a and 31b. In embodiments with two separate spring members 31 and 32 each of them can include a supporting section by which the spring member 31, 32 is supported on the control element 40.

Figure 17:
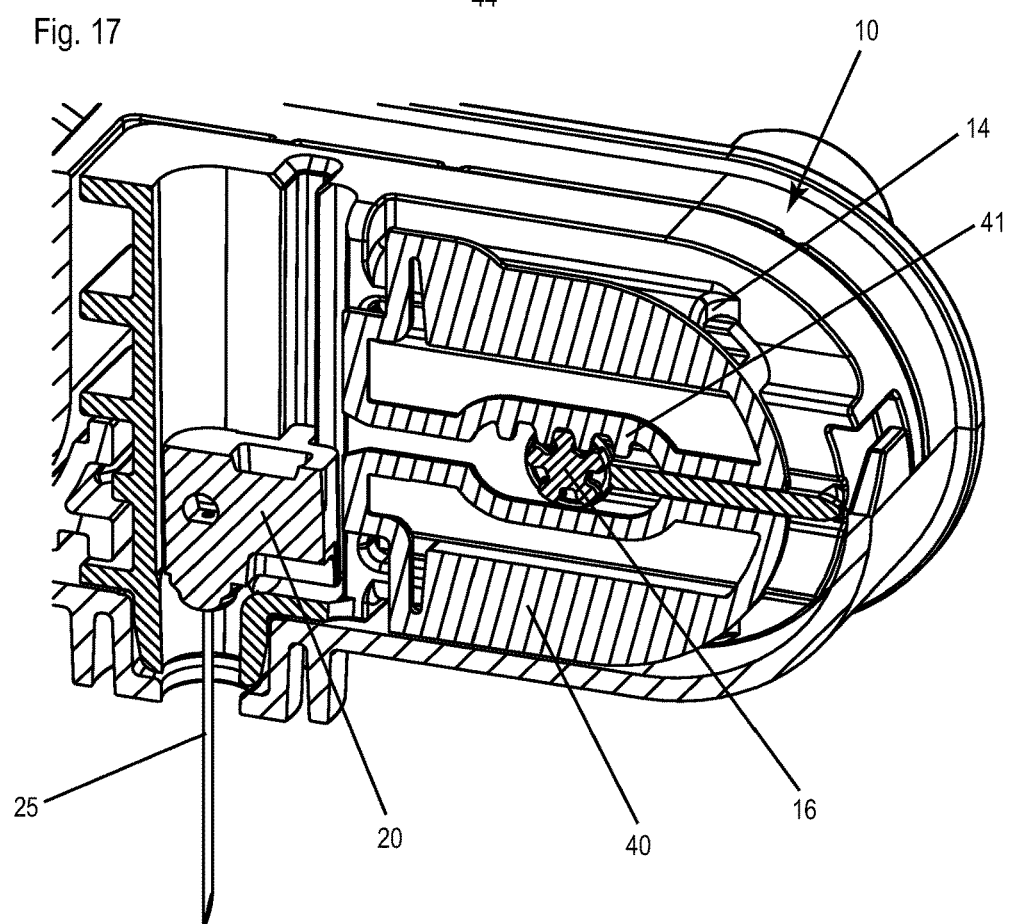
FIG. 17: a control element which has been moved in the needle release position.
Figure 18:
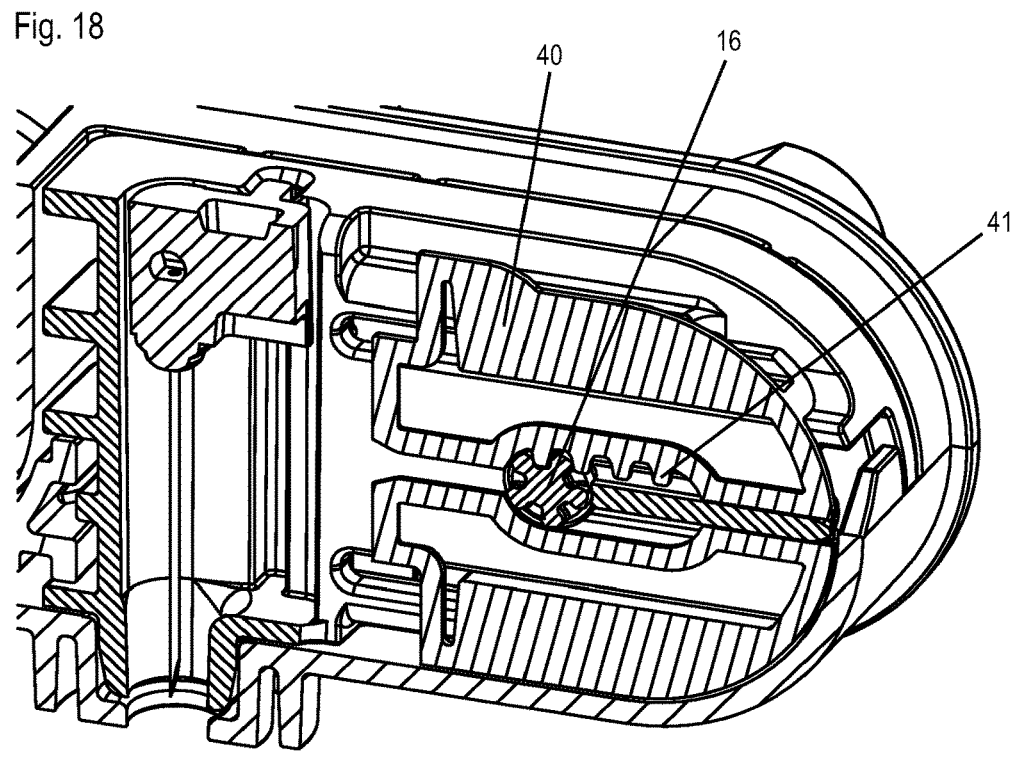
FIG. 18: the control element which has been moved in its needle retraction position.
Figure 19:
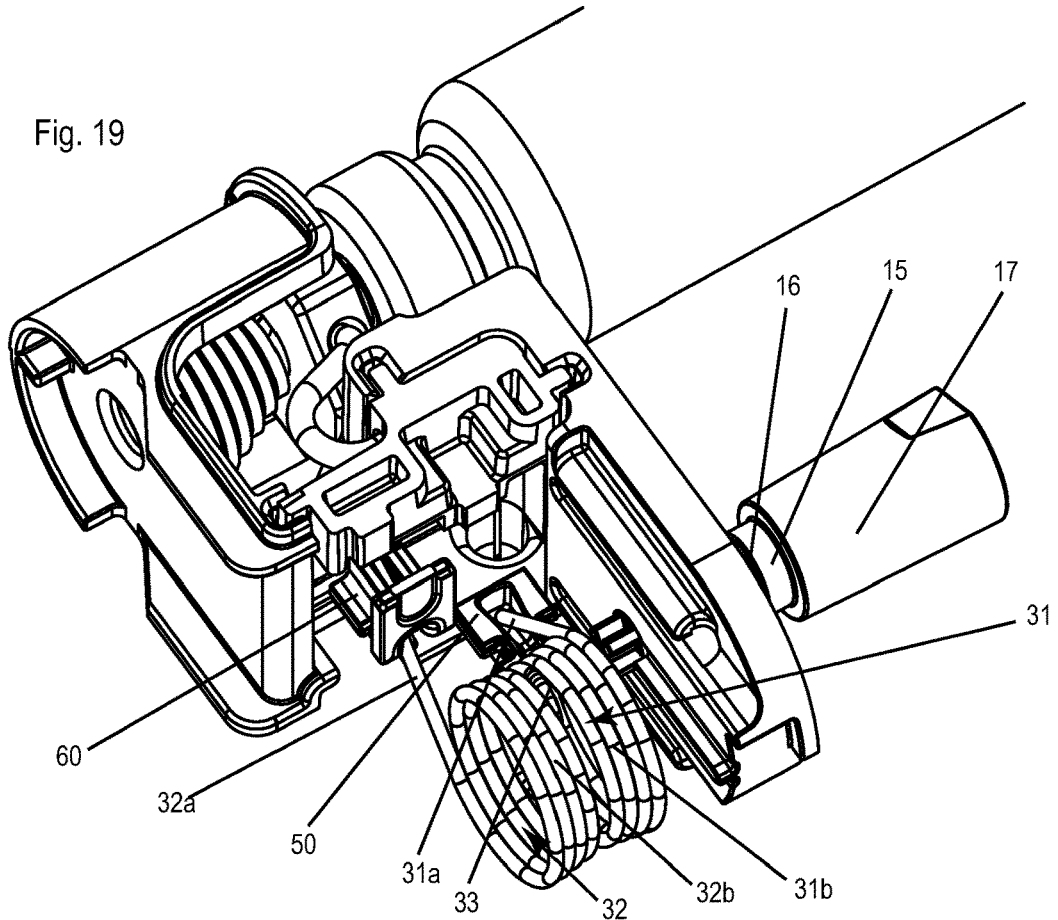
FIG. 19: a spring for moving the needle carrier in the needle insertion direction and in the needle retraction direction.

A control element 40, being an example of a slider, is linearly guided with respect to the housing 10 to be moved transversely with respect to the longitudinal axis of the needle 25. The control element 40 can be moved from a first position or starting position (FIG. 16) to a second position or needle insertion release position (FIG. 17). The slider may be moved to a third position, a so-called needle retraction release position (FIG. 18). The control element 40 moves from the starting position to the needle retraction release position, including the positions between the starting position and the needle retraction release position, in the same direction. The spring 30 or the spring members 31, 32 are attached to the control element 40 such that they move together with the control element 40 (slider). The needle insertion and retraction mechanism 3 or module 2 provides for a drive shaft 15 which is rotatably guided by the housing 10, for instance by virtue of a rotational bearing (FIG. 19). The drive shaft 15 is operatively connected to the control element 40. The drive shaft 15 and the control element 40 are adapted to cooperate with each other such that rotation of the drive shaft 15 in a first rotational direction causes the control element 40 to be linearly moved, namely transversely with respect to the longitudinal axis of the needle 25 because of the linear guide provided by the housing 10.

The drive shaft 15 includes a gear wheel 16 (FIGS. 16 to 18) which is formed by or connected to the drive shaft 15 and which engages a gear rack 41 formed by or connected to the control element 40. By rotating the drive shaft 15 or the gear wheel 16 the control element 40 is linearly moved.

The drive shaft 15 includes a coupling member 17 which is adapted to be coupled with a coupling member of a drive shaft of a drive mechanism. Thereby, rotation of the drive shaft 15 of the drive mechanism in a first direction is transmitted to the drive shaft 15 in the first direction causing the control element 40 to be moved in the first longitudinal direction. The drive shaft 15 is rotated by an active drive, either directly or via a gearing arrangement that may include a worm wheel.

Figures 3, 4:
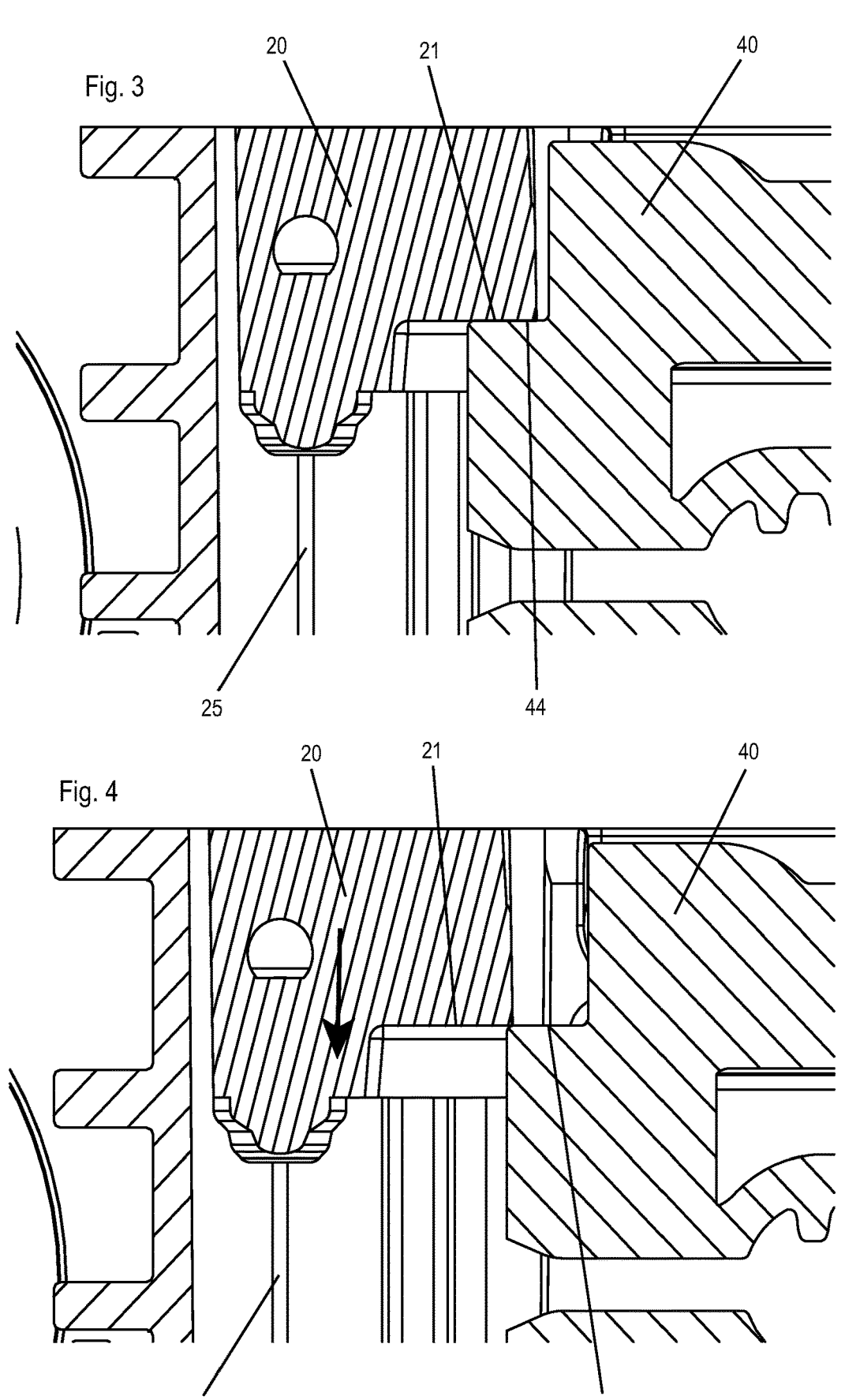
FIG. 3: a control element which is engaged with the needle carrier.
FIG. 4: the control element disengaging the needle carrier.
Figure 5:
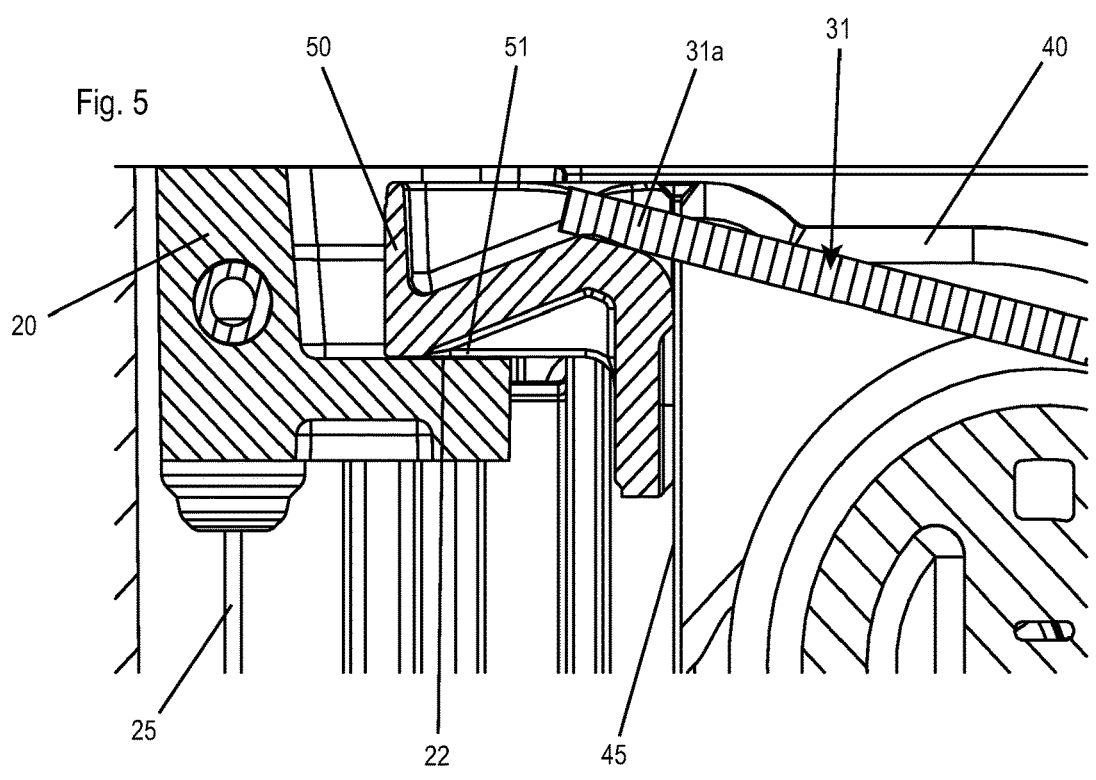
FIG. 5: a first intermediate member between a spring arm and a needle carrier with the needle carrier in a retracted position.
Figure 6:
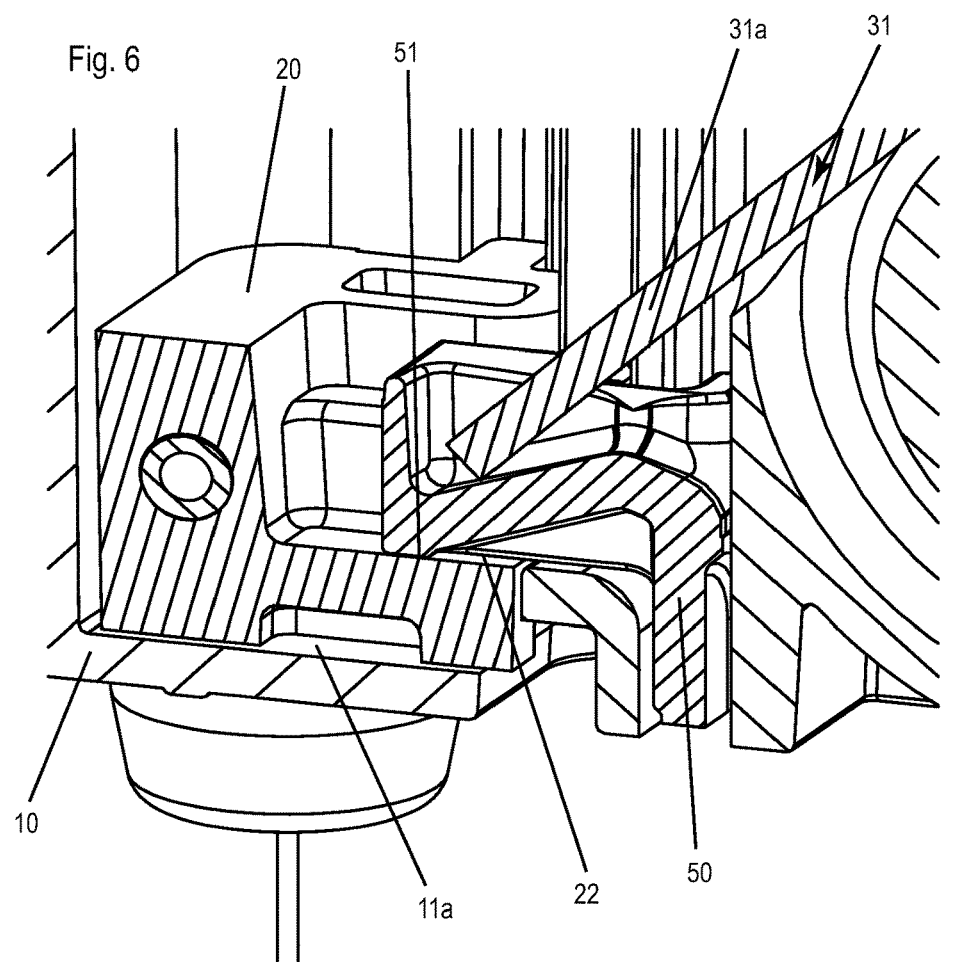
FIG. 6: the parts of FIG. 5 with the needle carrier in a needle insertion position.

The control element 40 includes a cap 42 which is connected to a main body 43 of the control element 40 (FIG. 1). The cap 42 is connected to or partially fits over the portion which is surrounded by the helical spring sections 31b, 32b. The cap 42 keeps the spring 30 or the spring members 31, 32 in position on the control element 40 or the main body 43 (FIG. 1). The control element 40 is operatively coupled to the needle carrier 20 to prevent the needle carrier 20 from being moved in the needle insertion direction when the control element 40 is in its starting position (FIG. 3). As can be seen in FIG. 3, the control element 40 or its main body 43 includes a stop surface 44 on which a counter stop surface 21 of the needle carrier 20 rests when the control element 40 is in its starting position. The needle carrier 20 is thereby prevented from being moved in the needle insertion direction. As can be seen in FIG. 4, the stop surface 44 disengages the counter stop surface 21 when the control element 40 is moved in its insertion release position such that the needle carrier 20 is free to be moved in the needle insertion direction. The first arm 31a or more generally the spring member 31 operates on the needle carrier 20 via a first intermediate member 50 (FIG. 5) to drive the needle carrier 20 form the initial position (FIG. 5) in the needle insertion direction into a needle insertion position (FIG. 6).

A first intermediate member 50 includes a counter stop surface 51 which engages a stop surface 22 of the needle carrier 20 when the control element 40 (or slider) is in its starting (or first) position and/or in its insertion release position. The first spring member 31 applies a spring force on the first intermediate member 50 which in turn transmits the spring force to the needle carrier 20 as long as the first intermediate member 50 and the needle carrier 20 are in engagement. A spring powered movement of the needle carrier 20 in the needle insertion direction, when the control element 40 is in its starting position, is prevented when stop surface 44 and counter stop surface 21 are engaged (FIG. 3). Once the control element or slider moves out of, or has moved a certain distance out of, the starting position, the control element 40 and the needle carrier 20 are disengaged and the first spring member 31 drives the needle carrier 20 in the needle insertion direction into the needle insertion position until the needle carrier 20 abuts an axial stop IIa provided by the housing 10, such as by the first housing 11. The control element 40 includes a linear guide 45 which is adapted to linearly guide the first intermediate member 50 in the direction of the longitudinal axis of the needle 25 or the needle insertion and retraction direction (FIG. 5). The linear guide 45 causes the first intermediate member 50 to be moved together with the control element 40 transversely with respect to the longitudinal axis of the needle from the starting position via at least the needle insertion release position to the needle retraction release position. By moving the control element 40 (or slider) from its starting position (first slider position) to its needle insertion release position (second slider position) the first intermediate member 50 is moved with respect to the needle carrier 20 but does not yet disengage from the needle carrier 20. That is to say that the first intermediate member 50 and the needle carrier 20 remain engaged in the needle insertion release position of the control element 40.

Figure 12:
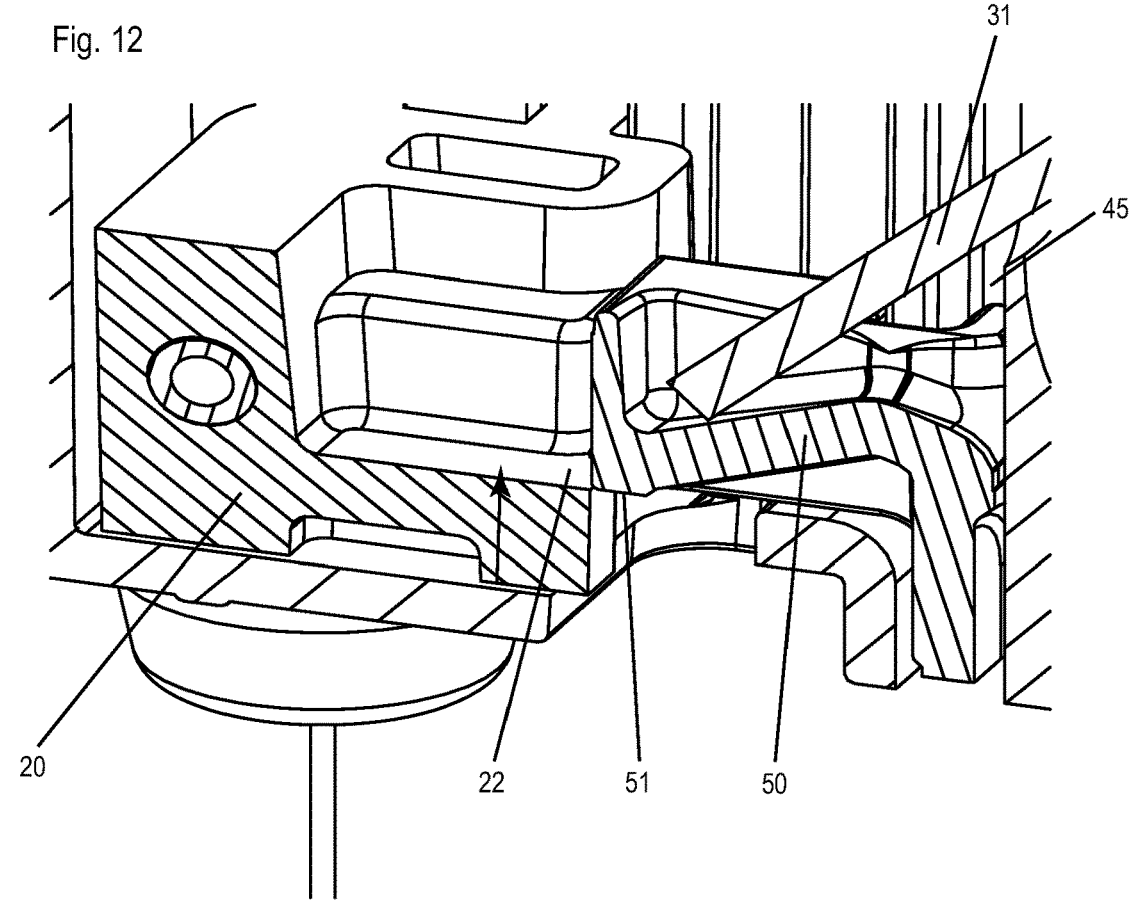
FIG. 12: the first intermediate member disengaged from the needle carrier.

When the control element 40 is moved further from the second slider position by activating the rack and pinion arrangement to its retraction release position (third slider position), the second spring member 32 is operatively coupled to the needle carrier 20 such that the second spring member 32 drives the needle carrier 20 in the needle retraction direction. By moving the control member 40 into the needle retraction release position, the first intermediate member 50 and the needle carrier 20, such as the stop surface 22 and the counter stop surface 51, disengage since the first intermediate member 50 is moved together with the control element 40 transversely with respect to the longitudinal axis of the needle 25. The needle carrier 20 is now free to be moved in the needle retraction direction which is opposed to the needle insertion direction (FIG. 12).

For example, when the first intermediate member 50 is disengaged from the needle carrier 20, it—driven by the remainder of the spring force of the first spring member 31—abuts a stop formed by the control element 40, such as by the end of the linear guide 45. Thereby, the remainder of the spring force of the first spring member 31 may be prevented from interfering with the further operation of the mechanism.

A second intermediate member 60 (FIG. 13) is provided, which is linearly guided by the control element 40 in the needle retraction direction, for instance by a linear guide 46 provided by the control element 40. The linear guide 46 is adapted that the second intermediate member 60 is linearly movable with respect to the control element 40 along the longitudinal axis of the needle 25 or in the needle retraction direction. Furthermore, the linear guide 46 causes the second intermediate member 60 to be moved together with the control element 40 transversely with respect to the needle retraction direction or transversely with respect to the longitudinal axis of the needle 25.

Figure 13:
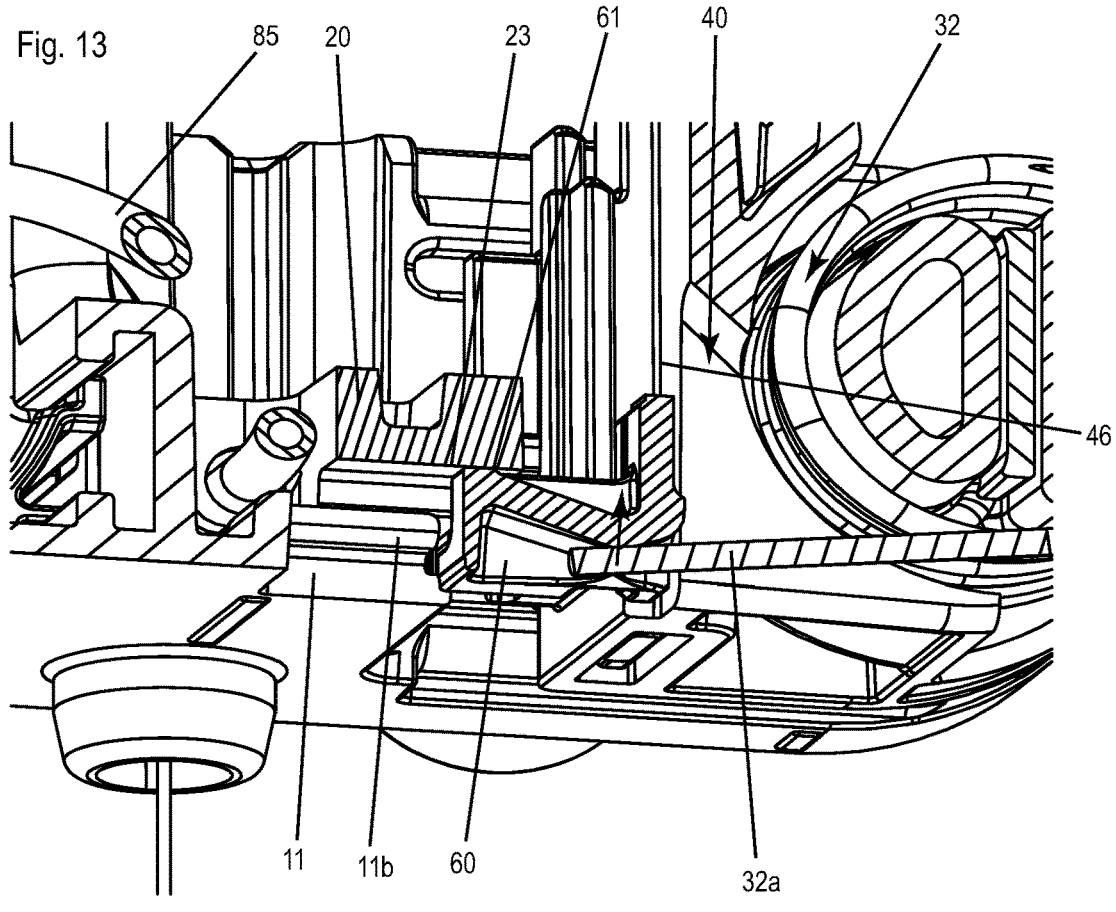
FIG. 13: a second intermediate member between a second spring arm and the needle carrier, where the intermediate member is disengaged from the housing and engaged with the needle carrier.
Figure 14:
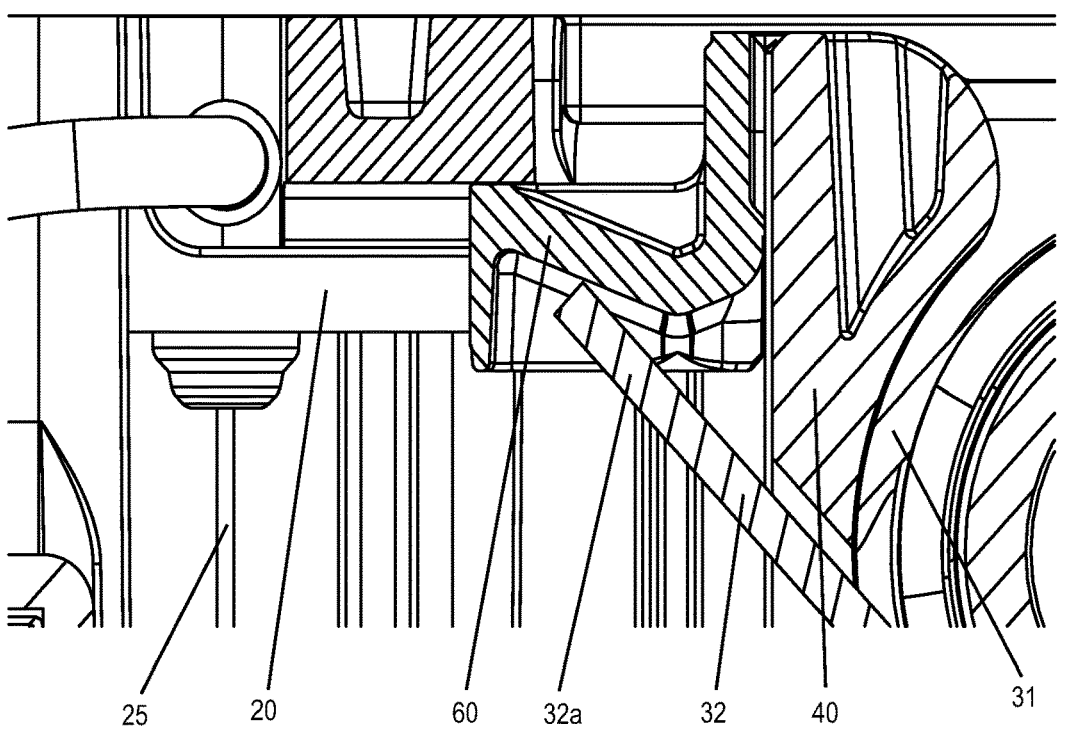
FIG. 14: the needle carrier which has been moved in the retracted position.
Figure 15:
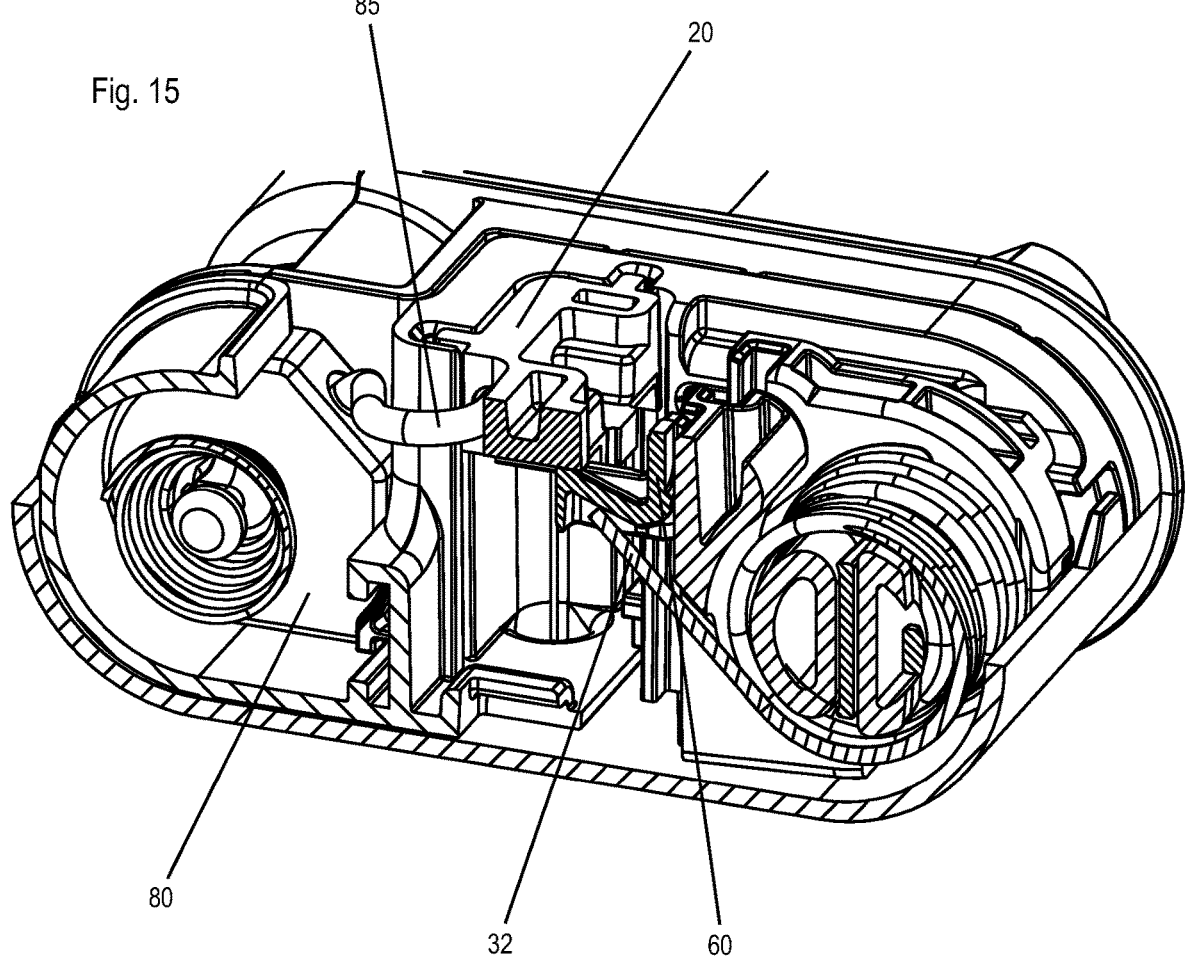
FIG. 15: a perspective view of the needle carrier which has been moved in the retracted position.
Figure 16:
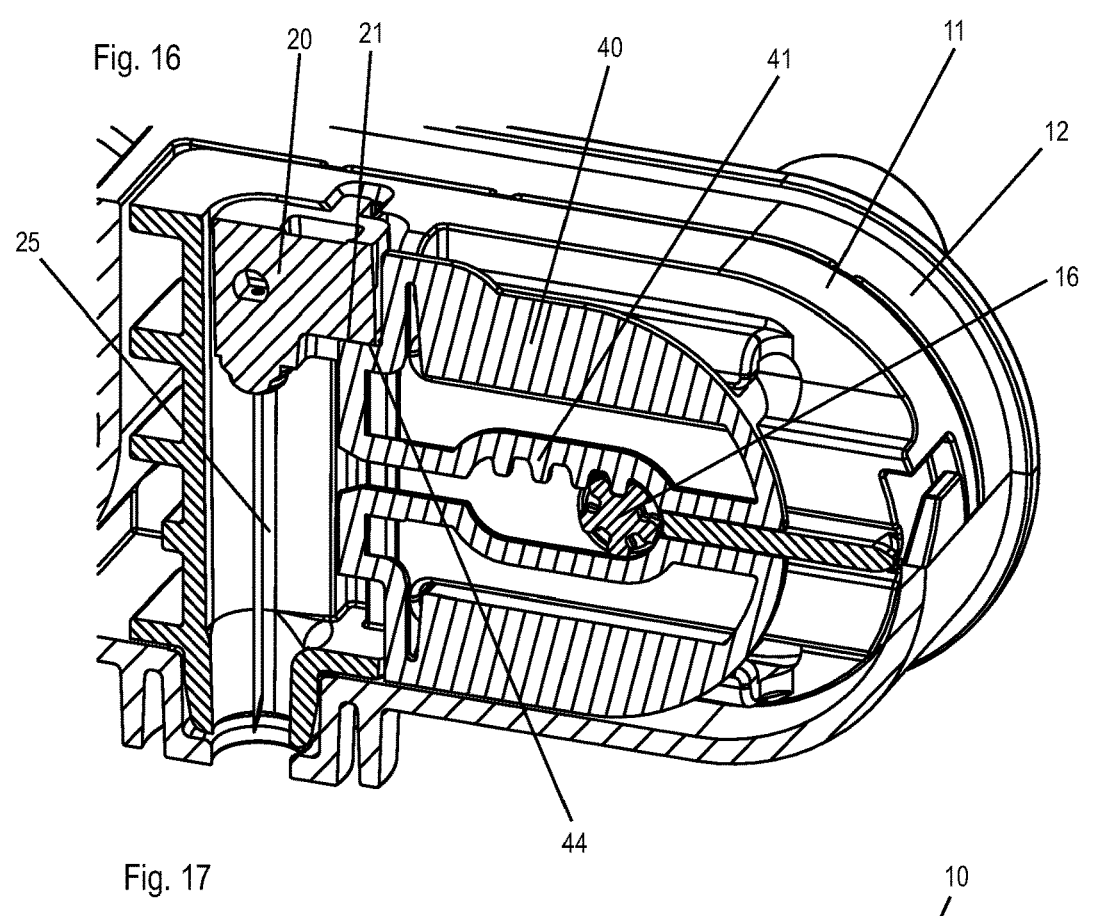
FIG. 16: a control element in its starting position.

When the control element 40 is in its starting position (first slider position) and/or in its insertion release position (second slider position), the second intermediate member 60 it is engaged with the housing 10, such as the housing 11, such that the second intermediate member 60 is prevented from being moved in the needle retraction direction (FIG. 13). The housing 10 includes a stop surface 11b with which the second intermediate member 60 is engaged to prevent the second intermediate member 60 from being moved in the needle retraction direction. The second spring member 32 applies a spring force on the second intermediate member 60 in the needle retraction direction. By moving the control element 40 in its retraction release position the second intermediate member 60 is disengaged from the housing 10, such as from the stop surface 11b. Furthermore, the second intermediate member 60 or a counter stop surface 61 thereof engages with the needle carrier 20 or a stop surface 23 thereof. Thereby, the second intermediate member 60 and the needle carrier 20 are moved in the needle retraction direction driven by the second spring member 32 (FIG. 13). Thereby the needle carrier 20 is moved in its retracted position such that the needle 25 is completely retracted into the housing 10 (FIGS. 14 and 15).

To prevent the first intermediate member 50 and the second intermediate member 60 from interfering with each other they are positioned axially offset from one another such as in the direction which is transversal with respect to the longitudinal axis of the needle 25 (FIG. 19). The first intermediate member 50 and the second intermediate member 60 may be offset from each other in the direction of the longitudinal axis of a needle spike 70.

The first spring arm 31a rests on a convexly curved contact surface of the first intermediate member 50 as can be seen in FIG. 5. During the first intermediate member 50 is driven by the first spring member 31 in the needle insertion direction, the spring arm 31a, such as its circumference surface, moves over the apex of the convexly curved contact surface, thereby the first arm 31a (or its circumference surface) may slide and/or roll over the convexly curved contact surface. This arrangement reduces friction and/or reduces the risk of malfunction with respect to other arrangements.

Movement of the needle carrier 20 in the needle retraction direction is prevented at least by the remainder of the spring force of the first spring member 31 operating on the first intermediate member 50 as long as the first intermediate member 50 is engaged with the needle carrier 20 (FIG. 6).

Furthermore, as shown in FIG. 6, the free end of the first spring arm 31a includes an edge, for example, formed between the circumference surface and the end face of the first spring arm 31a. When the needle carrier 20 is in its needle insertion position, the edge contacts or rests on, for instance—to a small or microscopic extent—grooves into, the first intermediate member 50, for instance on an inclined surface thereof. The edge contacting or even grooving into the first intermediate member 50 increases friction between the first intermediate member 50 and the first spring arm 31a. Thereby, movement of the needle carrier 20 in the needle retraction direction is—in addition to the remainder of the spring force of the first spring member 31—made more difficult or even prevented as long as the first intermediate member 50 is engaged with the needle carrier 20. The angle between the inclined surface and the circumference surface may, for example, be smaller than the angle between the end face and the circumference surface.

The second spring arm 32a rests on a convexly curved contact surface of the second intermediate member 60 as can be seen in FIGS. 13 and 14. While the second intermediate member 60 is driven by the second spring member 32 in the needle retraction direction, the spring arm 32a moves over the apex of the convexly curved contact surface thereby the second arm 32a may slide and/or roll over the convexly curved contact surface. This arrangement reduces friction and/or reduces the risk of malfunction with respect to other arrangements.

Movement of the needle carrier 20 back in the needle insertion direction is prevented at least by the remainder of the spring force of the second spring member 32 operating on the second intermediate member 60 as long as the second intermediate member 60 is engaged with the needle carrier 20 (FIG. 14).

Furthermore, as shown in FIG. 14, the free end of the second spring arm 32a includes an edge, for example, formed between the circumference surface and the end face of the second spring arm 32a. When the needle carrier 20 is in its needle retraction position, the edge contacts or rests on, such as—to a small or microscopic extent—grooves into, the second intermediate member 60, for instance on an inclined surface thereof. The edge contacting or even grooving into the second intermediate member 60 increases friction between the second intermediate member 60 and the second spring arm 32a. Thereby, movement of the needle carrier 20 back in the needle insertion direction is—in addition to the remainder of the spring force of the second spring member 32—made more difficult or even prevented as long as the second intermediate member 60 is engaged with the needle carrier 20. The angle between the inclined surface and the circumference surface may, for example, be smaller than the angle between the end face and the circumference surface.

Figure 9:
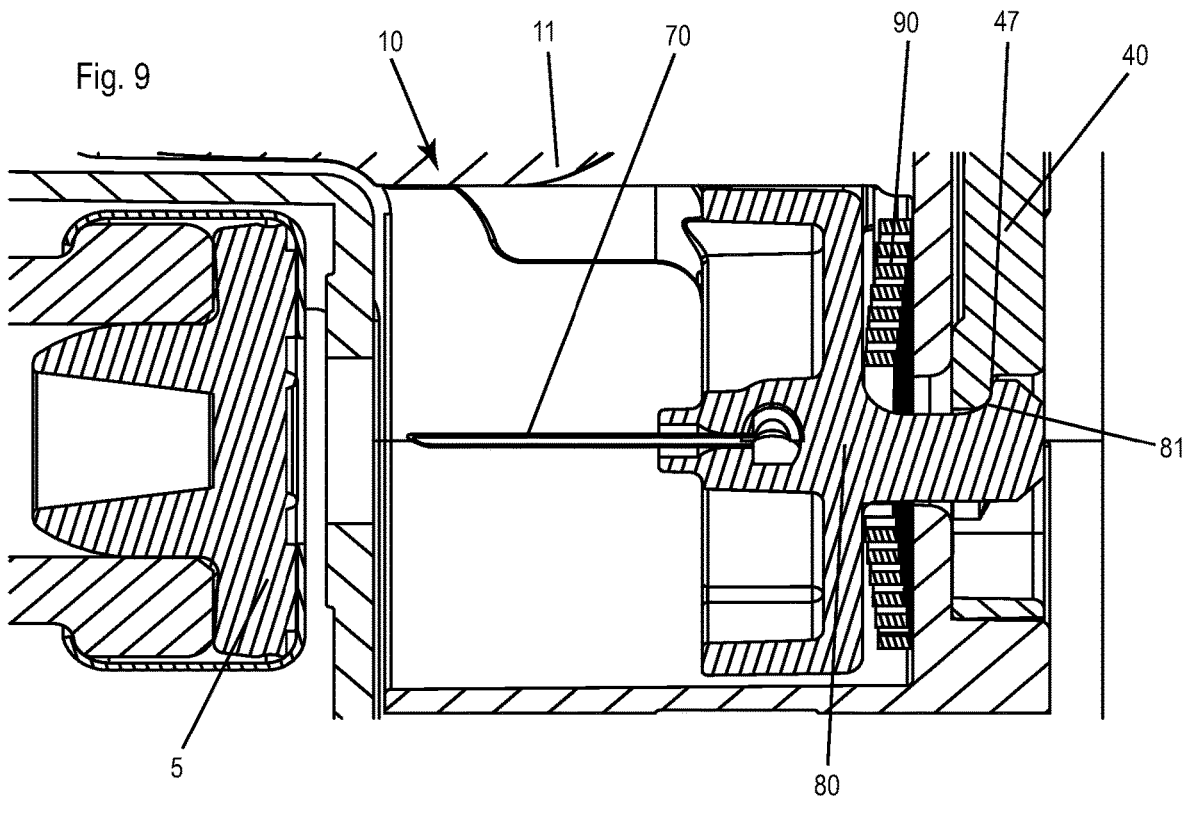
FIG. 9: a cross-sectional view of the spike carrier in a first position.
Figure 10:
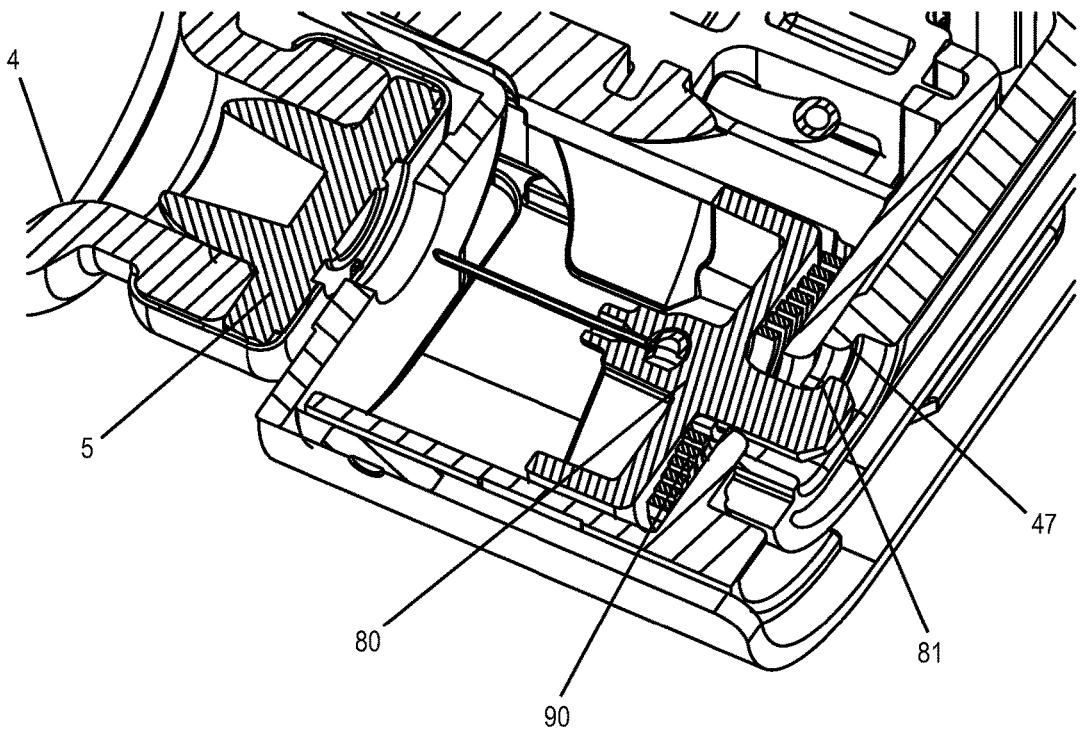
FIG. 10: a cross-sectional view of the spike carrier being released to be moved in a second position.

The spike carrier 80 holds a hollow spike 70 which protrudes from the spike carrier 80 to a receptacle for the product container or to a pierceable wall 5 of the product container, when the product container is inserted in the receptacle (FIGS. 8 to 11). In FIGS. 9 and 10 the spike carrier 80 is in a first position in which the spike 70 does not pierce the wall 5 of the product container 4. The spike carrier 80 is linearly guided, for instance by a linear guide provided by the housing 10, such as by the housing 11, such that the spike carrier 80 can be moved linearly from a first position to a second position together with the spike 70. By moving the spike carrier 80 from the first position to the second position the spike 70 pierces the wall 5 of the product container 4 such that the spike 70 establishes a fluid communication between the medication inside the product container 4 and the needle 25. A spring 90 is provided, which operates on the spike carrier 80 to drive the spike carrier 80 from the first position to the second position. In the first position of the spike carrier 80 the spring 90 is in a pre-tensioned condition. A variety of spring configurations may be conceivable, such as a conical helical spring 90. One end of the spring 90 is supported on the spike carrier 80 and the other end of the spring 90 is supported on the housing 10, such as the housing 11.

Figure 11:
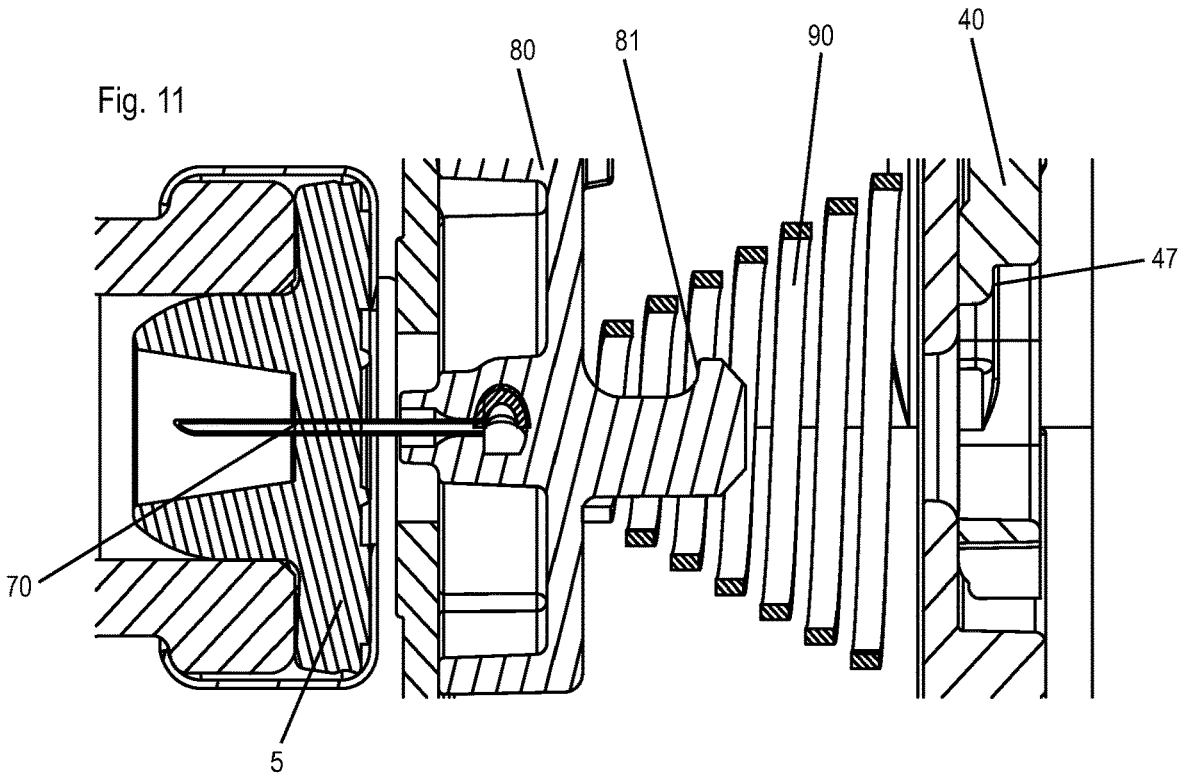
FIG. 11: a cross-sectional view of the spike carrier in a second direction.

The control element 40 is engaged with the spike carrier 80, when the control element 40 is in its starting position. Thereby, the spike carrier 80 is retained in its first position and the spring 90 is prevented from expanding. For instance, the control element 40 includes a retaining surface 47 which engages a counter surface 81 to prevent the spike carrier 80 from being moved from the first position to the second position. By moving the control element 40 from its starting position (first slider position) in the first direction, for instance the direction to the injection release position the control element 40 is disengaged from the spike carrier 80, the retaining surface 47 may disengage from the counter surface 81 such that the spike carrier 80 is free to be moved from the first position to the second position (FIG. 10). The spring 90 expands and thereby drives the spike carrier 80 from the first position into the second position (FIG. 11). The needle insertion and retraction mechanism can be adapted such that the spike carrier 80 is released before, after or at the same time the needle carrier 20 is released to be moved in the needle insertion direction.

The spike carrier 80 includes a main body which holds the spike 70 and which is linearly guided by the housing 10. The spike may be a hollow steel needle or constructed from a suitable plastic material. A hollow steel needle may be attached, adhered or glued into the spike carrier 80. The spike carrier 80 includes a protrusion which protrudes from the main body opposite to the direction in which the spike 70 protrudes. The protrusion extends through the (conical) helical spring 90, through a section of the housing 10. The section of the housing 10 can be arranged between the section of the control element 40 which includes the retaining surface 47, and the spike carrier 80. The protrusion includes the counter surface 81.

Referring to FIGS. 20 to 37 embodiments of a needle insertion and retraction module including a needle insertion and retraction mechanism 3 are disclosed with a releasable coupling arrangement between the slider (control element 40) and the housing (10,11,12).

Figures 20, 21:
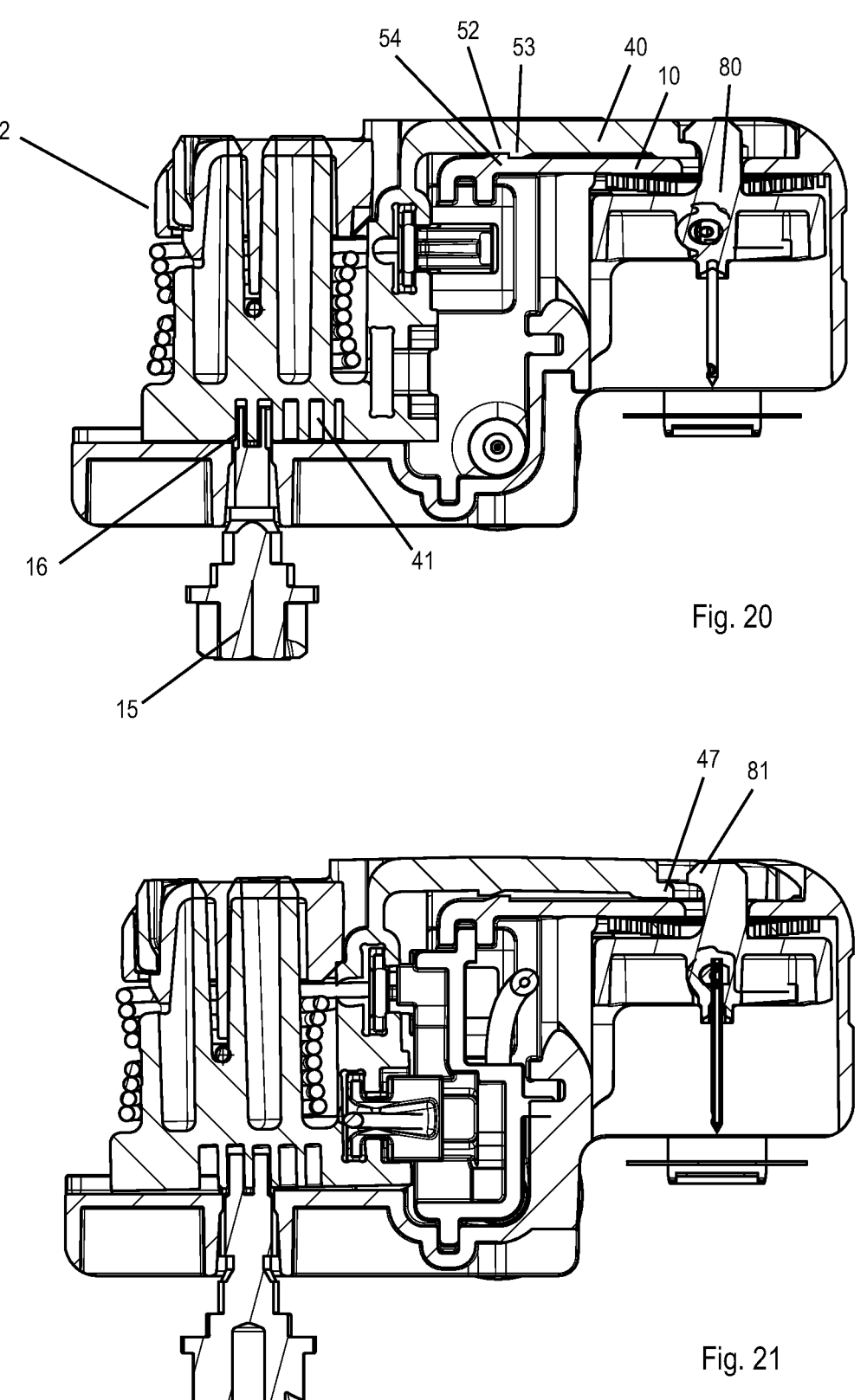
FIGS. 20, 21: Top view of a needle insertion mechanism with a releasable coupling arrangement according to a first embodiment.
Figures 22, 23, 24:
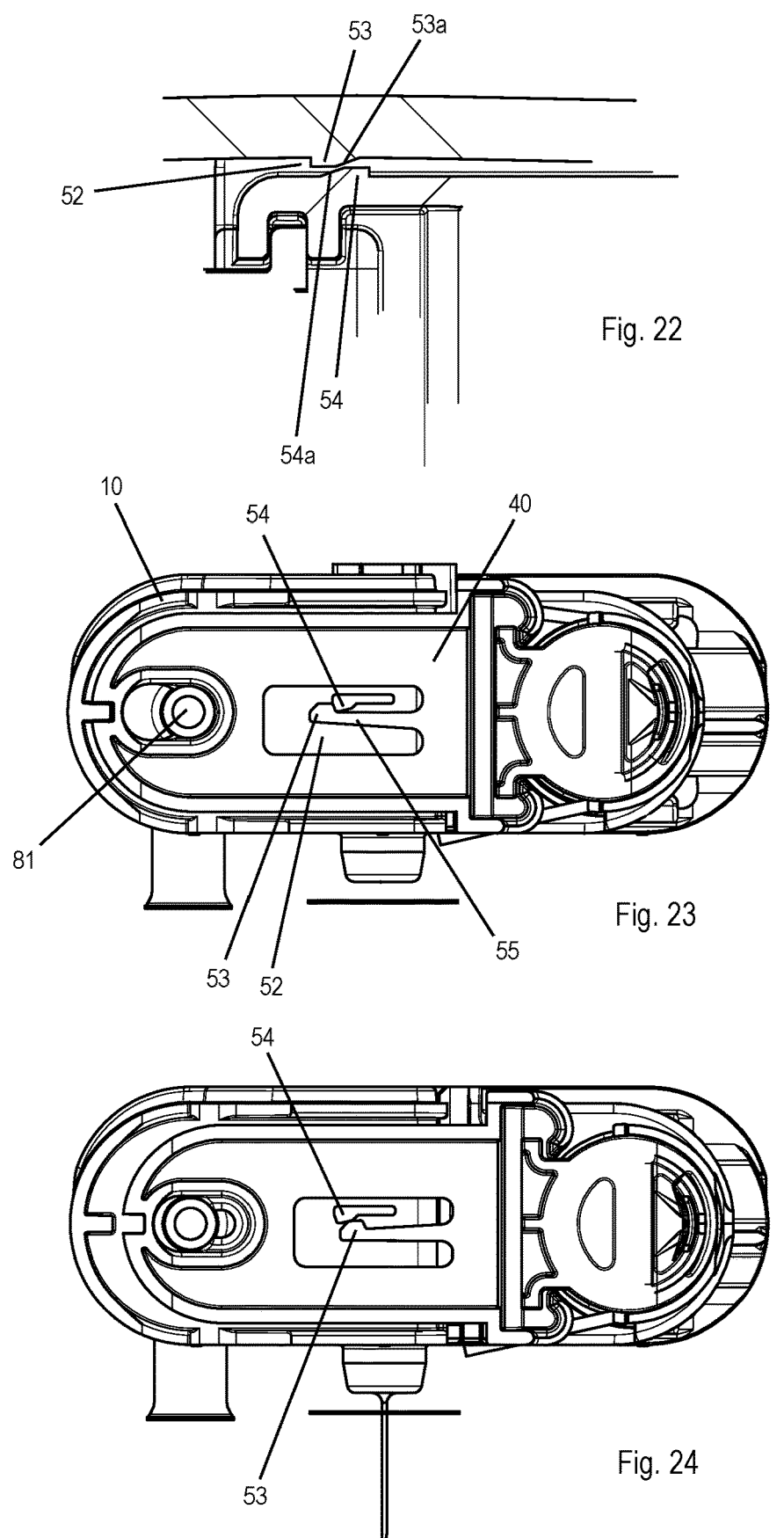
FIG. 22: Detail of the releasable coupling arrangement according to the first embodiment.
FIGS. 23, 24 and 25: Side view of a needle insertion mechanism with a releasable coupling arrangement according to a second embodiment.

FIGS. 20 to 22 show a first embodiment of a releasable coupling arrangement. In FIG. 20 a top view of the needle insertion and retraction module is shown with the releasable coupling arrangement 52 as the slider 40 is in the first slider position. The housing 10 includes a second coupling member 54 shaped as a protrusion with a sloped surface 54a (FIG. 22). The slider 40 includes a first coupling member 53 shaped as a protrusion with a sloped surface 53a (FIG. 22) that is complementary to and engaging the second sloped surface 54a when the slider 40 is in the first slider position. As provided herein, the coupling members 53, 54 are also referred to as protrusions 53, 54. The mutual engagement of the sloped surfaces 53a, 54a of the protrusions 53, 54 provide a releasable coupling arrangement. Upon activation of the device, the active drive rotates the cam shaft 15 with the gear wheel 16 engaging the gear rack 41 of the slider 40. When the slider 40 starts moving, the coupling arrangement 52 is released as the sloped surface 53a of the slider 40 moves over the sloped surface 54a of the housing. The protrusions 53, 54 on the slider 40 and/or the housing 10 are elastically deflected and/or plastically deformed when the slider 40 moves from the first slider position (FIG. 20) towards the second slider position (FIG. 21). The energy required for i) overcoming the friction between the surfaces 53a, 54a, and/or ii) elastically deforming the protrusions 53, 54 or the wall sections carrying the protrusions 53, 54, and/or plastically deforming one or both of the protrusions 53, 54 may provide the actuation threshold to be overcome before the slider 40 can move from the first slider position to the second slider position. When the slider is moved into the second slider position, the engagement between the retaining surface 47 on the slider 40 and the counter surface 81 of the spike carrier 80 may be released such that the hollow spike 70 of the spike carrier 80 moves towards the cartridge.

Alternatively, the mutual engagement of the non-sloped surfaces (that are oriented perpendicular to the surface of the slider and the housing), of the first and second coupling members 53, 54 are engaged and the sloped surfaces 53a, 54a facilitate the engagement of the non-sloped (or perpendicular) surfaces during assembly. The perpendicular oriented surfaces are adjacent to the sloped surfaces 53a, 54a and as the sloped surfaces slide over each other, the perpendicular surfaces may establish a form-fit engagement forming the coupling arrangement 52. The two perpendicular surfaces extend from a base surface on the housing 10 and slider 40. Movement of the slider 40 may require that either one of the two base surfaces for the coupling members 53, 54 on the slider 40 and housing 10 elastically deforms or that one or both coupling members 53, 54 with the perpendicular surfaces plastically deforms to allow for relative movement between the slider 40 and the housing 10.

In FIG. 20 the option is shown where the perpendicular surfaces of the coupling members 53, 54 are in a mutual engagement.

Figure 25:
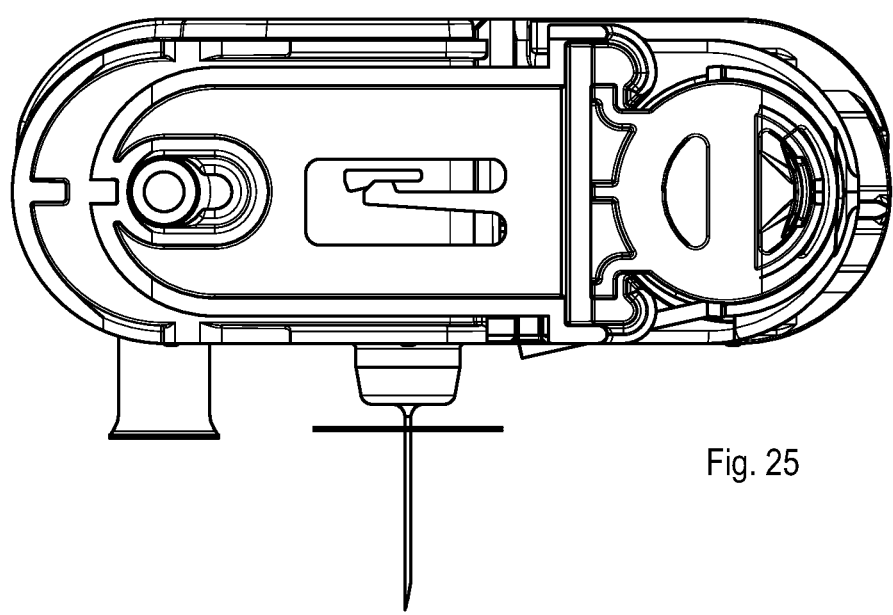

A side view for the releasable coupling arrangement according to a second embodiment is shown in FIGS. 23 to 25. The slider 40 is in the first position (FIG. 23) and the releasable coupling arrangement 52 is formed by the first coupling member 53 that is connected to the slider 40 via a flexible arm 55, together with the second coupling member 54, shaped as a protrusion on the housing 10, 11. When the slider 40 is moved towards the second slider position (FIG. 24), the arm 55 is flexed as the protrusions 53, 54 engage each other. The combination of friction and elastic deformation of the arm 55 provides for the actuation threshold to be overcome before the slider 40 can move with respect to the housing 10, 11 into the second slider position (FIG. 25).

Figure 26:
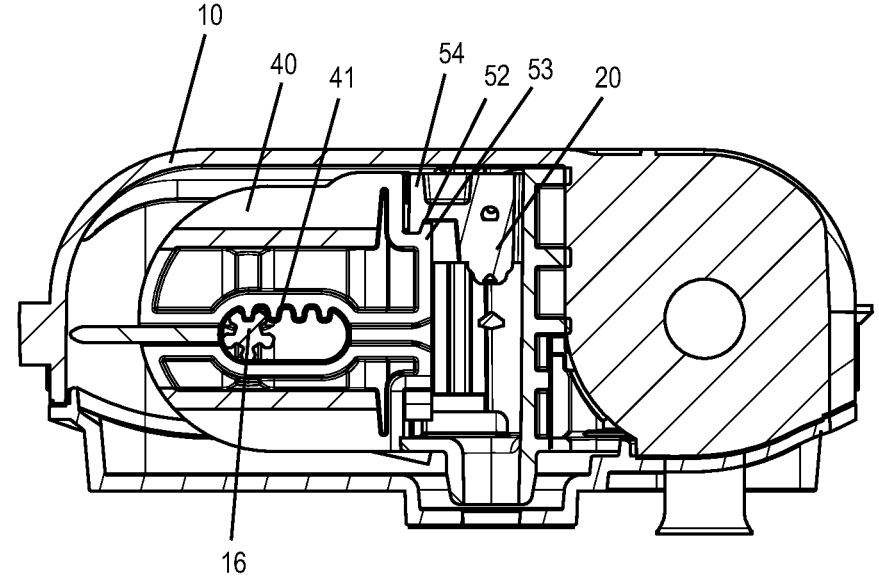
FIGS. 26, 26a, 27 and 28: Side view of a needle insertion mechanism with a releasable coupling arrangement according to a third embodiment.
Figure 26A:
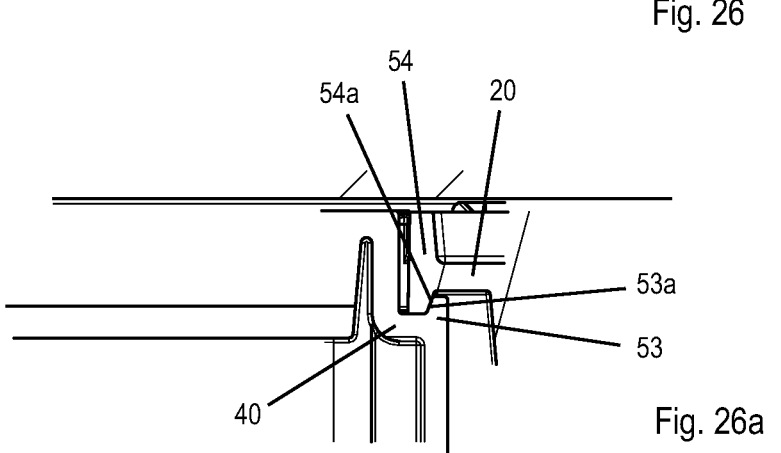
Figure 27:
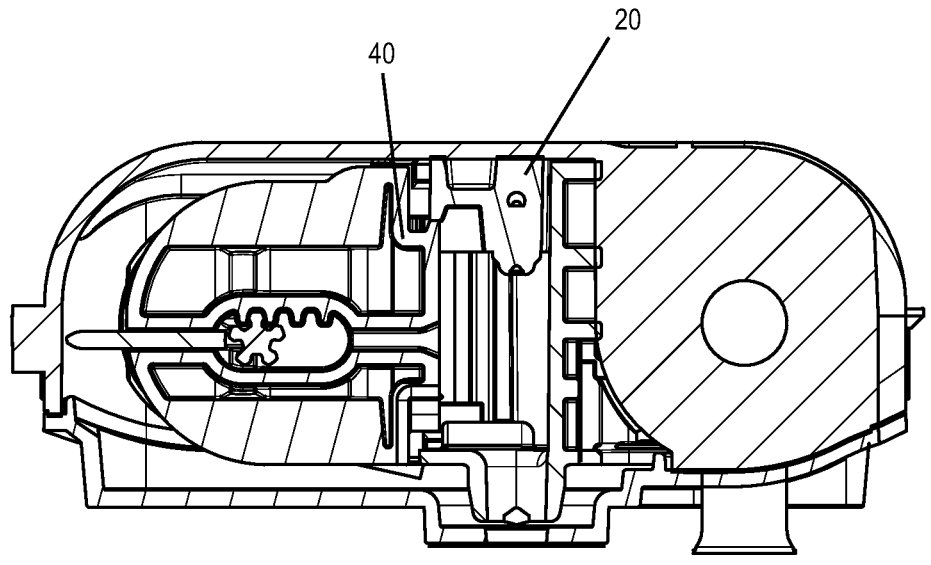
Figure 28:
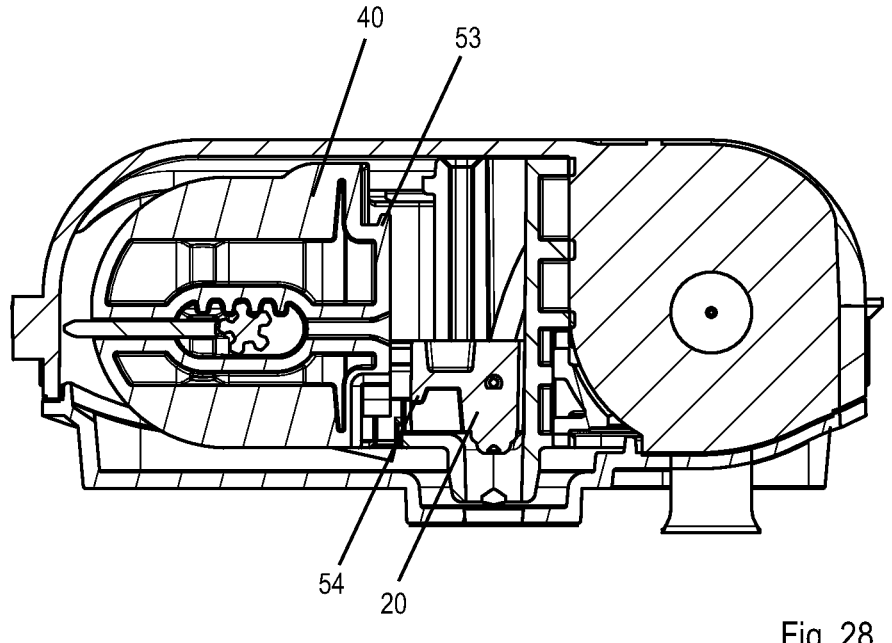

In FIGS. 26 to 28 the needle insertion and retraction module is shown according to a third embodiment for the releasable coupling arrangement and is essentially a further development of the arrangement presented in FIG. 3. The releasable coupling arrangement 52 is located between the needle holder 20 having the second coupling member 54 as a protrusion directed towards the insertion needle 25 and includes a sloped surface 54a. The releasable coupling arrangement 52 further includes a protrusion 53 on the slider 40 that is oriented along the insertion needle 25 and directed opposite to the protrusion 54 on the needle holder 20. Both protrusions 53, 54 have complementary sloped surfaces 53a, 54a that abut each other when the slider 40 is in the first slider position (FIGS. 26 and 26a). The needle holder 20 is biased by the first spring member 31 to move the needle holder 20 towards the needle insertion position (FIG. 28). The biasing force of the spring also biases the coupling members 53, 54 of the coupling arrangement 52 shown in FIGS. 26 to 28, and for instance the sloped surfaces 53a and 54a may be kept in abutment by the biasing force. When the slider 40 is moved towards the second slider position (FIG. 27), the protrusion 53 on the slider 40 moves relative to the non-moving protrusion 54 on the needle holder 20 and thereby either the sloped surfaces 53a, 54a slide over each other and/or one or both protrusions 53, 54 are deformed as the biasing force of the spring member 31 attempts to keep the surfaces into mutual abutment. Release of the coupling members 53, 54 may involve the needle holder 20 being moved against the needle insertion direction and against the bias of the spring force thereby providing the actuation threshold. The gearing engagement between the sloped surfaces 53a, 54a may, upon the desired slider movement, provide the energy to overcome this actuation threshold.

Figure 29:
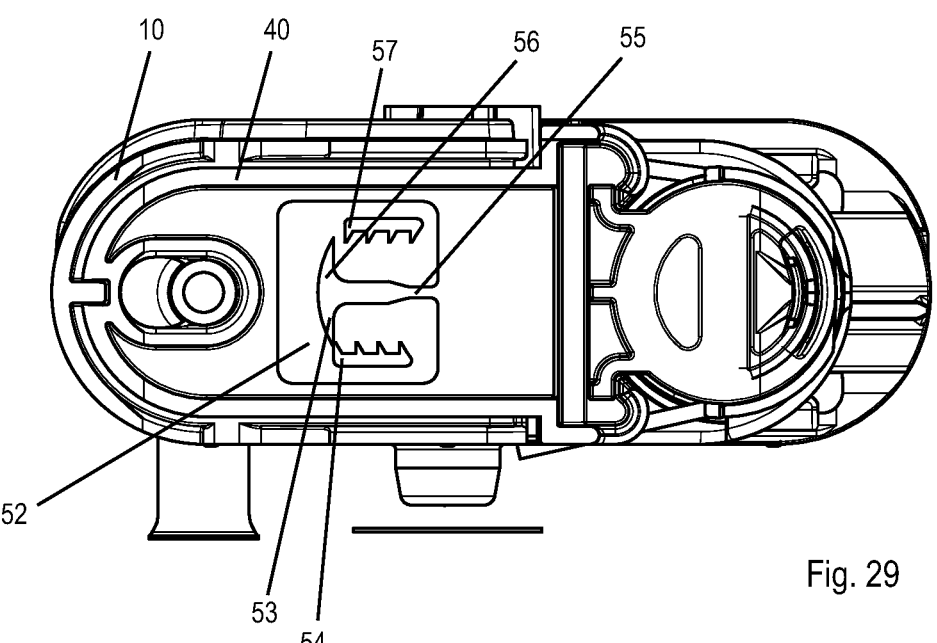
FIGS. 29 to 31: Side view of a needle insertion mechanism with a releasable coupling arrangement according to a fourth embodiment.
Figure 30:
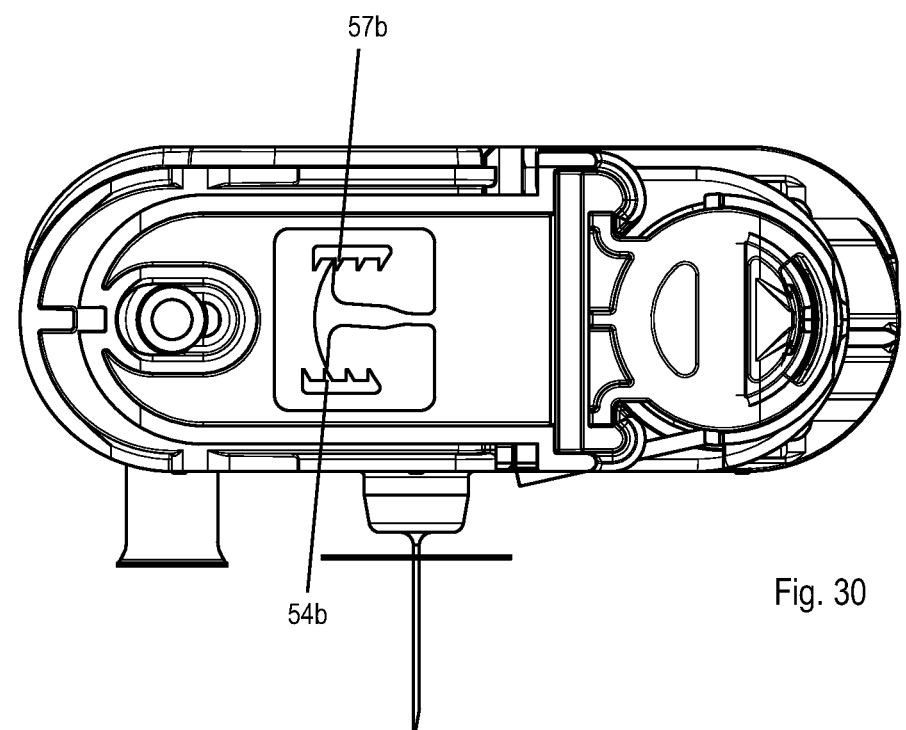
Figure 31:
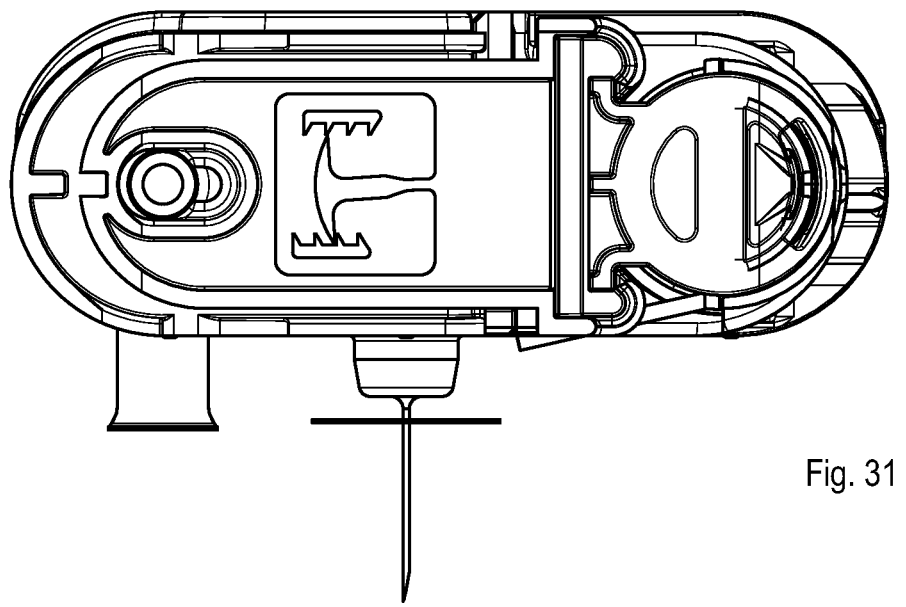

A side view of the needle insertion and retraction module according to a fourth embodiment is shown in FIGS. 29 to 31. The releasable coupling arrangement 52 includes the second coupling member 54 and fourth coupling member 57 which are both shaped as an array of teeth, for example ratchet teeth 54b and 57b. The second and fourth coupling members 54, 57 are spaced apart on the housing 10. The first coupling member 53 and a third coupling member 56 are located on a T-shaped protrusion that is connected via flexible member 55 to the slider 40. The T-shaped protrusion is located between the second and fourth coupling members 54, 57 on the housing 10. When the slider 40 is in the first slider position (FIG. 29), then one of the two first and third coupling members 53, 56 on the slider engages one of the two second and fourth coupling member 54, 57 on the housing. When the slider 40 is moved, the mutual engagement and release of coupling members on the T-shaped protrusion of the slider 40 and on the housing 10 bring the T-shaped protrusion in a pendulum movement thereby flexing the elastic arm 55 (e.g., FIGS. 29 and 30). Each engagement and release of coupling members may involve mutual engagement of sloped or curved surfaces and may requires energy for the release of such an engagement, thereby forming the actuation threshold for slider movement from the first slider position (FIG. 29) to the second slider position (FIG. 31).

Figure 32:
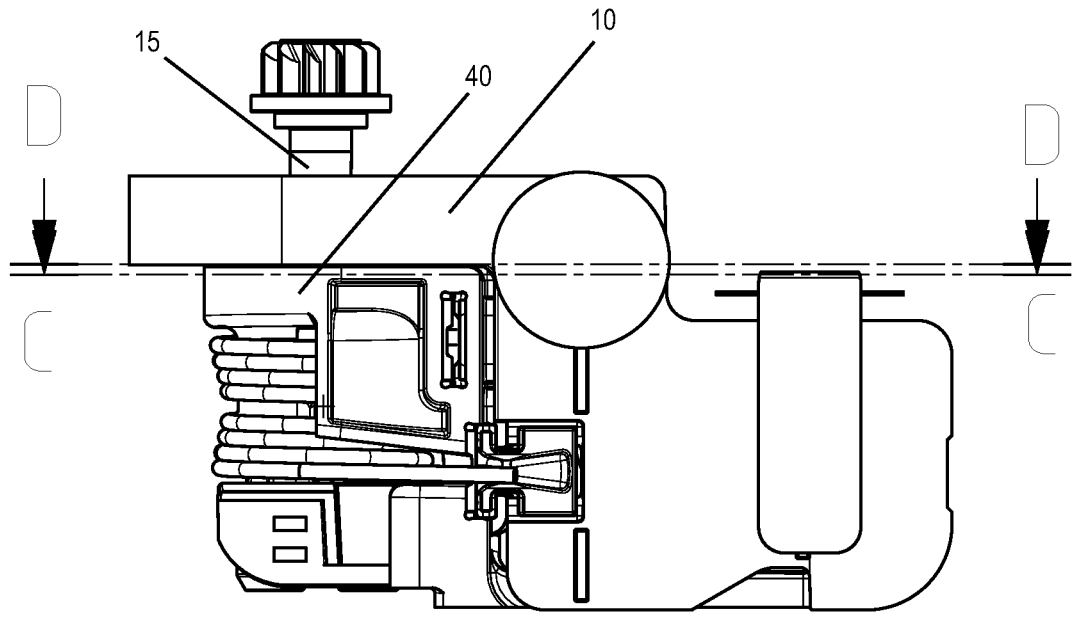
FIGS. 32, 32a, 32b, 33a, 33b, 34a and 34b: Side view of a needle insertion mechanism with a releasable coupling arrangement according to a fifth embodiment.
Figure 32A:
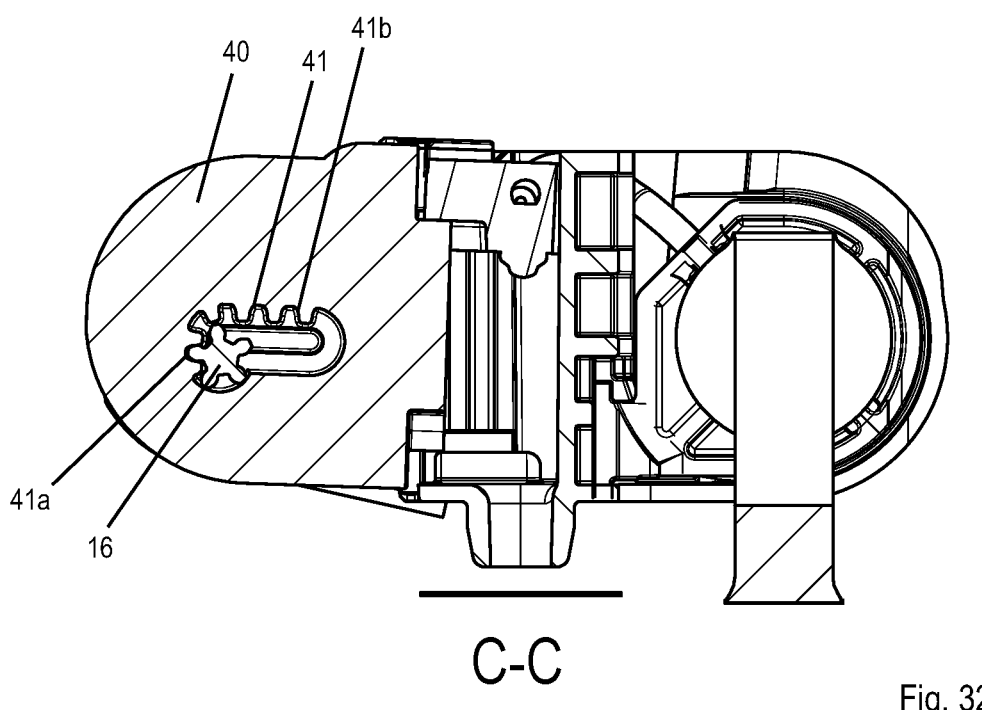
Figure 32B:
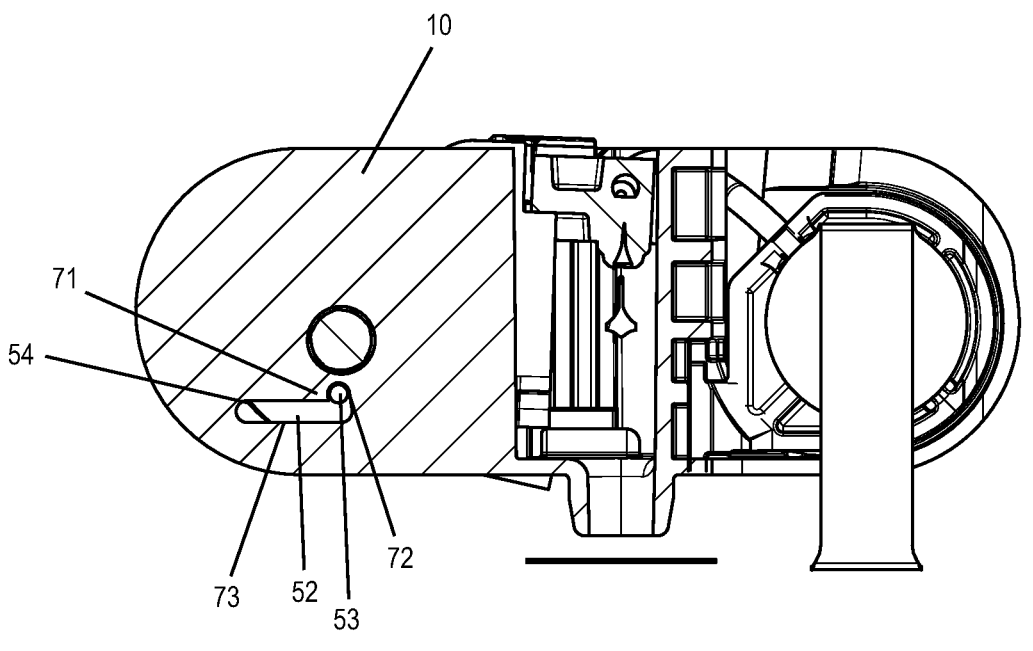

A top view of a releasable coupling arrangement according to a fifth embodiment is presented in FIG. 32. Two cross-sections are indicated through the slider 40 (C-C) and the housing 10 (D-D), FIG. 32a and FIG. 32b, respectively. The cross-sections A-A (FIG. 33a) and E-E (FIG. 34a) are through the slider 40, whereas the sections B-B (FIG. 33b) and F-F (FIG. 34b) are through the housing 10. The first slider position is represented by FIGS. 32, 32a, 32b, the second slider position by FIGS. 34a and 34b.

Figure 33A:
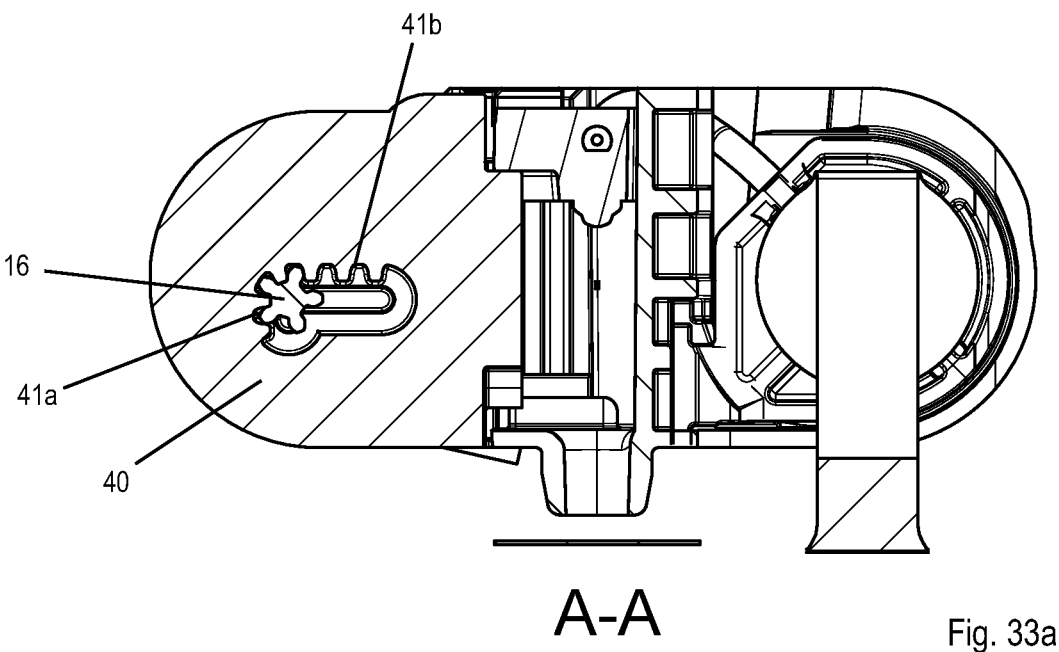
Figure 33B:
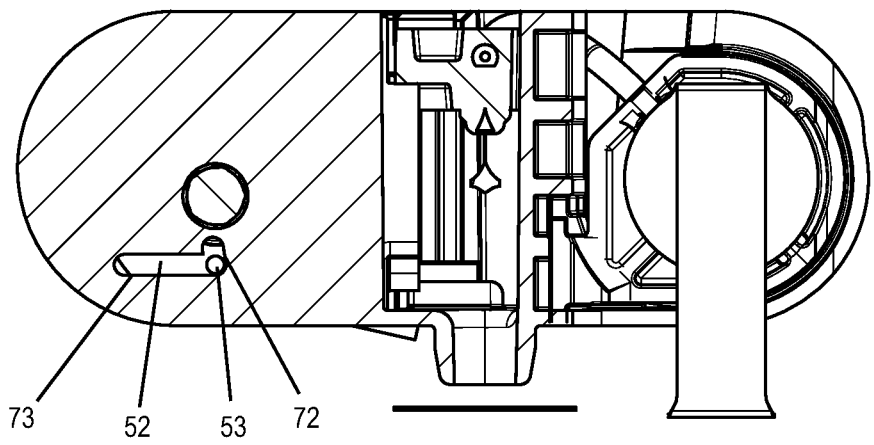
Figure 34A:
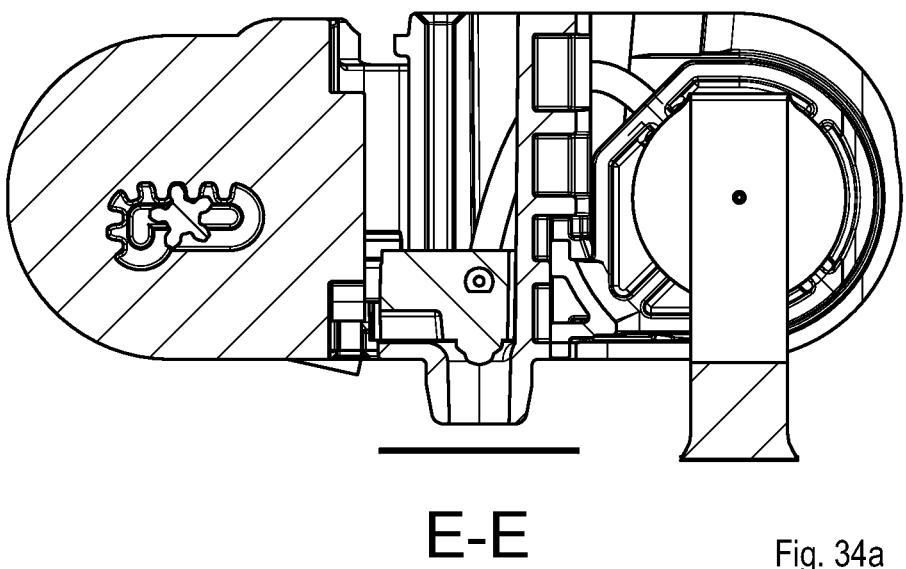
Figure 34B:
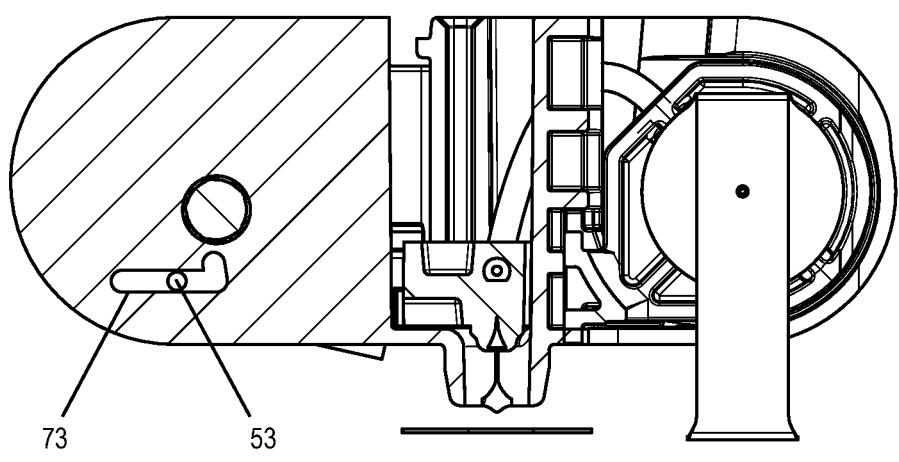

The slider 40 includes the gear rack 41 engaging the pinion or gear wheel 16 connected to the cam shaft. Rotation of the cam shaft by the active drive may activate the rack and pinion arrangement between the housing 10 and the slider 40 to move the slider 40 from the first position towards the second position. In the fifth embodiment, the gear rack 41 includes a first section 41a that is off-set, for instance oriented perpendicular to, the second section of the gear rack 41b. Upon rotation of the cam shaft, the engagement between the pinion and the first section 41a of the gear rack 41 shifts the slider 40 parallel to the needle insertion direction whereas the engagement between the pinion and the second section 41b of the gear rack 41 shifts the slider 40 from the first to the second slider position, a movement essentially perpendicular to the needle insertion direction. The movement of the slider 40 towards the second slider position is blocked by a releasable coupling arrangement 52 formed by motion-link 71. The motion-link 71 provides a form-fit engagement between the slider 40 and the housing 10 to be released prior to slider movement into the second slider position. The motion-link 71 includes a protrusion 53, or first coupling member, on the slider 40 engaging a first part of a slotted link 72 on the housing 10 when the slider is in the first slider position (FIG. 32b). When the gear wheel 16 is rotated by the active drive, then first part of the gear rack 41 ensures that the slider 40 is moved (FIG. 33a) such that the protrusion 53 is moved from the first part of the slotted link 72 into a second part of the slotted link 73 (FIG. 33b). The first and second slotted links are oriented perpendicular or oblique to another and when the protrusion 53 is in the second part of the slotted link 73, then movement of the slider 40 into the second slider position is allowed as the pinion advances in the gear rack 41 (FIGS. 34a and 34b).

Figure 35:
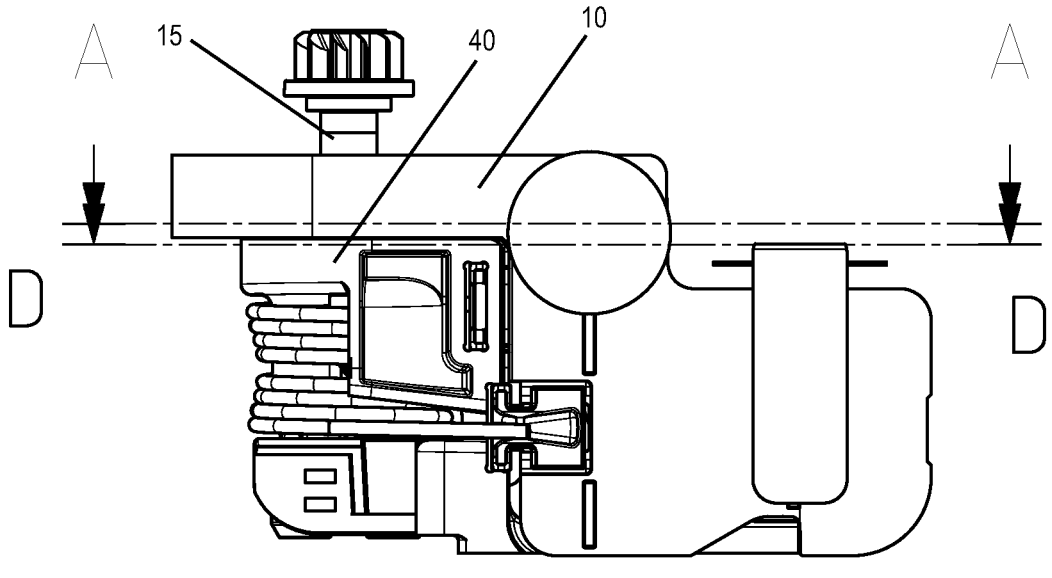
FIGS. 35, 35a, 35b, 36a, 36b, 37a, and 37b: Side view of a needle insertion mechanism with a releasable coupling arrangement according to a sixth embodiment.
Figure 35A:
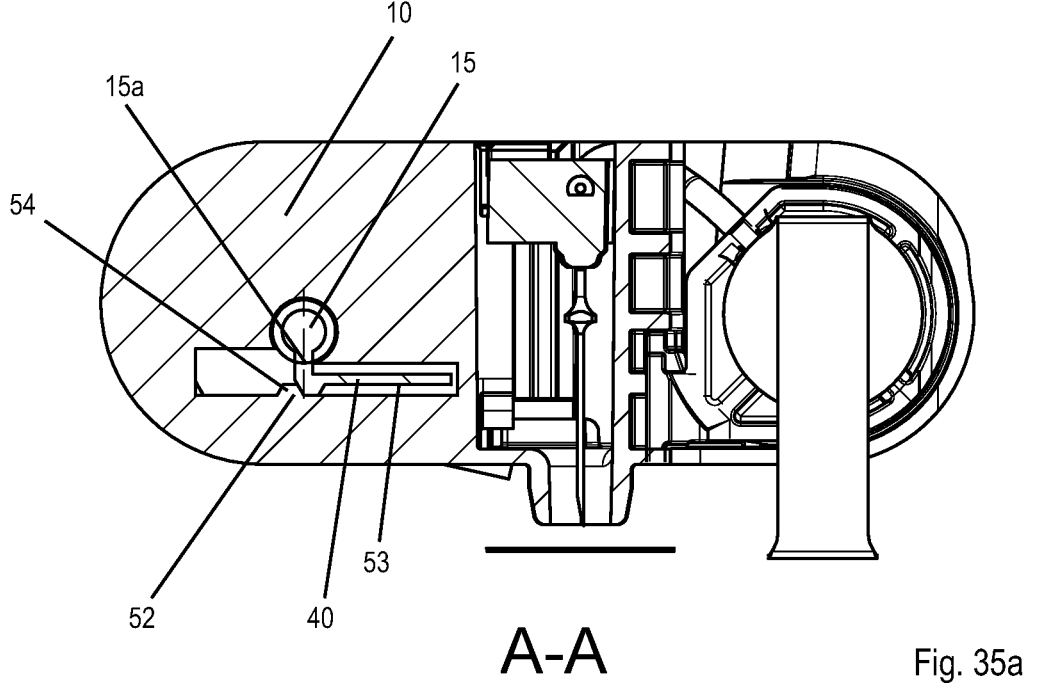
Figure 35B:
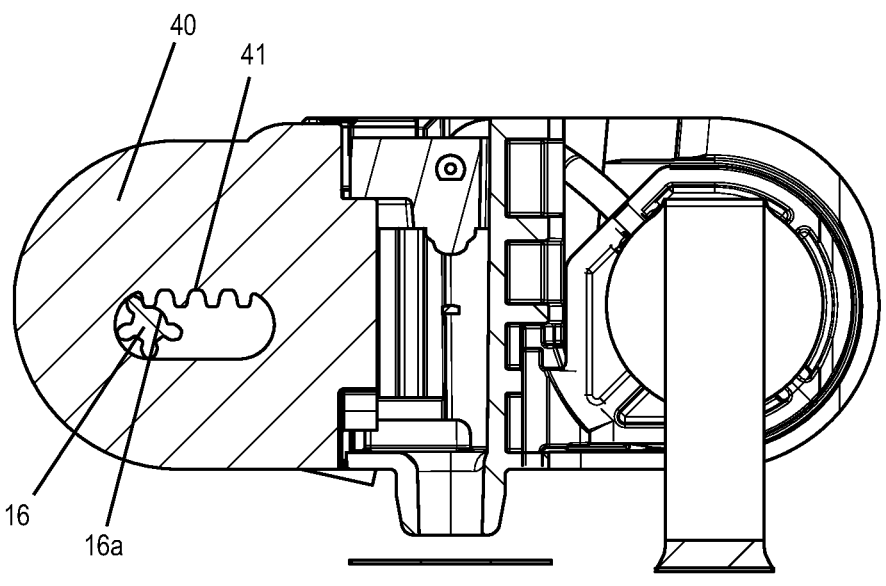

A top view of a releasable coupling arrangement according to a sixth embodiment is presented in FIG. 35. Two cross-sections are indicated through the slider 40 (D-D) and the housing 10 (A-A), FIGS. 35b, 35a. The cross-sections B-B (FIG. 36a) and C-C (FIG. 37a) are through the housing 10, whereas the sections E-E (FIG. 36b) and F-F (FIG. 37b) are through the slider 40.

Figure 36A:
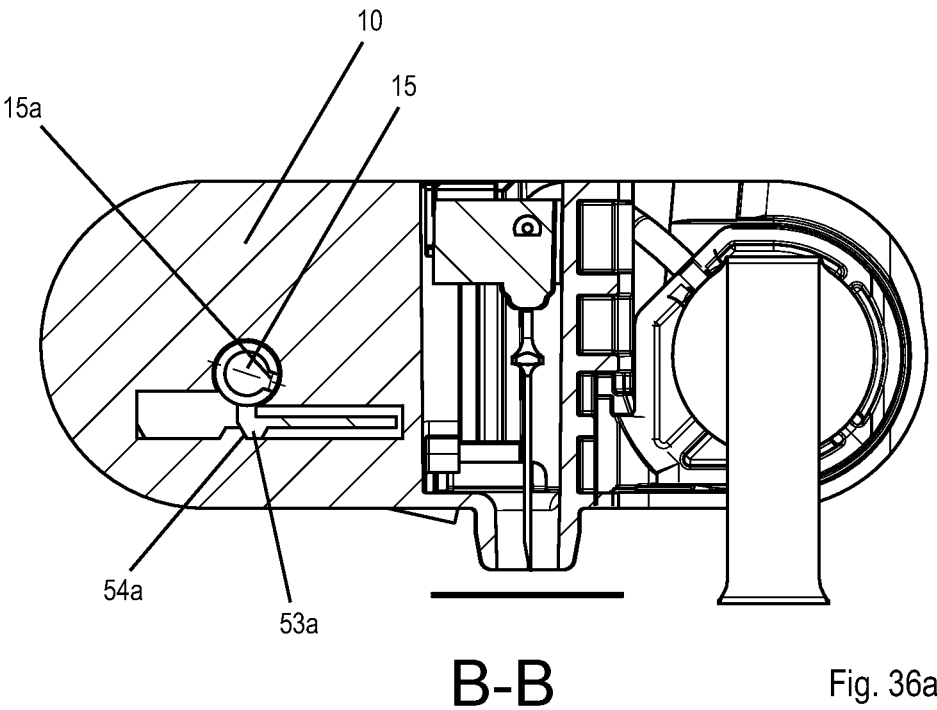
Figure 36B:
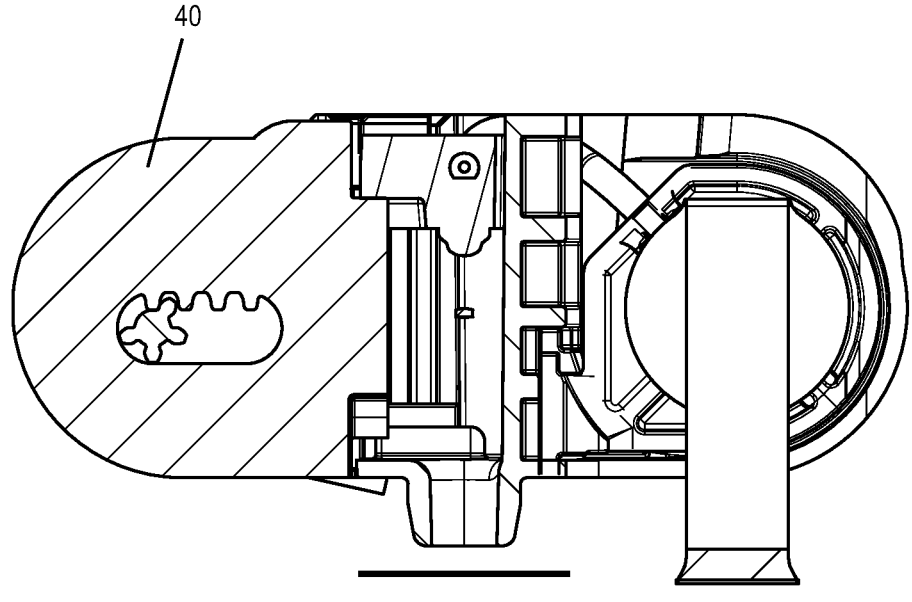
Figure 37A:
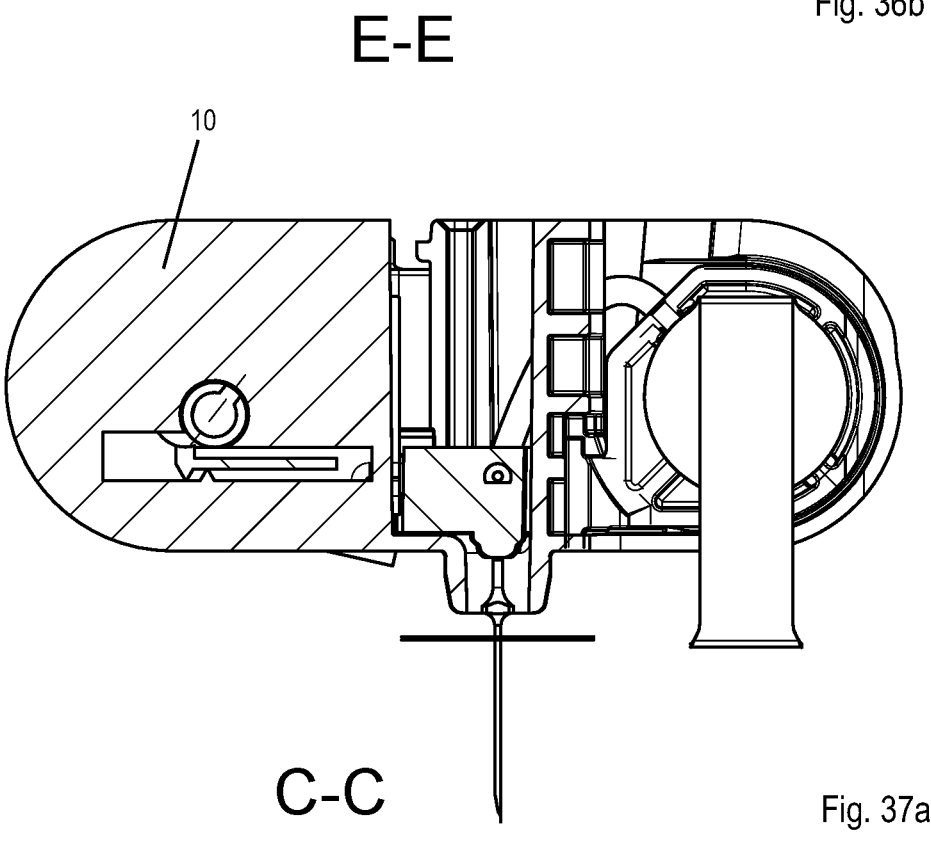
Figure 37B:
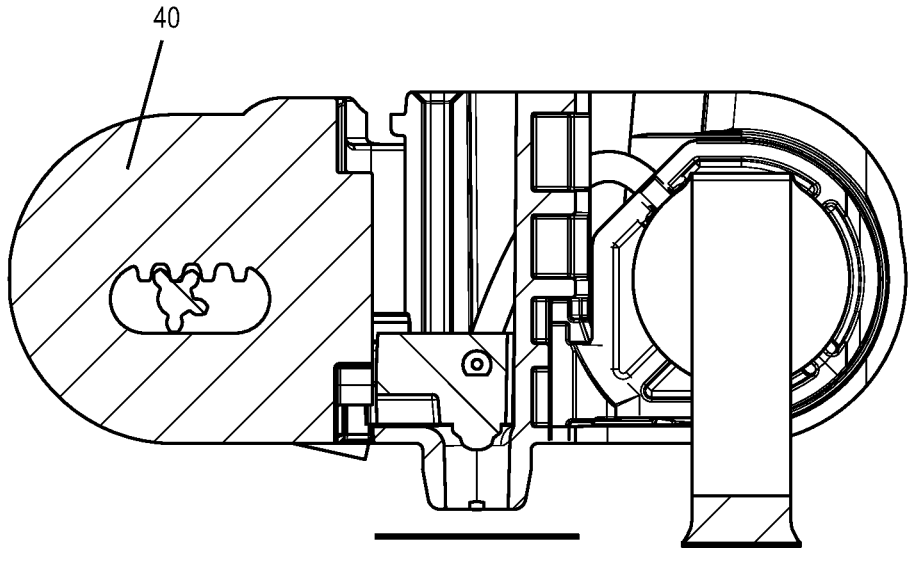

The engagement between the pinion or gear wheel 16 and the gear rack 41 has been modified in that the gear wheel 16 misses at least one tooth. The gear wheel 16 with the lacking tooth 16a is engaged with the gear rack 41 such that there is a rotational play before the cam shaft can move the slider 40, see FIGS. 35b and 36b. Once the teeth engage the gear rack 41, rotation of the gear wheel 16 can move the slider 40 from the first to the second position (FIG. 37b). The initial rotational play is used to release a releasable coupling engagement 52 (FIG. 35a) between an abutment surface 15a on the cam shaft 15 and a first coupling member 53 on the slider 40. The first coupling member 53 on the slider 40 is shaped as a flexible arm ending with a sloped surface 53a. The abutment between the cam shaft and the first coupling member 53 prevents a flexing movement of the first coupling member 53. Once the cam shaft is rotated over a first angle—corresponding to the rotational play mentioned above, the abutment between the cam shaft and the first coupling member 53 is released and the arm may flex (compare FIGS. 35a and 36a). The sloped surface 53a of the first coupling member on the slider 40 may be in abutment with a second coupling member 54 on the housing, such as with a complementary sloped surface 54a on the housing 10. As the cam shaft is rotated further, the arm of the first coupling member 53 is flexed and the slider 40 can be moved from the first to the second slider position (FIGS. 36*a* and 37*a*). The actuation threshold in this embodiment is established by a form-fit engagement between the cam shaft and the first coupling member preventing any movement of the first coupling member that may be required for the slider movement.

Referring to FIGS. 38*a* to 50*d* embodiments of a needle insertion and retraction module including a needle insertion and retraction mechanism 3 are disclosed with a blocking member positioned between the slider 40 (control element) and the housing.

Figures 38A, 38B, 38C, 38D:
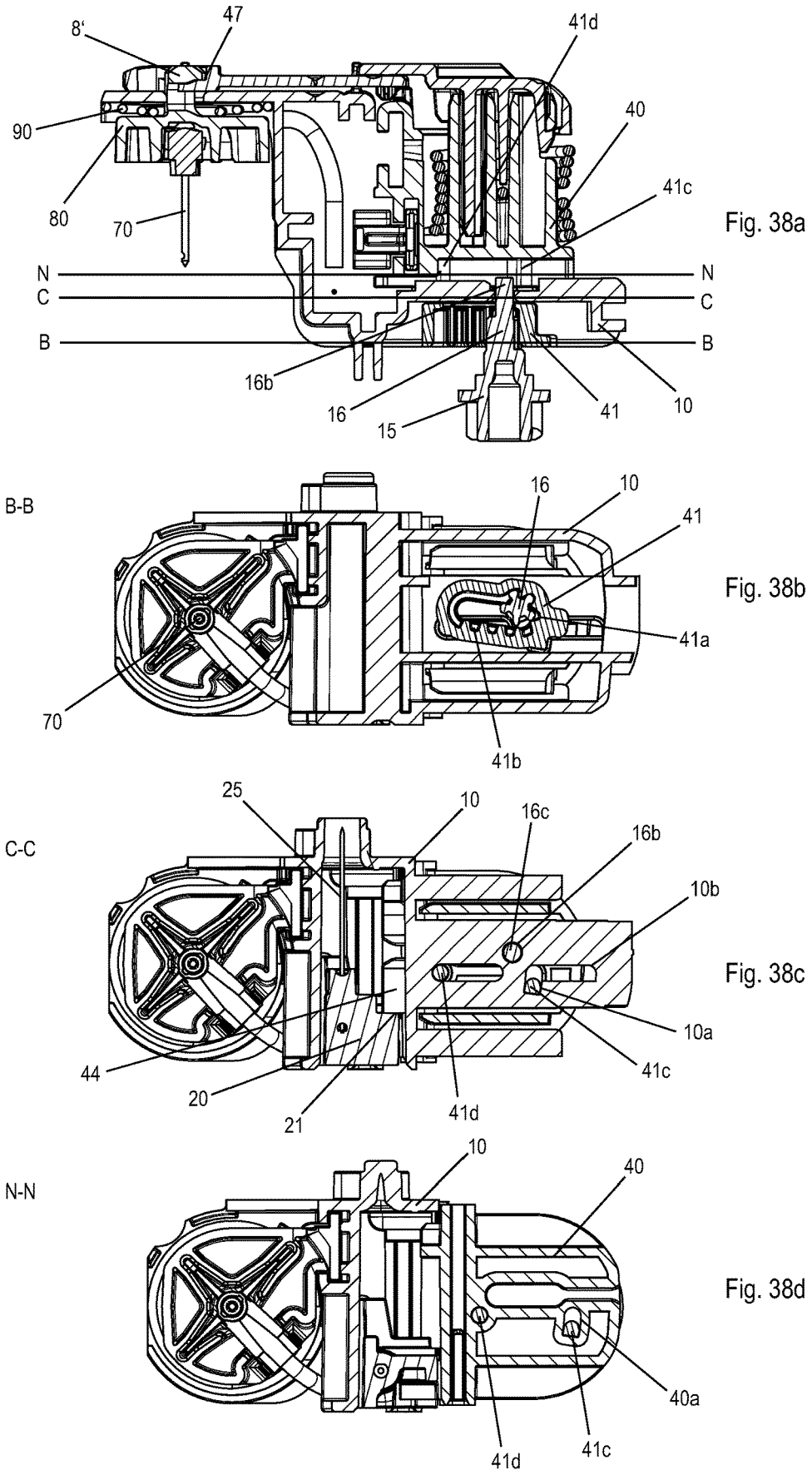
FIGS. 38a-38d: A needle insertion mechanism with a blocking member according to a first embodiment: Pivot mounted gear rack in the tilted position blocking the movement of the slider.

A cross-section for a needle insertion mechanism with a blocking member according to a first embodiment is presented in FIG. 38*a*. In the first embodiment, a part of the housing is positioned between the slider and the gear rack. The cross-section is parallel to the hollow spike 70. FIGS. 38*b*, 38*c* and 38*d* present cross-sections perpendicular to the hollow spike 70 taken at positions B-B, C-C and N-N, respectively, indicated in FIG. 38*a*. The slider 40 is splined to the housing 10 or mechanism holder such that the slider 40 can move with respect to the housing 10 starting from a first slider position (FIGS. 38*a-d*). The slider 40 includes a pivot mounted gear rack 41 having a first protrusion 41*d* extending from the surface of the gear rack 41, passing through a passage in the housing 10 (FIG. 38*c*) and engaging a complementary bore in the slider 40 (FIG. 38*d*). The pivot mounted gear rack 41 includes a second protrusion 41*c* passing through a guide slot 10*a*, 10*b* in the housing 10 (FIG. 38*c*) and finally engaging a guide slot 40*a* in the slider 40 (FIG. 38*d*). The passages and guide slots in the housing 10 allow for rotating or pivot movement of the gear rack 41 around the first protrusion 41*d*. The gear rack 41 is in the tilted position as presented in FIG. 38*b* and the gear wheel 16 engages the first section 41*a* of the gear teeth. The gear wheel 16 is part of the cam shaft 15 and the shaft end 16*c* engages a passage in the housing 10 to form the end bearing 16*b* of the cam shaft 15. The second protrusion 41*c* engages a guide slot 40*a* in the slider and also engages the first section 10*a* of the guide slot in the housing. In the tilted position of the gear rack 41, the gear rack 41, and therewith also the slider 40, is prevented from movement towards the second slider position as the second protrusion 41*c* engages the first section 10*a* of the guide slot which is oriented perpendicular to the sliding direction for the slider (FIG. 38*c*). The second protrusion 41*c* is therefore in a form fit engagement with the housing 10 preventing movement of the slider 40 out of the first slider position towards the second slider position.

As the slider 40 remains in the first slider position, also the insertion needle 25 and the spike 70 are prevented from moving towards their respective inserted positions. The insertion needle 25 is part of the needle carrier 20 and the needle carrier 20 has a counter stop surface 21 abutting the stop surface 44 of the slider 40 (FIG. 38*a*). The needle carrier 20 is held in the retracted position against the bias of compressed spring 31 (see FIGS. 3 and 5). The spike 70 is part of the spike carrier 80 having a protrusion with a countersurface 81 engaging a retaining surface 47 on the slider 40 thereby keeping the spike carrier 80 in the retracted position against the bias of spring 90.

Figure 39A:
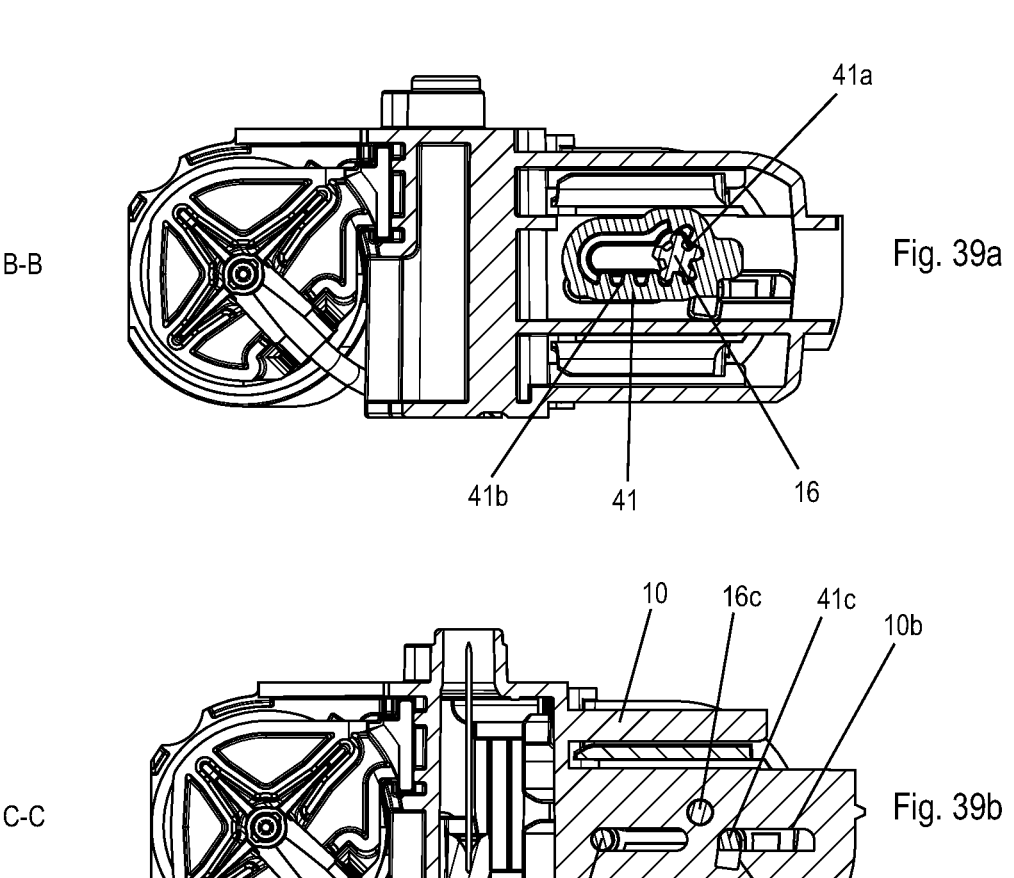
FIGS. 39a-39c: A needle insertion mechanism with a blocking member according to a first embodiment: Pivot mounted gear rack in the untilted position unblocking the slider movement.
Figure 39B:
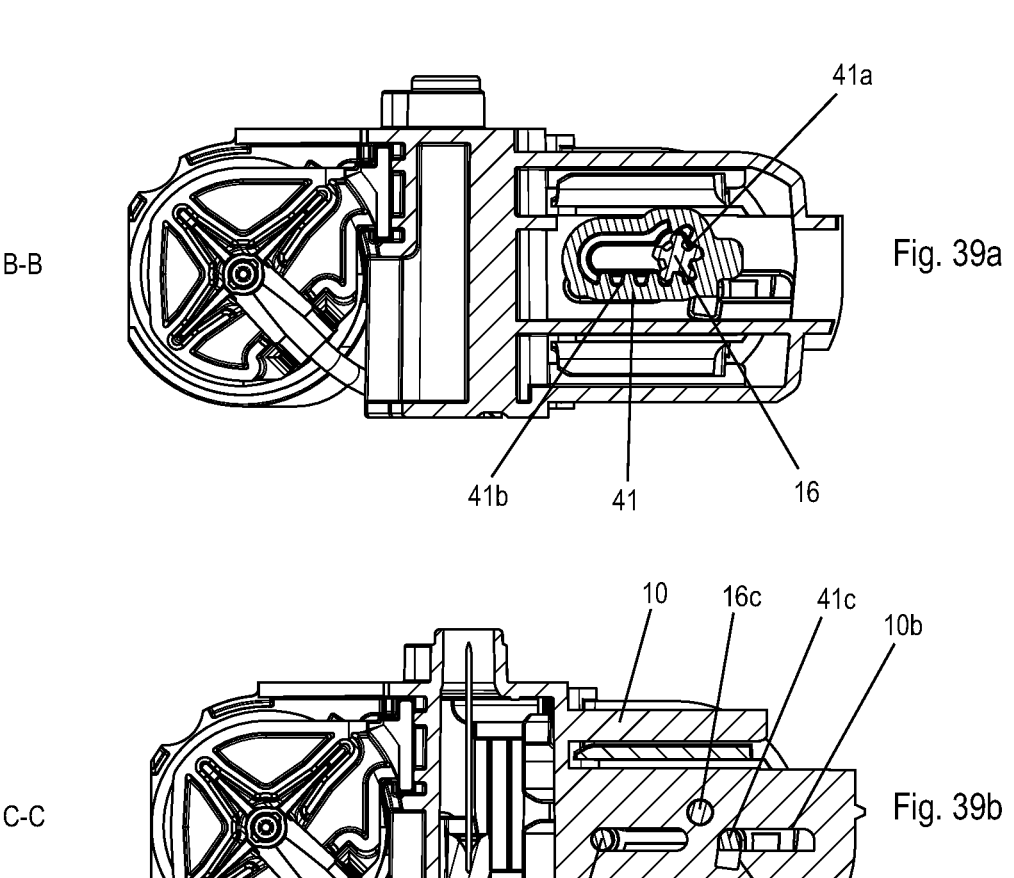
Figure 39C:
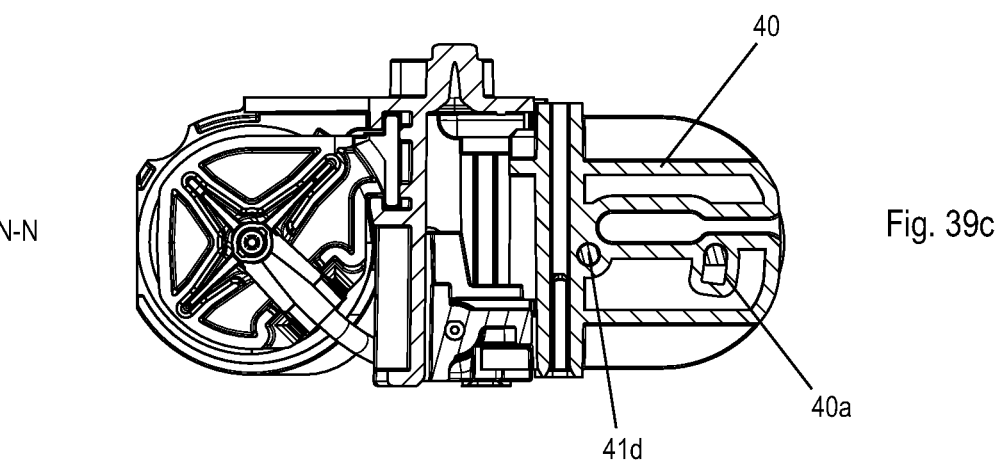
Figure 40A:
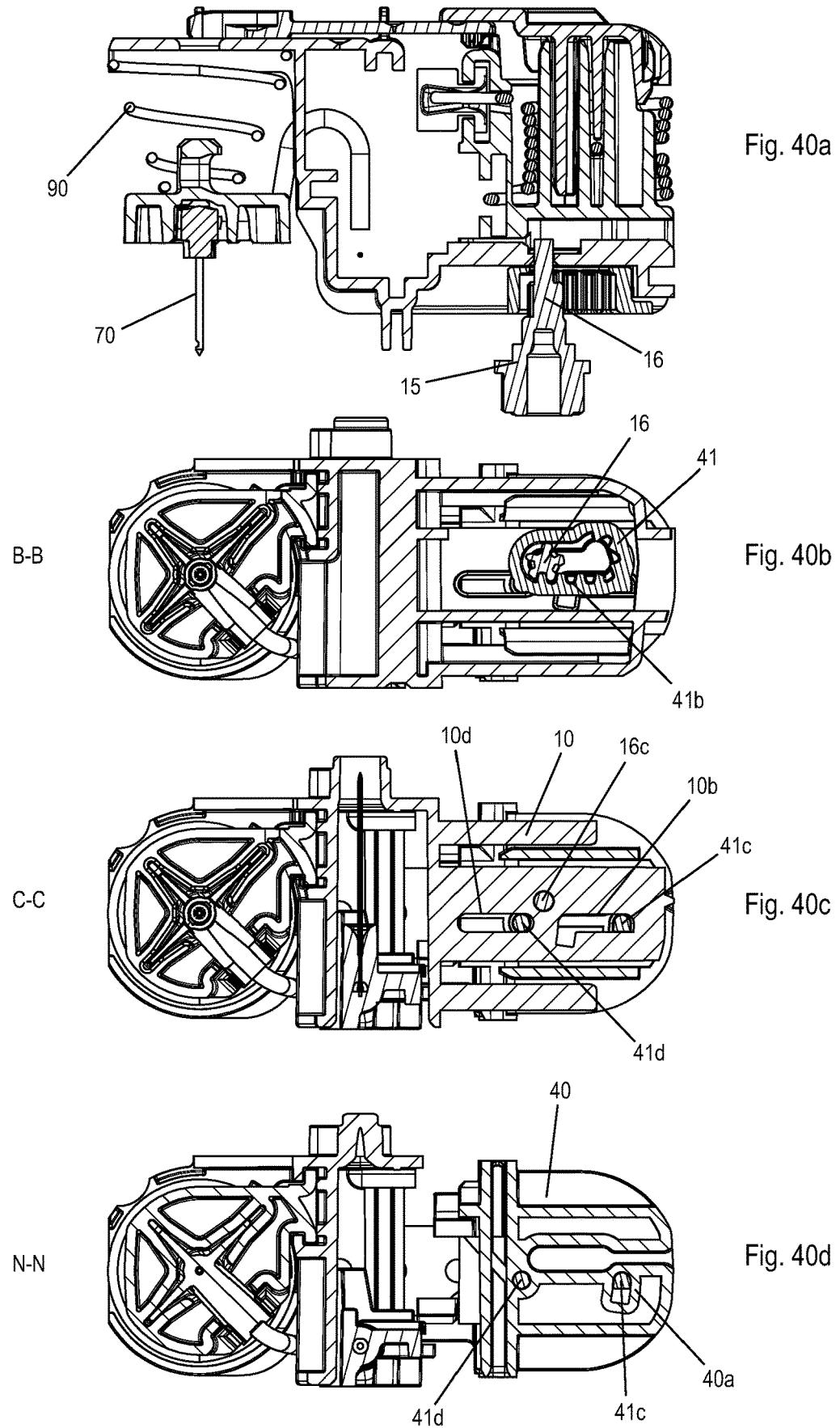

Rotation of the cam shaft 15 in the counterclockwise direction rotates the gear rack 41 around the first protrusion 41*d* from the tilted to the untilted position (FIG. 39*a*). The teeth of the gear wheel 16 engage the first section 41*a* of the gear rack that is oriented parallel to the skin needle and rotation of the cam shaft rotates the pivot mounted gear rack 41. The second protrusion 41*c* moves through the first section 10*a* of the guide slot in the housing 10 (FIG. 39*b*) and moves through the guide slot 40*a* in the slider (FIG. 39*c*). Further rotation of the cam shaft 15 in the counterclockwise direction ensures that the second section 41*b* of the gear teeth of the gear rack 41 is activated and the rotation moves the gear rack 41 together with the slider 40 out of the first position towards the second position. The first protrusion 41*d* of the gear rack engages the slider 40 in a bore and the second protrusion 41*c* engages the guide slot 40*a* and both allow for load transfer from the gear rack 41 to the slider 40 such that both the gear rack 41 and the slider 40 can move into the second position with respect to the housing 10 (FIG. 40*d*). The second protrusion 41*c* has moved from the first section 10*a* of the guide slot into the second section 10*b* of the guide slot in the housing 10. The second section 10*b* of the guide slot in the housing allows for lateral movement of the second protrusion 41*c* on the gear rack 41 with respect to the housing 10. The release of the form fit engagement between the second protrusion 41*c* and the housing 10 therefore unblocks the movement of the gear rack 41 (being an example of a blocking member) and therewith also unblocks the movement of the slider 40. Additionally, movement of the gear rack 41 back to the tilted position is prevented once the second protrusion 41*c* of the gear rack has entered the second section 10*b* of the guide slot in the housing 10 (FIG. 40*c*). A second longitudinal passage 10*d* in the housing allows for lateral movement of the first protrusion 41*d* with respect to the housing (FIG. 40*c*). The engagement 44, 21 between the needle carrier 20 (FIG. 38*c*) and the slider 40 and the engagement 8', 47 between the spike carrier 80 and the slider 40 (FIG. 38*a*) are released such that both the spike 70 and the skin needle 25 can move towards their respective inserted positions as the slider 40 has moved into the second slider position (FIGS. 40*a*, 40*b*, 40*c*, 40*d*).

Figures 41A, 41B, 41C:
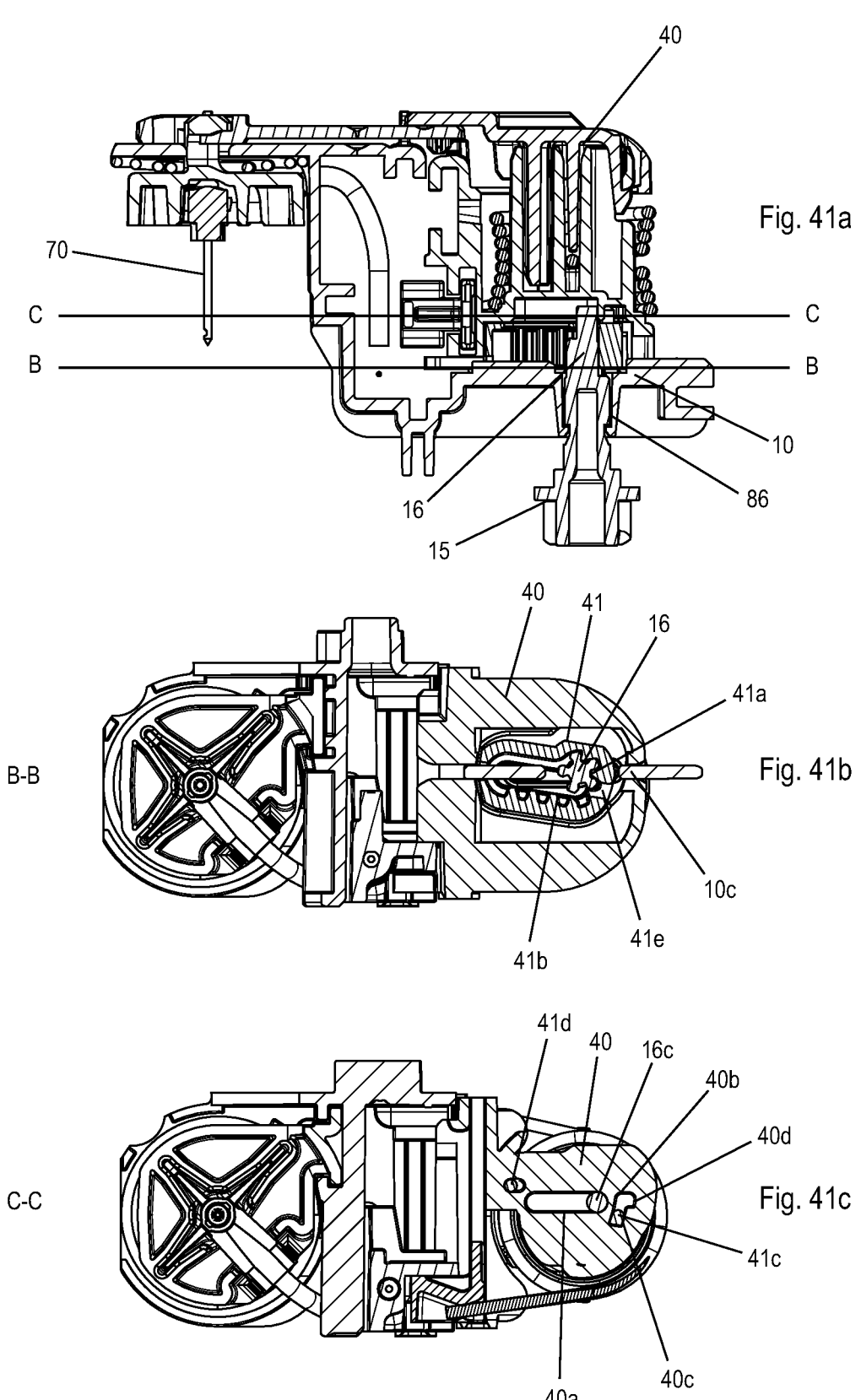
FIGS. 41a-41c: A needle insertion mechanism with a blocking member according to a second embodiment: Pivot mounted gear rack in the tilted position blocking the movement of the slider.

A cross-section for a needle insertion mechanism with a blocking member according to a second embodiment is presented in FIG. 41*a*. The cross-section is parallel to the hollow spike 70. FIGS. 41*b* and 41*c* present cross-sections perpendicular to the hollow spike 70 taken at positions B-B, C-C indicated in FIG. 41*a*.

The slider 40 includes a pivot mounted gear rack 41 and works essentially identical to the first embodiment. The gear rack 41 is directly mounted onto the slider 40 such that the first and second protrusions 41*d*, 41*c* are not passing through corresponding guide slots in the housing 10. The pivot mounted gear rack 41 includes a passage 41*e* and the housing 10 includes a complementary protrusion 10*c*. The protrusion 10*c* is oriented parallel to the direction of the movement of the slider 40. The protrusion 10*c* and the passage 41*e* are not aligned when the gear rack 41 is in the tilted position (FIG. 41*b*) and consequently the gear rack 41 and the slider 40 are blocked from moving out of the first slider position. The slider 40 includes a guide slot 40*c*, 40*d* for the second protrusion 41*c* of the gear rack 41 whereas the first protrusion 41*d* engages a bore in the slider 40. The bore allows for a certain lateral play between the gear rack 41 and the slider 40. In the tilted position, the second protrusion 41*c* engages the first section 40*c* of the guide slot in the slider (FIG. 41*c*).

Figures 42A, 42B, 43A, 43B:
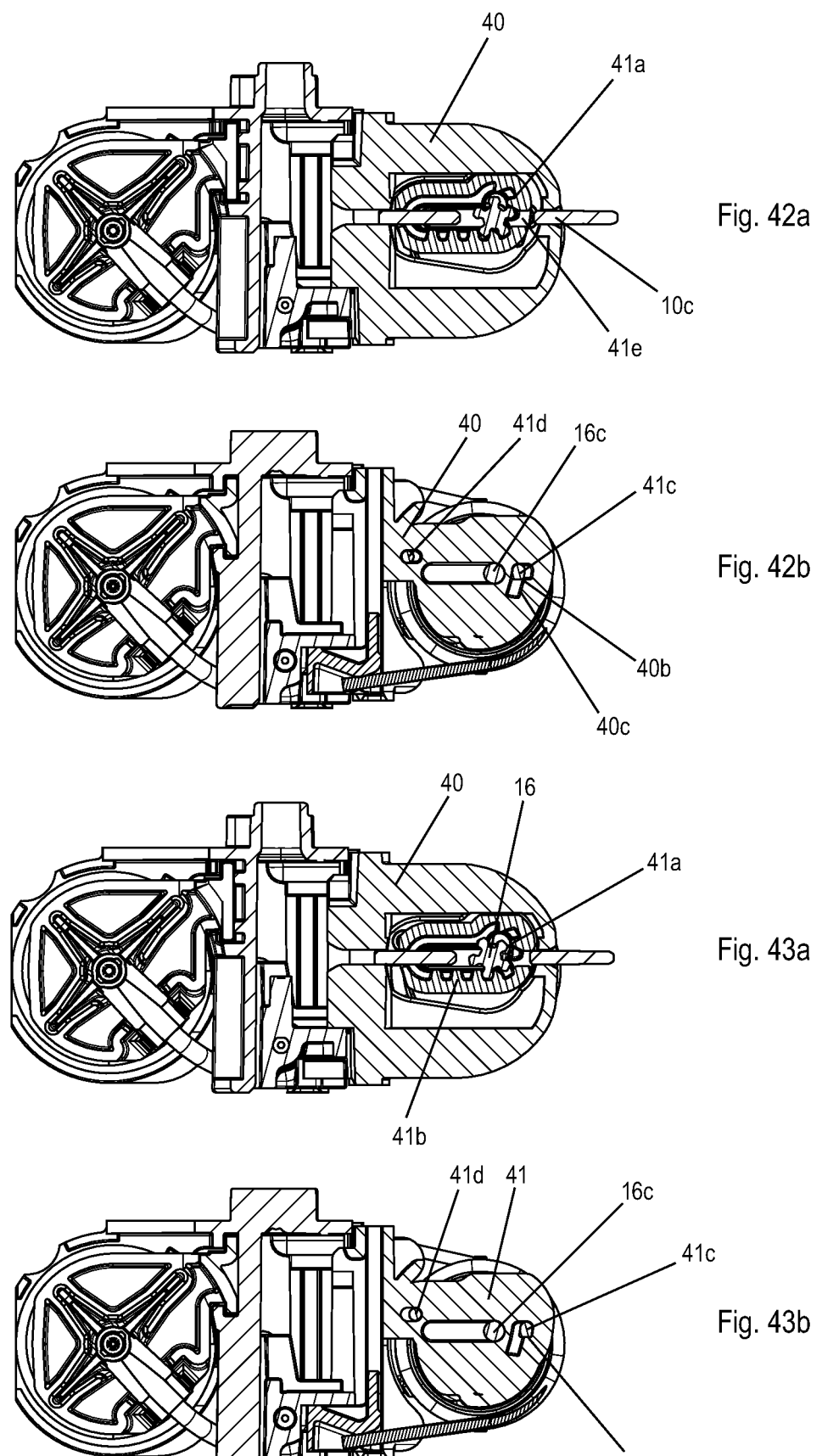
FIGS. 42a-42b: A needle insertion mechanism with a blocking member according to a second embodiment: Pivot mounted gear rack in the untilted position unblocking the movement of the slider.
FIGS. 43a-43b: A needle insertion mechanism with a blocking member according to a second embodiment: Pivot mounted gear rack in the untilted position, return to the tilted position is prevented and unblocking the movement of the slider.
Figure 44A:
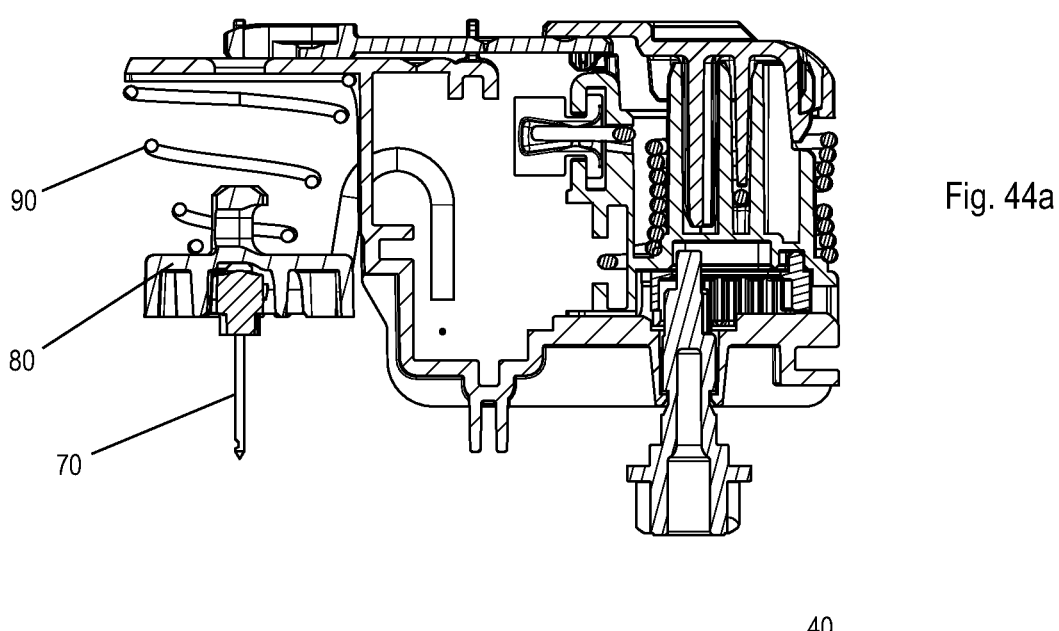
FIGS. 44a-44c: A needle insertion mechanism with a blocking member according to a second embodiment: Pivot mounted gear rack in the untilted position slider has moved to the second slider position.
Figure 44B:
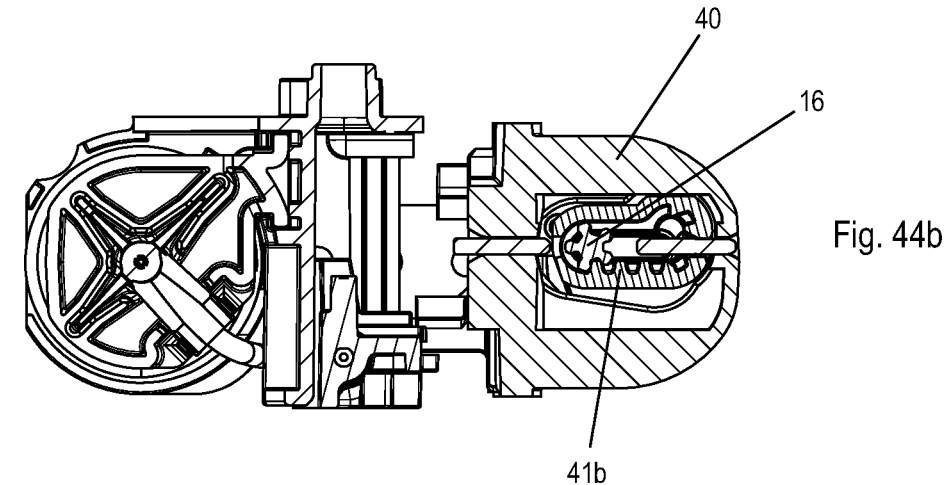
Figure 44C:
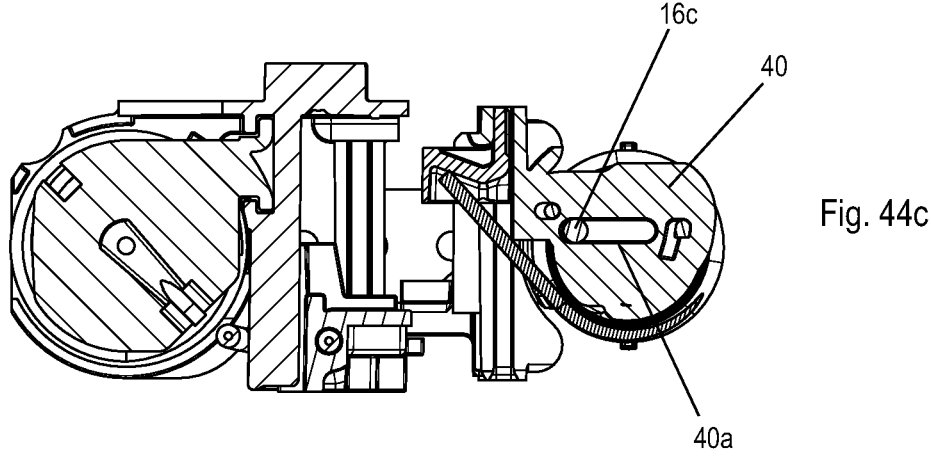

Rotation of the cam shaft 15 in the counterclockwise direction rotates the pivot mounted gear rack 41 from the tilted to the untilted position due to the gearing engagement between the gear wheel 16 and the teeth 41*a* on the gear rack 41. The protrusion 10*c* on the housing is now aligned with the passage 41*e* of the gear rack (FIG. 42*a*). The second protrusion 41*c* of the gear rack 41 has moved through the first section 40*c* of the guide slot in the slider 40 (FIG. 42*b*). The second section 41*b* of the gear teeth of the gear rack 41 are activated upon further rotation of the cam shaft 15 such that the protrusion 10*c* can enter the passage 41*e* in the gear rack 41. First, there may be a relative shift of the gear rack 41 with respect to the slider 40 before moving the slider 40 out of the first slider position. The second protrusion 41*c* moves into the second section 40*b* of the slider (compare FIG. 42*b* with 43*b*) such that the pivot mounted gear rack 41 is prevented from rotating back into the tilted position. The first protrusion 41*d* on the gear rack 41 may move axially within the play of the passage in the slider 40 to permit entry of the second protrusion 41*c* into the second section 40*d* of the guide slot 40*b*. The axial shift of the gear rack 41 with respect to the slider 40 is shown in FIGS. 43*a* and 43*b* and may be required before the load can be transferred from the gear wheel 16 to the gear rack 41 via gear teeth 41*b*, and subsequently from the gear rack 41 to the slider 40. Further rotation of the cam shaft 15 in the counterclockwise direction shifts the slider 40 from the first slider position to the second slider position thereby releasing the spike 70 and needle 25 as described above for the first embodiment (FIGS. 44*a*, 44*b*, 44*c*). The load is transferred from the gear rack to the slider via the two protrusions on the pivot mounted gear rack as the shaft end 16*c* of the cam shaft shifts through the guide slot 40*a* in the slider (compare FIG. 43*b* with 44*c*).

Figures 45A, 45B, 45C:
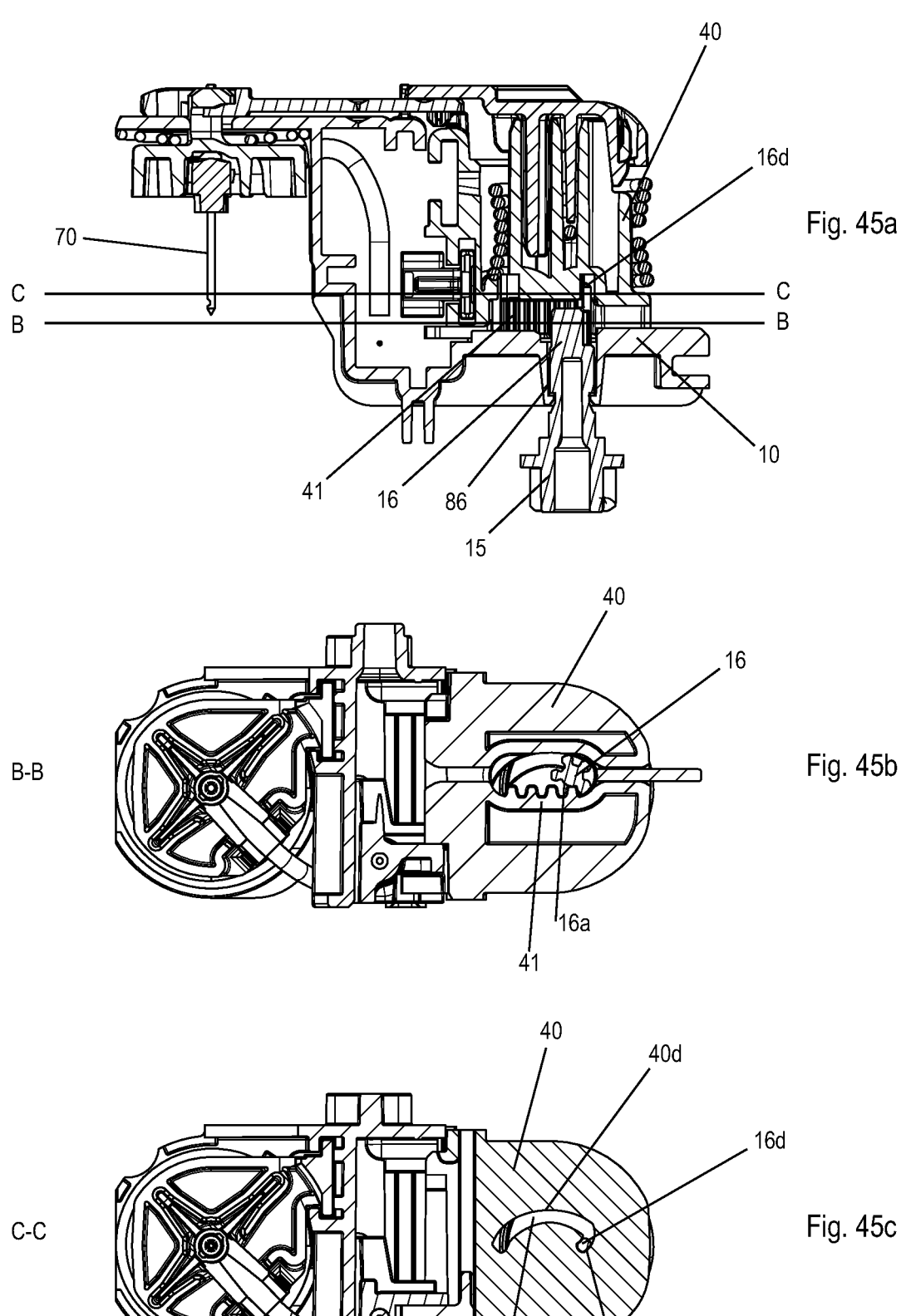
FIGS. 45a-45c: A needle insertion mechanism with a blocking member according to a third embodiment: Interaction of the protrusion on the gear wheel of the cam shaft and the groove on the slider prevents slider movement.

A cross-section for a needle insertion mechanism with a blocking member according to a third embodiment is presented in FIGS. 45*a* to 47*b*. The cross-section in FIG. 45*a* is parallel to the hollow spike 70. FIGS. 45*b* and 45*c* present cross-sections perpendicular to the hollow spike 70 taken at positions B-B, C-C indicated in FIG. 45*a*.

Figures 46A, 46B, 47A, 47B:
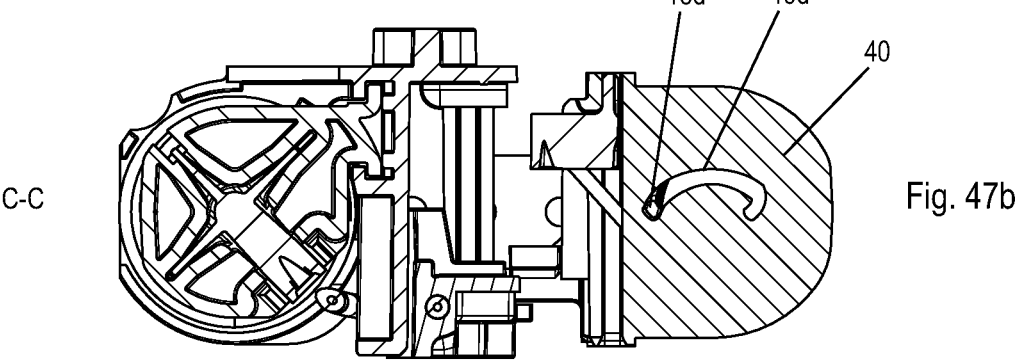
FIGS. 46a-46b: A needle insertion mechanism with a blocking member according to a third embodiment: Interaction of the protrusion on the gear wheel of the cam shaft and the groove on the slider allows slider movement.
FIGS. 47a-47b: A needle insertion mechanism with a blocking member according to a third embodiment: Slider in the second slider position

The slider 40 is in the first slider position in FIG. 45*a* and the cam shaft 15 is in a bearing engagement 86 with the housing 10 such that lateral forces, more specifically impact forces can be absorbed by the bearing engagement 86. A protrusion 16*d* extends from the gear wheel 16 of the cam shaft 15 and the protrusion 16*d* engages a guide slot 40*b* on the slider 40 (FIG. 45*c*). The protrusion 16*d* may be positioned eccentric from the central axis of the cam shaft 15. The guide slot 40*b* includes a first section 40*c* engaging the protrusion 16*d* when the slider 40 is in the first position. The engagement prevents or blocks a movement of the slider 40 towards the second slider position. Lateral forces on the slider 40 are guided via the protrusion 16*d* to the cam shaft 15 and finally via the bearing 86 to the housing 10. Rotation of the cam shaft 15 in the counterclockwise direction over a first angle will rotate the protrusion 16*d* as well and the protrusion 16*d* can enter the second section 40*d* of the guide slot 40*b* in the slider (FIG. 46*b*). Rotation of the cam shaft 15 over this first angle will not result in a shift of the slider 40 as the gear wheel 16 has a "missing" tooth 16*a* such that the gear rack 41 is not engaged during this first rotation (compare FIGS. 45*b* and 46*a*). Further rotation of the cam shaft 15 in the counterclockwise direction ensures that the teeth of the gear wheel 16 and the rack 41 are engaged such that the slider 40 can move from the first to the second slider position (FIG. 47*a*). The second section of the guide slot 40*d* in the slider has a curved shape accommodating the rotary movement of the eccentrically positioned protrusion 16*d* on the cam shaft 15 as the slider 40 moves into the second slider position (FIG. 47*b*).

A cross-section for a needle insertion mechanism with a blocking member according to a fourth embodiment is presented in FIGS. 48*a* to 49*b*. The working principle resembles the third embodiment. The release of the blocking member is, however, achieved by changing the rotation direction of the cam shaft.

Figures 48A, 48B, 49A, 49B:
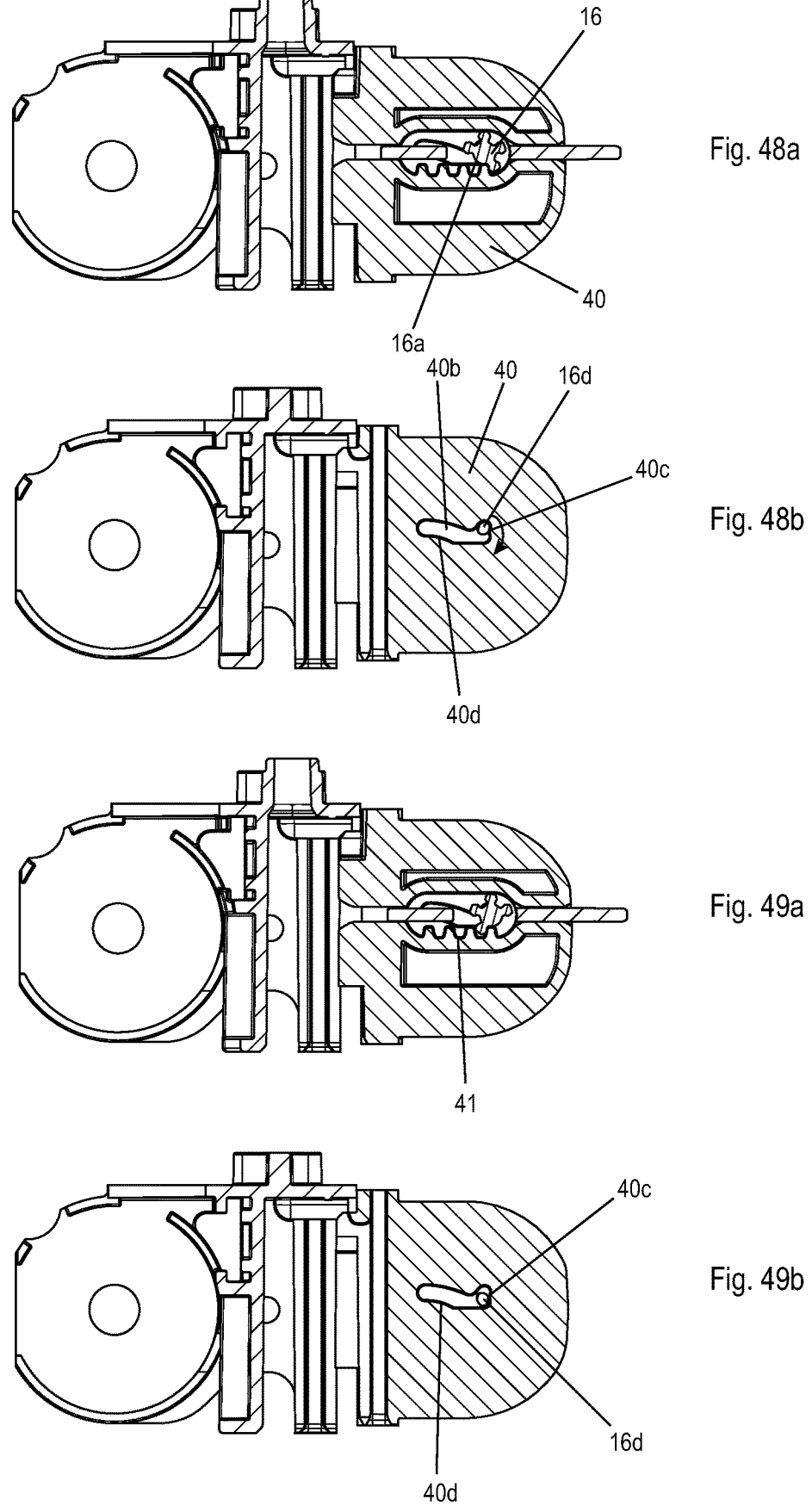
FIGS. 48a-48b: A needle insertion mechanism with a blocking member according to a fourth embodiment: Interaction of the protrusion on the gear wheel of the cam shaft and the groove on the slider prevents slider movement.
FIGS. 49*a*-49*b*: A needle insertion mechanism with a blocking member according to a fourth embodiment: Interaction of the protrusion on the gear wheel of the cam shaft and the groove on the slider allows slider movement.

The protrusion 16*d* on the cam shaft 15 engages the first section 40*c* of the guide slot 40*b* on the slider 40 when the slider 40 is in the first slider position thereby preventing axial movement of the slider (FIG. 48*b*). Rotation of the cam shaft in the clockwise direction over a first angle (compare FIGS. 48*a* and 49*a*) will shift the protrusion 16*d* through the first section 40*c* of the guide slot (compare FIGS. 48*b* and 49*b*). The initial rotation of the cam shaft 15 will not result in a movement or activation of the slider as a tooth is missing on the gear wheel 16. Subsequently the rotation direction of the cam shaft 15 is reversed to the counterclockwise direction and this will engage the teeth of the gear wheel 16 with the teeth of the gear rack 41 and the cam shaft 15 can drive the slider to the second slider position as the second protrusion 16*d* on the cam shaft shifts through the second section 40*d* of the guide slot. The shape of, and angle between, the first and second sections 40*c*, 40*d* of the guide slot and the eccentric arrangement of the protrusion 16*d* on the cam shaft ensures that the protrusion 16*d* will not go back into the first section 40*c* upon reversal of the rotation direction of the cam shaft 15.

A cross-section for a needle insertion mechanism with a blocking member according to a fifth embodiment is presented in FIGS. 50*a*-50*d*. The working principle resembles the third embodiment. The release of the blocking member is, however, achieved by rotation of a part this is part of or coupled to the coupling member 17 (FIG. 1).

Figures 50A, 50B, 50C, 50D:
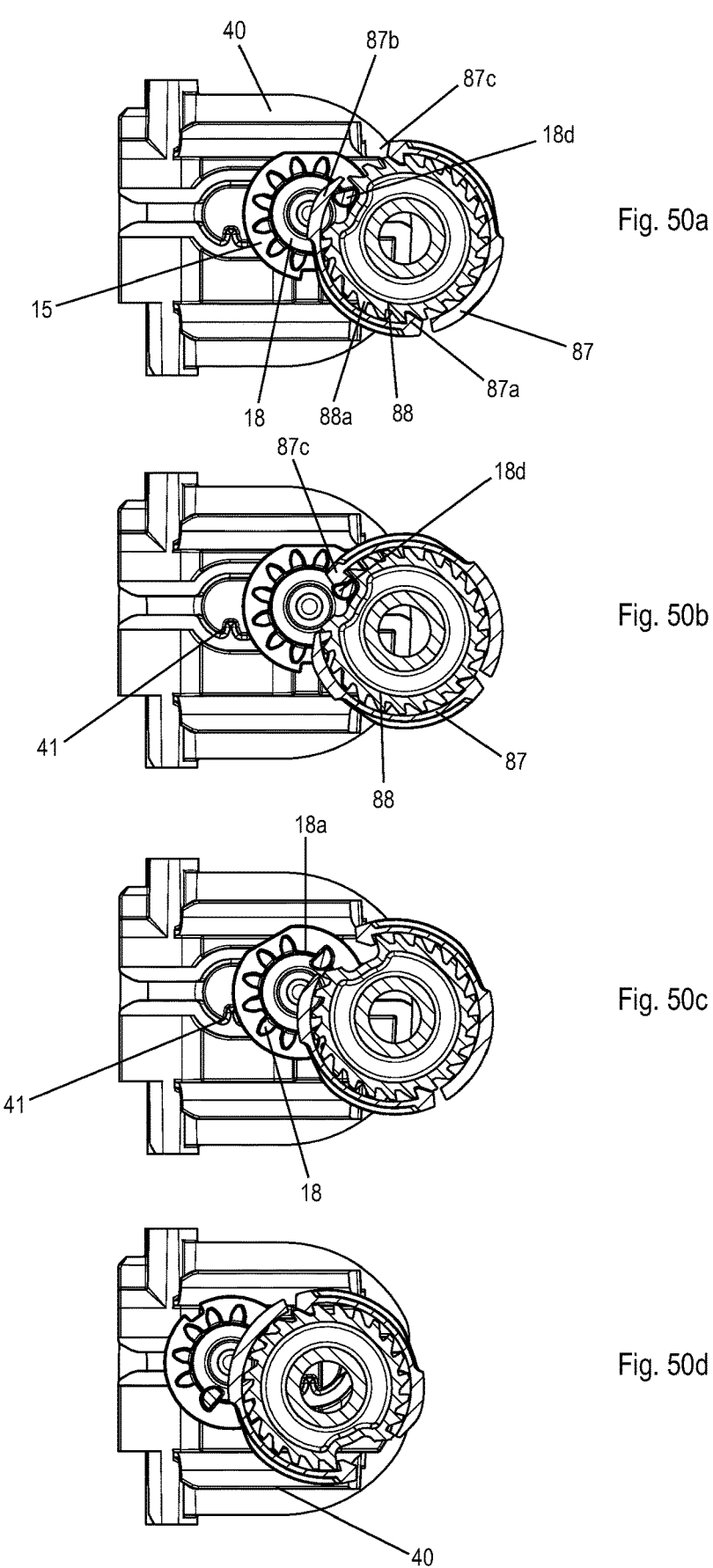
FIGS. 50*a*-50*d*: A needle insertion mechanism with a blocking member according to a fifth embodiment: Interaction of the protrusion on the gear wheel of the cam shaft with a ratchet member.

FIG. 50*a* shows a side view of the slider 40 with the cam shaft 15. The gear teeth of the gear wheel 16 engaging the gear rack 41. The cam shaft 15 includes gear teeth 18 that are axially displaced from the gear teeth engaging the gear rack 41 (FIGS. 50*b* and 50*c*). The gear teeth 18 drive the cam shaft 15 and are part of the coupling or gearing arrangement 17 presented in FIG. 1. The coupling arrangement 17 furthermore includes a cylindrical ratchet member 87 having flexible arms with teeth 87*a* pointing towards the center. The ratchet member 87 has a cut out or opening 87*c* and a strengthened section 87*b* adjacent to the opening 87*c*. The ratchet member 87 includes a set of gear teeth that engage the gear teeth 18 of the cam shaft 15. The coupling arrangement furthermore includes a ratchet wheel 88 located inside the ratchet member 87. The ratchet wheel 88 has ratchet teeth 88*a* forming a one way ratchet with the teeth 87*a* on the flexible arms of the ratchet member 87. Thus rotation of the ratchet member 87 (for example by the active drive) in one direction is transmitted to the ratchet wheel 88 (and therewith to the cam shaft 15) whereas rotation in the opposite direction is not transmitted to the ratchet wheel 88 (and therewith not to the cam shaft 15).

The initial or blocking position for the ratchet member 87 is presented in FIG. 50*a*. The opening 87*c* in the ratchet member 87 is not aligned with the protrusion 18*d* extending from the cam shaft into the ratchet member 87 and the protrusion 18*d* abuts a strengthened section 87*b* on the ratchet member 87 thus preventing rotation of the cam shaft 15 and therewith also movement of the slider 40 towards the second slider position. Rotation of the ratchet wheel 88 in the counterclockwise direction is transmitted into a rotation of the ratchet member 87 due to the one-way ratchet formed by ratchet teeth 87*a*, 88*a* such that the opening 87*c* is available for the protrusion 18*d*. This initial rotation of the ratchet member 87 is not transmitted to the cam shaft 15 as there are missing teeth 18*a* (FIG. 50*c*). The gearing engagement between the ratchet member 87 and the cam shaft 15 via the gear teeth 18 will be established during the initial rotation that may be required to unlock the cam shaft 15. Further rotation of the ratchet wheel 88 in the counterclockwise direction is transmitted to the ratchet member 87 and this rotation is, due the gearing engagement between the ratchet member 87 and the gear teeth 18 of the cam shaft, now transferred to the cam shaft 15. Rotation of the cam shaft 15 will shift the slider 40 into the second slider position (FIG. 50*d*).

A cross-section for a needle insertion mechanism with a blocking member according to a sixth embodiment is presented in FIGS. 51*a* to 53*c*. The sixth embodiment closely resembles the first embodiment presented in FIGS. 38*a* to 40, but an additional resilient member or biasing member such as a resilient arm is positioned between the gear rack and the housing. The resilient member may be part of the gear rack 41 or part of the housing 10 or part of both.

Figure 51A:
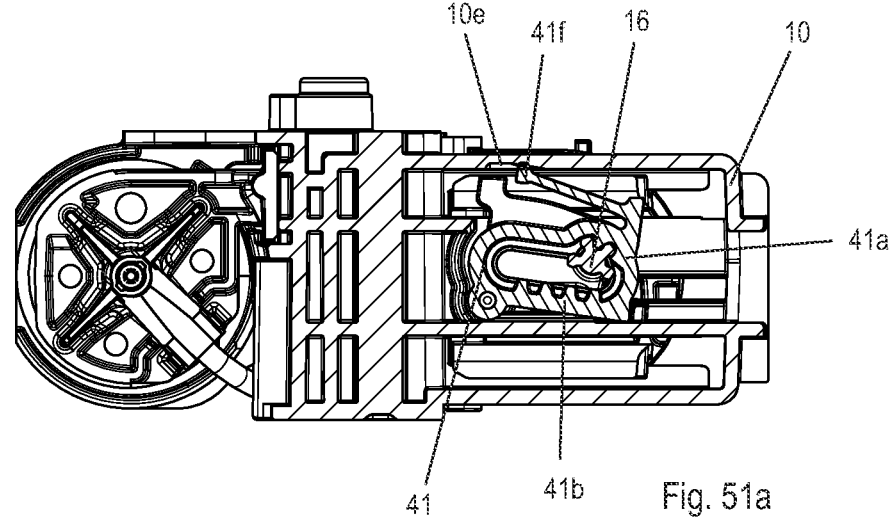
FIGS. 51*a*-51*c*: A needle insertion mechanism with a blocking member according to a sixth embodiment, a biasing member biases the pivot mounted gear rack towards the tilted position.
Figure 51B:
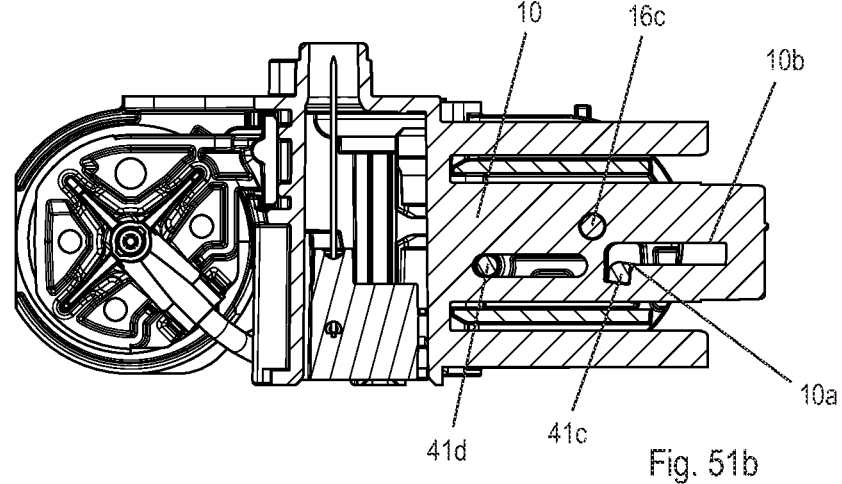
Figure 51C:
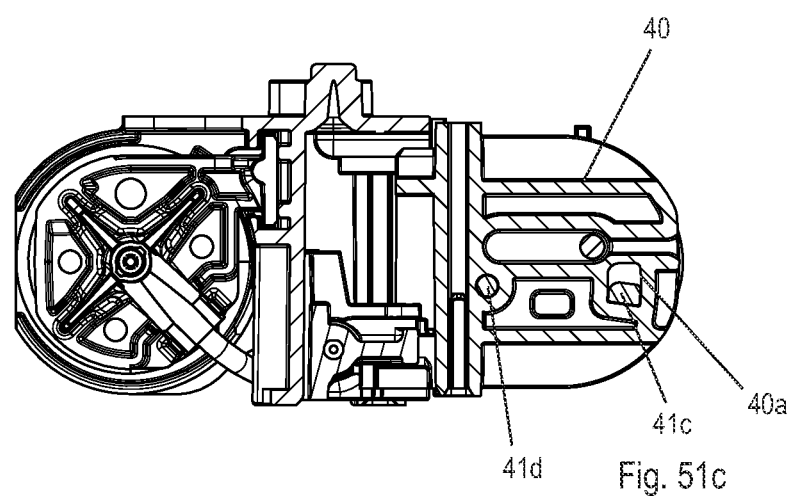

The slider 40 includes the pivot mounted gear rack 41 having a first protrusion 41*d* extending from the surface of the gear rack 41, passing through a passage in the housing 10 (FIG. 51*b*) and engaging a complementary bore in the slider 40 (FIG. 51*c*). The pivot mounted gear rack 41 includes a second protrusion 41*c* passing through a guide slot 10*a*, 10*b* in the housing 10 (FIG. 51*b*) and finally engaging a guide slot 40*a* in the slider 40 (FIG. 51*c*). The passages and guide slots in the housing allow for rotating or pivot movement of the gear rack 41 around the first protrusion 41*d*. The gear rack 41 is in the tilted position as presented in FIG. 51*a* and the gear wheel 16 engages the first section 41*a* of the gear teeth. The second protrusion 41*c* engages the guide slot 40*a* in the slider 40 and also engages the first section 10*a* of the guide slot in the housing. In the tilted position of the gear rack, the gear rack 41, and therewith also the slider 40, is prevented from movement towards the second slider position as the second protrusion 41*c* engages the first section 10*a* of the guide which is oriented perpendicular to the sliding direction for the slider. The second protrusion 41*c* is therefore in a form fit engagement with the housing 10 preventing movement of the slider out of the first slider position towards the second slider position. Additional to the first embodiment, the sixth embodiment includes an elastic arm 41*f* engaging a gear track 10*e* on the housing (FIG. 51*a*). The elastic arm 41*f* biases the pivot mounted gear rack 41 towards the tilted position and therewith keeps the engagement 41*c*, 10*a* in the blocked position (FIG. 51*b*), thereby providing an additional feature preventing movement of the slider 40 during an impact.

Figure 52A:
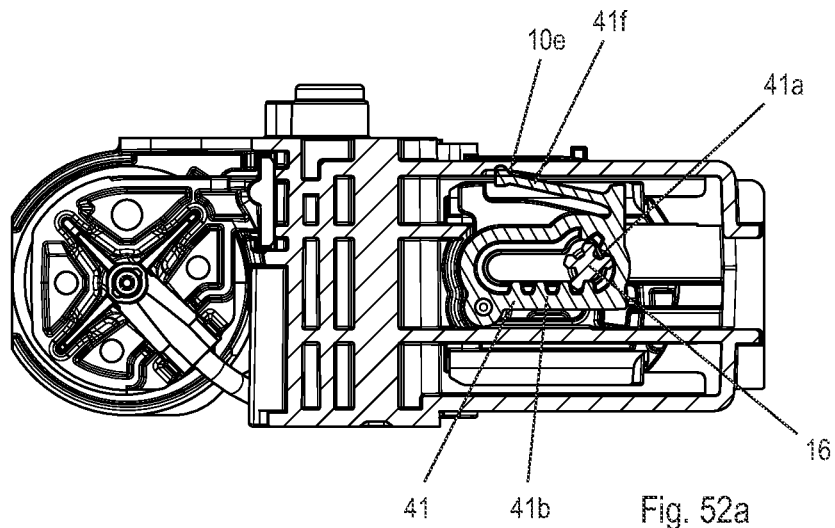
FIGS. 52*a*-52*c*: A needle insertion mechanism with a blocking member according to the sixth embodiment: Pivot mounted gear rack in the untilted position unblocking the slider movement.
Figure 52B:
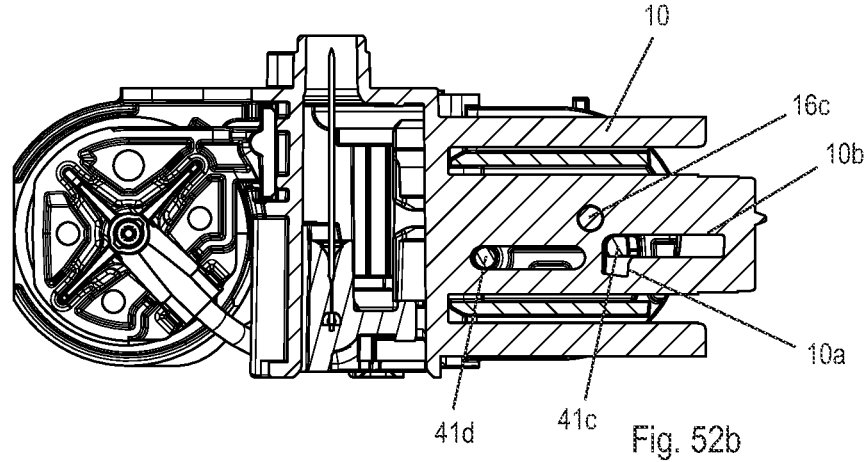
Figure 52C:
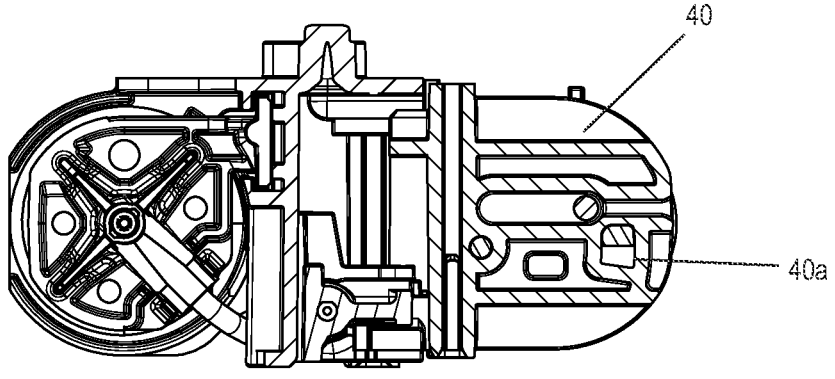
Figure 53A:
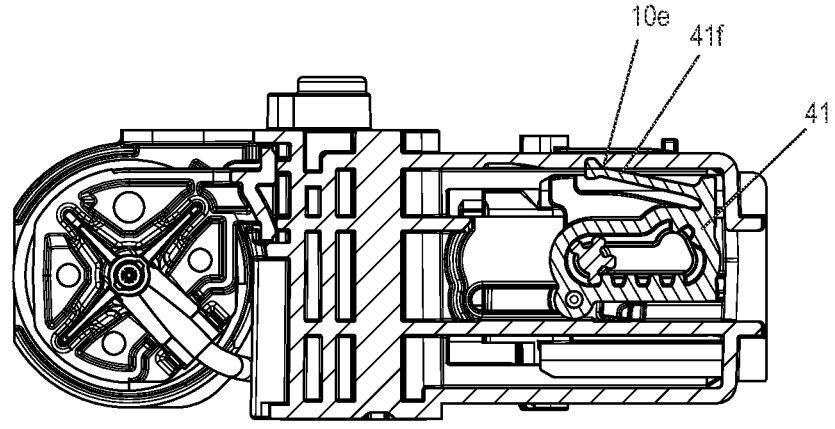
FIGS. 53*a*-53*c*: A needle insertion mechanism with a blocking member according to the sixth embodiment: Pivot mounted gear rack in the untilted position and slider moved towards the second slider position.
Figure 53B:
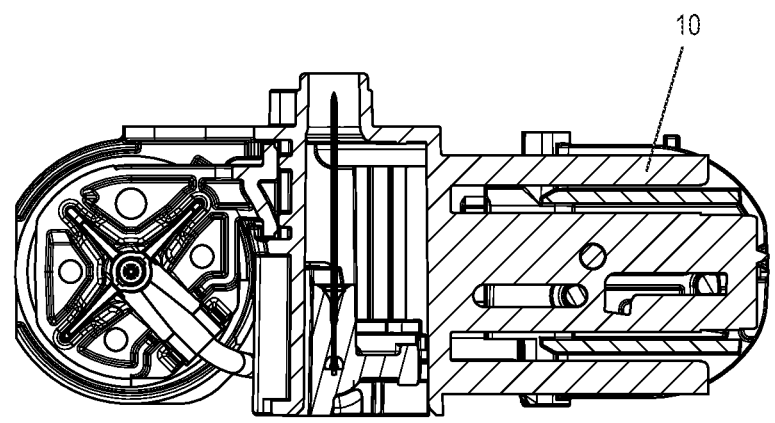
Figure 53C:
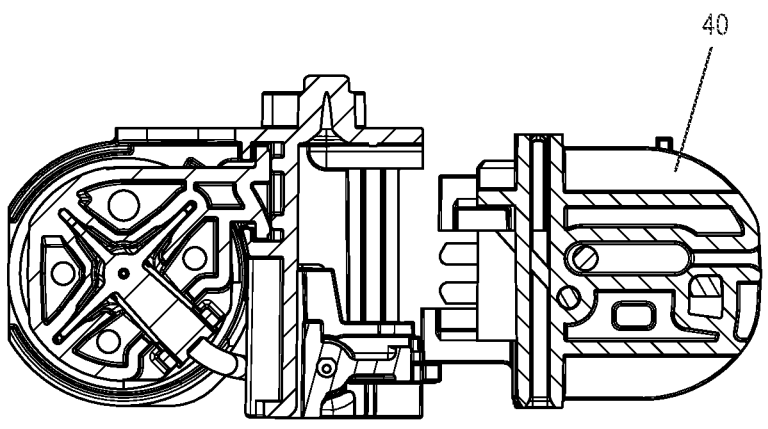

Rotation of the cam shaft 15 in the counterclockwise direction rotates the gear rack 41 around the first protrusion 41*d* from the tilted to the untilted position (FIG. 52*a*) against the bias provided by the elastic arm 41*f*. The teeth of the gear wheel 16 engage the first section 41*a* of the gear rack 41 that is oriented parallel to the skin needle 25 and rotation of the cam shaft 15 rotates the pivot mounted gear rack 41. The second protrusion 41*c* moves through the first section 10*a* of the guide slot in the housing 10 (FIG. 52*b*) and moves through the guide slot 40*a* in the slider 40 (FIG. 52*c*). Further rotation of the cam shaft 15 in the counterclockwise direction ensures that the second section 41*b* of the gear teeth of the gear rack 41 is activated and the rotation moves the gear rack 41 together with the slider 40 out of the first position towards the second position. The first protrusion 41*d* of the gear rack 41 engages the slider 40 in a bore and the second protrusion 41*c* engages the guide slot 40*a* and both allow for load transfer from the gear rack 41 to the slider 40 such that both the gear rack 41 and the slider 40 can move into the second position with respect to the housing 10 (FIGS. 53*a*, 53*b* and 53*c*). The second protrusion 41*c* has moved from the first section 10*a* of the guide slot into the second section 10*b* of the guide slot in the housing. The second section 10*b* of the guide slot in the housing allows for lateral movement of the second protrusion 41*c* on the gear rack with respect to the housing 10. The end of the elastic arm 41*f* engages the guide track 10*e* on the housing 10 during movement of the slider 40 (FIG. 53*a*).

The release of the form fit engagement between the second protrusion 41*c* and the housing 10 therefore unblocks the movement of the gear rack 41 (being an example of a blocking member) and therewith also unblocks the movement of the slider 40.

In the claims, the word "comprising" does not exclude other elements or steps, and the indefinite article "a" or "an" does not exclude a plurality. For example "a blocking member" does not exclude the fact that there may be two blocking members that functionally or structurally fulfill the purpose of "a blocking member". The mere fact that certain elements or steps are recited in distinct claims shall not preclude the existence of further meaningful combinations of these elements or steps.

1 drive module
  2 insertion and retraction module
  3 insertion and retraction mechanism
  4 product container
  5 pierceable wall/septum
  10 housing, mechanic holder
  10*a* first section guide slot
  10*b* second section guide slot
  10*c* protrusion housing
  10*d* longitudinal passage
  10*e* guide track
  11 first housing
  11*a* axial stop
  11*b* stop surface
  12 second housing
  13 linear guide
  14 linear guide
  15 drive shaft, cam shaft
  15*a* abutment surface cam shaft
  16 gear wheel/pinion
  16*a* missing tooth gear wheel
  16*b* bearing cam shaft housing
  16*c* shaft end
  16*d* protrusion/blocking member
  17 coupling member
  18 gear teeth coupling arrangement
  18*a* missing tooth
  18*d* protrusion
  20 needle carrier, needle holder
  21 counter stop surface
  22 stop surface
  23 stop surface
  25 needle, insertion needle
  30 spring/lever spring
  31 first spring member
  31*a* first spring arm
  31*b* first helical spring section
  32 second spring member
  32*a* second spring arm
  32*b* second helical spring section
  33 interconnecting section
  40 control element/slider
  40*a* guide slot slider
  40*b* second guide slot slider 40*c* first section
40*d* second section
41 gear rack/rack/blocking member
41*a* first part or section gear rack
41*b* second part or section gear rack
41*c* second protrusion
41*d* first protrusion
41*e* passage slider
41*f* elastic arm
42 cap
43 main body
44 (first) stop surface
45 linear guide
46 linear guide
47 retaining surface
50 first intermediate member
51 counter stop surface
52 releasable coupling arrangement
53 first coupling member of slider
53*a* sloped surface
54 second coupling member of housing
54*a* sloped surface
54*b* ratchet teeth
55 elastic arm
56 third coupling member of slider
57 fourth coupling member of housing
57*b* ratchet teeth
60 second intermediate member
61 counter stop surface
70 hollow spike
71 motion-link
72 first part slotted link housing
73 second part slotted link housing
80 spike carrier
81 counter surface
85 flexible tube
86 bearing engagement
87 ratchet member
87*a* tooth on resilient arm
87*b* strengthened section
87*c* cut out/opening
88 ratchet wheel
88*a* ratchet teeth
90 spring

What is claimed is:

1. A needle insertion mechanism for an injection device, comprising:
a housing;
a needle holder holding an insertion needle, the needle holder linearly guided by the housing and movable along a longitudinal axis of the needle;
a slider linearly guided by the housing and transversely moveable with respect to the longitudinal axis of the needle from a first slider position to a second slider position,
wherein in the first slider position, the slider is operatively coupled to the needle holder thereby retaining the needle holder in a needle retracted position against a bias of a spring force acting on the needle holder,
wherein in the second slider position, the slider is decoupled from the needle holder and the needle holder is moved into a needle insertion position by the spring force; and
a blocking member formed as a gear rack arranged between the slider and the housing, wherein the gear rack blocks a movement of the slider from the first slider position to the second slider position and is moveable by an active drive comprising a rotatable cam shaft in a bearing engagement with the housing and configured for unblocking the movement of the slider, and
wherein a movement of the gear rack by the rotatable cam shaft of the active drive subsequently moves the slider to the second slider position, and
wherein the gear rack is pivot-mounted to the slider, and rotation of the cam shaft tilts the gear rack from a tilted position to an untilted position.

2. The needle insertion mechanism according to claim 1, wherein the pivot-mounted gear rack is biased towards the tilted position.

3. The needle insertion mechanism according to claim 2, wherein the pivot-mounted gear rack comprises a passage or a cut-out which is not aligned with or abuts a complementary protrusion to on the housing when the pivot-mounted gear rack is in the tilted position, thereby blocking movement of the slider out of the first slider position towards the second slider position, and wherein the passage or cut-out is aligned with the complementary protrusion or the abutment between the passage or cut-out and the complementary protrusion is released when the pivot-mounted gear rack is in the untilted position thereby allowing a relative movement between the passage or cut-out and the protrusion and allowing the movement of the slider from the first slider position to the second slider position.

4. The needle insertion mechanism according to claim 1, wherein the pivot-mounted gear rack comprises gear teeth engaging a gear wheel that is a part of or is coupled to the cam shaft.

5. The needle insertion mechanism according to claim 4, wherein the gear teeth of the gear rack comprise a first section and a second section, wherein one of the first section or second section of the gear teeth of the gear rack enables a movement of the gear rack from the tilted position to the untilted position and the other one of the first section or second section of the gear teeth of the gear rack enables the movement of the slider from the first slider position to the second slider position.

6. The needle insertion mechanism according to claim 5, wherein the pivot-mounted gear rack comprises at least one protrusion engaging a bore in the housing allowing for a pivot movement and at least one second protrusion engaging a guide track in the housing forming a motion-link system.

7. The needle insertion mechanism according to claim 6, wherein the at least one second protrusion is guided by the motion-link system between the gear rack and the housing preventing the gear rack from returning back to the tilted position once the slider has moved out of the first slider position.

8. The needle insertion mechanism according to claim 7, wherein a part of the housing is arranged between the slider and the gear rack.

9. The needle insertion mechanism according to claim 1, wherein the pivot-mounted gear rack is biased towards the tilted position by an elastic member configured as an elastic arm positioned between the housing and the pivot-mounted gear rack.

10. An injection device, comprising:
a needle insertion mechanism, the needle insertion mechanism comprising:
a housing;
a needle holder holding an insertion needle, the needle holder linearly guided by the housing and movable along a longitudinal axis of the needle;

a slider linearly guided by the housing and transversely moveable with respect to the longitudinal axis of the needle from a first slider position to a second slider position, wherein in the first slider position, the slider is operatively coupled to the needle holder thereby retaining the needle holder in a needle retracted position against a bias of a spring force acting on the needle holder, wherein in the second slider position, the slider is decoupled from the needle holder and the needle holder is moved into a needle insertion position by the spring force; and a blocking member formed as a gear rack arranged between the slider and the housing, wherein the gear rack blocks a movement of the slider from the first slider position to the second slider position and is moveable by an active drive for unblocking the movement of the slider, wherein the active drive subsequently moves the slider to the second slider position, and wherein the gear rack prevents unintentional activation of the needle insertion mechanism when exposed to a drop test according to EN ISO 11608-1:2015 or a drop test from a height of 1 meter onto a drop surface selected from a concrete floor or wood having a density >600 kg/m3.

11. A needle insertion mechanism for an injection device, comprising:

a housing;

a needle holder holding an insertion needle, the needle holder being linearly guided by the housing and movable along a longitudinal axis of the needle;

a slider linearly guided by the housing and transversely moveable with respect to the longitudinal axis of the needle from a first slider position to a second slider position,

wherein in the first slider position, the slider is operatively coupled to the needle holder thereby retaining the needle holder in a needle retracted position against a bias of a spring force acting on the needle holder, wherein in the second slider position, the slider is decoupled from the needle holder and the needle holder is moved into a needle insertion position by the spring force; and a gear rack arranged between the slider and the housing, which blocks a movement of the slider from the first slider position to the second slider position, and wherein the gear rack is moveable by an active drive thereby unblocking the movement of the slider and the active drive subsequently moves the slider to the second slider position.

12. The needle insertion mechanism according to claim 11, wherein the active drive comprises a rotatable cam shaft in a bearing engagement with the housing, the cam shaft configured to drive the gear rack that is a part of or coupled to the slider.

13. The needle insertion mechanism according to claim 12, wherein the gear rack is pivot-mounted to the slider and moveable from a tilted position to an untilted position, and wherein the pivot mounted gear rack is biased towards the tilted position.

14. The needle insertion mechanism according to claim 13, wherein rotation of the cam shaft tilts the gear rack from the tilted position to the untilted position, thereby unblocking the movement of the slider.

15. The needle insertion mechanism according to claim 13, wherein the pivot-mounted gear rack is biased towards the tilted position by an elastic member configured as an elastic arm positioned between the housing and the pivot-mounted gear rack.

* * * * *